US009657091B2

(12) United States Patent
Pfeifer et al.

(10) Patent No.: US 9,657,091 B2
(45) Date of Patent: *May 23, 2017

(54) HUMANIZED TAU ANTIBODY

(71) Applicants: AC Immune S.A., Lausanne (CH); KATHOLIEKE UNIVERSITEIT LEUVEN, Leuven (BE)

(72) Inventors: Andrea Pfeifer, St-Legier (CH); Andreas Muhs, Cugy (CH); Maria Pihlgren, Mont-sur-Lausanne (CH); Oskar Adolfsson, Bercher (CH); Fred Van Leuven, Linden (BE)

(73) Assignees: AC Immune S.A., Lausanne (CH); Katholieke Universiteit Leuven, Leuven (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/390,085

(22) PCT Filed: Mar. 15, 2013

(86) PCT No.: PCT/US2013/032341
§ 371 (c)(1),
(2) Date: Oct. 2, 2014

(87) PCT Pub. No.: WO2013/151762
PCT Pub. Date: Oct. 10, 2013

(65) Prior Publication Data
US 2015/0175682 A1 Jun. 25, 2015

Related U.S. Application Data

(60) Provisional application No. 61/620,880, filed on Apr. 5, 2012.

(51) Int. Cl.
*G01N 33/68* (2006.01)
*C07K 16/18* (2006.01)

(52) U.S. Cl.
CPC ......... *C07K 16/18* (2013.01); *G01N 33/6896* (2013.01); *C07K 2317/24* (2013.01); *C07K 2317/565* (2013.01); *C07K 2317/92* (2013.01); *G01N 2333/4703* (2013.01); *G01N 2800/28* (2013.01); *G01N 2800/52* (2013.01)

(58) Field of Classification Search
None
See application file for complete search history.

(56) References Cited

U.S. PATENT DOCUMENTS

| | | |
|---|---|---|
| 5,004,697 A | 4/1991 | Pardridge |
| 5,112,596 A | 5/1992 | Malfroy-Camine |
| 5,268,164 A | 12/1993 | Kozarich et al. |
| 5,506,206 A | 4/1996 | Kozarich et al. |
| 5,686,416 A | 11/1997 | Kozarich et al. |
| 5,843,779 A | 12/1998 | Vandermeeren et al. |
| 6,514,221 B2 | 2/2003 | Hynynen et al. |
| 6,953,794 B2 | 10/2005 | Wischik et al. |
| 7,034,036 B2 | 4/2006 | Schoenhard |
| 7,220,833 B2 | 5/2007 | Nelson et al. |
| 7,408,027 B1 | 8/2008 | Mandelkow et al. |
| 8,012,936 B2 | 9/2011 | Sigurdsson et al. |
| 8,093,357 B2 | 1/2012 | Lazar et al. |
| 8,663,650 B2 | 3/2014 | Nicolau et al. |
| 9,304,138 B2 | 4/2016 | Pfeifer et al. |
| 2002/0025313 A1 | 2/2002 | Micklus et al. |
| 2002/0065259 A1 | 5/2002 | Schatzberg et al. |
| 2002/0086009 A1 | 7/2002 | Ishiguro et al. |
| 2003/0083299 A1 | 5/2003 | Ferguson |
| 2003/0129186 A1 | 7/2003 | Beliveau et al. |
| 2003/0162695 A1 | 8/2003 | Schatzberg et al. |
| 2004/0131692 A1 | 7/2004 | Kreuter et al. |
| 2004/0265920 A1 | 12/2004 | Seubert et al. |
| 2005/0089473 A1 | 4/2005 | Black et al. |
| 2005/0124533 A1 | 6/2005 | Schatzberg et al. |
| 2005/0221391 A1 | 10/2005 | Davies |
| 2005/0261475 A1 | 11/2005 | Tseng et al. |
| 2007/0253966 A1 | 11/2007 | Glaesner et al. |
| 2008/0220449 A1 | 9/2008 | Vasan et al. |
| 2010/0285108 A1 | 11/2010 | Pfeifer et al. |
| 2012/0276009 A1 | 11/2012 | Pfeifer et al. |
| 2014/0255412 A1 | 9/2014 | Pfeifer et al. |

(Continued)

FOREIGN PATENT DOCUMENTS

| | | |
|---|---|---|
| EA | 200602015 A1 | 2/2007 |
| EP | 2210901 | 7/2010 |
| WO | WO 96/13590 | 5/1996 |

(Continued)

OTHER PUBLICATIONS

Rafii 2009 "recent developments in alzheimers disease therapeutics" BMC med 7:7.*
Velden 2003 "detection of minimal residual disease in hematologic malignancies by real-time quantitative PCR: principles, approaches, and laboratory aspects" Leukemia 17:1013-1034.*
Wikipedia 2016 "minimal residual disease" accessed from wikipedia.org on Jan. 21, 2016.*
Alonso et al., Abnormal phosphorylation of tau and the mechanism of Alzheimer neurofibrillary degeneration: sequestration of microtubule-associated proteins 1 and 2 and the disassembly of microtubules by the abnormal tau, PNAS, (1997), 94:298-303.

(Continued)

*Primary Examiner* — Adam M Weidner
(74) *Attorney, Agent, or Firm* — McNeill Baur PLLC

(57) ABSTRACT

The present invention provides methods and compositions for the therapeutic and diagnostic use in the treatment of diseases and disorders which are caused by or associated with neurofibrillary tangles. In particular, the invention relates to humanized antibodies, which specifically recognize and bind to phosphorylated pathological protein tau-conformers to methods and compositions involving said antibodies for the therapeutic and diagnostic use in the treatment of tauopathies including Alzheimer's Disease (AD).

22 Claims, 23 Drawing Sheets

(56) References Cited

U.S. PATENT DOCUMENTS

2014/0294731 A1    10/2014    Pfeifer et al.

FOREIGN PATENT DOCUMENTS

| WO | WO 96/20218 | 7/1996 |
| --- | --- | --- |
| WO | WO 96/29605 | 9/1996 |
| WO | WO 98/22120 | 5/1998 |
| WO | WO 02/46237 A2 | 6/2002 |
| WO | WO 2004/058258 | 7/2004 |
| WO | WO 2005/080986 | 9/2005 |
| WO | WO 2005/081872 | 9/2005 |
| WO | WO 2007/068105 | 6/2007 |
| WO | WO 2007/068411 | 6/2007 |
| WO | WO 2010/106127 | 9/2010 |
| WO | WO 2010/115843 | 10/2010 |
| WO | WO 2010/144711 | 12/2010 |
| WO | WO 2011/013034 | 2/2011 |
| WO | WO 2012/045882 | 4/2012 |
| WO | WO 2013/050567 | 4/2013 |
| WO | WO 2013/151762 | 10/2013 |

OTHER PUBLICATIONS

Verma et al. Adjuvant effects of liposomes containing lipid A: enhancement of liposomal antigen presentation and recruitment of macrophages, Infect. Immun., 1992, 60:2438-2444.

Asuni et al., Immunotherapy targeting pathological tau conformers in a tangle mouse model reduces brain pathology with associated functional improvements, (2007), J Neurosc. 27 (34), 9115-29.

Bhaskar et al., Tyrosine phosphorylation of tau accompanies disease progression in transgenic mouse models of tauopathy, (2010) Neuropathol Appl Neurobiol, 36:462-477.

d'Abramo et al., Tau passive immunotherapy in mutant P301L mice: antibody affinity versus specificity, (2013), PLoSone, 8:e62402, 10 pages.

Dominguez et al., Novel therapeutic strategies provide the real test for the amyloid hypothesis of Alzheimer's disease, Trends Pharmacol Sci, 2002, 23:324-330.

Gill et al., Direct brain infusion of glial cell line-derived neurotrophic factor in Parkinson disease, 2003, Nature Med. 9:589-595.

Greenberg et al. Hydrofluoric acid-treated tau PHF proteins display the same biochemical properties as normal tau, (1992), J Biol. Chem., 267:564-569.

Hirata-Fukae et al., Levels of soluble and insoluble tau reflect overall status of tau phosphorylation in vivo, (2009), Neurosci Lett, 450:51-55.

Hoffmann et al., Unique Alzheimer's disease paired helical filament specific epitopes involve double phosphorylation at specific sites, (1997), Biochemistry, 36, 8114-8124.

"Instructions for Authors," The Journal of Neuroscience, publishe [online] Jun. 29, 1998, retrieved from <https://web.archive.org/web/19980629153321/http://jneurosci.org/misc/itoa.shtiml> on Jan. 7, 2015.

Jicha et al., cAMP-dependent protein kinase phosphorylations on tau in Alzheimer's disease, (1999), J Neurosci, 19:7486-7494.

Khaw et al., Technetium-99m labeling of antibodies to cardiac myosin Fab and to human fibrinogen, 1982, J. Nucl. Med. 23:1011-1019.

Lee et al., Phosphorylation of tau by fyn: implications for Alzheimer's disease, (2004), J. Neurosci, 24:2304-2312.

Lichtenberg-Kraag et al., Phosphorylation-dependent epitopes of neurofilament antibodies on tau protein and relationship with Alzheimer tau, (1992), PNAS, 89:5384-5388.

Masliah et al., Effects of alpha-synuclein immunization in a mouse model of Parkinson's disease, (2005), Neuron, 46(6):857-68.

Masliah et al., Passive immunization reduces behavioral and neuropathological deficits in an alpha-synuclein transgenic model of Lewy body disease, (2011) PLoS ONE, vol. 6(4):e19338,17 pages.

Muhs et al., Liposomal vaccines with conformation-specific amyloid peptide antigens define immune response and efficacy in APP transgenic mice, (2007) Proc Natl Acad Sci USA, 104(23):9810-5.

Muyllaert et al, Glycogen synthase kinase-3beta, or a link between amyloid and tau pathology?, (2008) Genes Brain Behav., Suppl. 1:57-66.

Nicolau et. al., A liposome-based therapeutic vaccine against beta-amyloid plaques on the pancreas of transgenic NORBA mice, (2002) Proc Natl. Acad. Sci USA 99:2332-2337.

Oddo et al., Reduction of soluble Abeta and tau, but not soluble Abeta alone, ameliorates cognitive decline in transgenic mice with plaques and tangles, (2006), J Biol Chem, 281:39413-39423.

Otvos et al., Monoclonal antibody PHF-1 recognizes tau protein phosphorylated at serine residues 396 and 404, (1994), J Neurosci Res., 39:669-673.

Queen et al., A humanized antibody that binds to the interleukin 2 receptor, (1989) Proc. Natl Acad Sci USA, 86:10029-10032.

Papanastassiou et al., The potential for efficacy of the modified (ICP 34.5(-)) herpes simplex virus HSV1716 following intratumoural injection into human malignant glioma: a proof of principle study, 2002, Gene Therapy 9:398-406.

Roberson et al, Reducing endogenous tau ameliorates amyloid beta-induced deficits in an Alzheimer's disease mouse model, (2007) Science, 316(5825):750-4.

Roder et al., Phosphorylation-dependent monoclonal Tau antibodies do not reliably report phosphorylation by extracellular signal-regulated kinase 2 at specific sites, (1997), J Biol Chem, 272:4509-4515.

Sela et al., Therapeutic vaccines: realities of today and hopes for the future, Drug Discov Today, 2002, 7:664-673.

Singer et al., Immuno-PCR-based quantification of multiple phosphorylated tau-epitopes linked to Alzheimer's disease, (2009), Anal Bioanal Chem, 395:2263-2267.

Singer et al., Characterization of Phosphorylation Dependent Antibodies to Sutdy the Phosphorylation Status of the Tau Protein, (2005), Intl J Peptide Res Therapeutics, 11:279-289.

Staubli et al., Aniracetam has Proportionately Smaller Effects on Synapses Expressing Long-Term Potentiation: Evidence that Receptor Changes Subserve LTP, Psychobiology, 1990, 18:377-381.

Terwel et al., Changed conformation of mutant Tau-P301L underlies the moribund tauopathy, absent in progressive, nonlethal axonopathy of Tau-4R/2N transgenic mice, (2006) J Biol Chem, 280:3963-3973.

Terwel et al, Amyloid activates GSK-3beta to aggravate neuronal tauopathy in bigenic mice, (2008) Am J pathol., 172(3):786-98.

Torreilles et al., Binding specificity of monoclonal antibody AD2: influence of the phosphorylation state of tau, (2000), Molecular Brain Res., 78:181-185.

Urushitiani et al., Therapeutic effects of immunization with mutant superoxide dismutase in mice models of amyotrophic lateral sclerosis, (2007) Proc. Natl Acad Sci USA, 104(79):2495-500.

Vandebroek et al., Identification and isolation of a hyperphosphorylated, conformationally changed intermediate of human protein tau expressed in yeast, (2005), Biochemistry, 44:11466-11475.

Vandebroek et al., Microtubule binding and clustering of human Tau-4R and Tau-P301L proteins isolated from yeast deficient in orthologues of glycogen synthase kinase-3beta or cdk5, (2006), J Biol Chem 281:25388-25397.

Vanhelmont et al., Serine-409 phosphorylation and oxidative damage define aggregation of human protein tau in yeast, (2010), Fems Yeast Research, 10:992-1005.

Zemlan et al., Prehospital administration of tenecteplase for ST-segment elevation myocardial infarction in a rural EMS system, (1996), J Neurosci Res., 46:90-97.

Zheng-Fischhoefer et al., Sequential phosphorylation of Tau by glycogen synthase kinase-3beta and protein kinase A at Thr212 and Ser214 generates the Alzheimer-specific epitope of antibody AT100 and requires a paired-helical-filament-like conformation, (1998), Euro J Biochem, 252:542-552.

International Search Report and Written Opinion for PCT/EP2012/069783, mailed Jan. 25, 2013, 18 pages.

(56) References Cited

OTHER PUBLICATIONS

International Search Report and Written Opinion for PCT/EP2011/067604, mailed Apr. 3, 2012, 31 pages.
International Search Report and Written Opinion for PCT/US2013/032341, mailed Sep. 3, 2013, 22 pages.
Alonso et al., Mechanism of tau-induced neurodegeneration in Alzheimer disease and related tauopathies, Curr Alzheimer Res, (2008), 5:375-384.
Braak and Braak, Neuropathological stageing of Alzheimer-related changes., 1991, Acta Neuropathol 82:239-259.
Braak et al., Staging of Alzheimer-related cortical destruction, (1993), Eur.Neurol., 33:403-408.
Harlow and Lane, Antibodies: A Laboratory Manual (Cold Spring Harbor Laboratory, New York 1988 553-612.
Hodgson, Making monoclonals in microbes, (1991) Bio/Technology, 9:421-425.
Kennedy et al., Protein-protein coupling reactions and the applications of protein conjugates, 1976, Clin. Chim. Acta 70:1-31.
Lewis et al., Neurofibrillary tangles, amyotrophy and progressive motor disturbance in mice expressing mutant (P301L) tau protein, (2000) Nature Genetics, 25:402-405.
Muyllaert et al, Transgenic mouse models for Alzheimer's disease: the role of GSK-3B in combined amyloid and tau-pathology, (2006) Rev Neurol, 162(10):903-907.
Neuwelt, E. A., Implication of the Blood-Brain Barrier and its Manipulation, vols. 1 & 2, Plenum Press, N. Y. (1989), TOC Only.
Nicoll et al., Neuropathology of human Alzheimer disease after immunization with amyloid-beta peptide: a case report, (2003) Nature Med, 9:448-452.
Oddo et al., Abeta immunotherapy leads to clearance of early, but not late, hyperphosphorylated tau aggregates via the proteasome, (2004) Neuron, 43:321-332.
Reig S., et al. Immunogold labelling of paired helical filaments and amyloid fibrils by specific monoclonal and polyclonal antibodies, (1995), Acta Neuropathol., 90:441-447.
Ribe et al., Accelerated amyloid deposition, neurofibrillary degeneration and neuronal loss in double mutant APP/tau transgenic mice, (2005) Neurobiol Dis, 20(3):814-22.
Rousseaux et al. Methods Enzymology, Optimal conditions for the preparation of proteolytic fragments from monoclonal IgG of different rat IgG subclasses., (1986), Academic Press 121:663-69.
Schurs et al. Enzyme-Immunoassay, 1977, Clin. Chim Acta 57:1-40.
Vandebroek et al., "Phosphorylation and Aggregation of Protein Tau in Humanized Yeast Cells and in Transgenic Mouse Brain"; 7th International Conference on Alzheimer's and Parkinson's Disease, Sorrento, Italy, Mar. 9-13, 2005, pp. 15-19.
Wagner et al. The crossflow injection technique: an improvement of the ethanol injection method, (2002) Journal of Liposome Research, 12(3):259-270.
Labrijn et al., "Therapeutic IgG4 antibodies engage in Fab-arm exchange with endogenous human IgG4 in vivo," Nature Biotech., 27(8): 767-771 (2009).
Rosenmann et al., Tauopathy-like abnormalities and neurologic deficits in mice immunized with neuronal tau protein, (2006) Arch Neurol, 63(10):1459-1467.
Tabira, Immunization therapy for Alzheimer disease: a comprehensive review of active immunization strategies, Tohoku J Exp Med., 2010, 220:95-106.
Altshuler et al., "Reception of Recombinant Antibodies and Methods of Increase Their Affinity," Advances Biochem., 50: 203-258 (2010), with English translation (51 pages).
Johnson et al., "Cation exchange—HPLC and mass spectrometry reveal C-terminal amidation of an IgG1 heavy chain," Analytical Biochem., 360: 75-83 (2007).
Porzig et al., "Epitope mapping of mAbs AT8 and Tau5 directed against hyperphosphorylated regions of the human tau protein," Biochem. Biophys. Res. Comm., 358: 644-649 (2007).

\* cited by examiner

KpnI PstI                                                    AgeI

TTGGTACCTGCAGAAGCCAGGCCAGTCTCCACAGCTCCTGATCTACAAAGTTTCCAACCGGTTTTCTGGGGTCCAGACAGGTTCAGTGG
                                                                                             360
AACCATGGACGTCTTCGGTCCGGTCAGAGGTGTCGAGGACTAGATGTTTCAAAGGTTGGCCAAAAGACCCCAGGTCTGTCCAAGTCACC

W Y L Q K P G Q S P Q L L I Y K V S N R F S G V P D R F S G
  ────────────────────── 12G7 HuVK V1 ──────────────────────
                                   ┌──────────────────┐
  ]                                │                   ─▶
  ]                                └── CDR 2 ──┘

CAGTGGATCAGGGACAGATTTCACACTCAAGATCAGCAGAGTGGAGGCTGAGGATGTGGGAGTTTATTTCTGTTCTCAAACTGCACATTT
                                                                                             450
GTCACCTAGTCCCTGTCTAAAGTGTGAGTTCTAGTCGTCTCACCTCCGACTCCTACACCCTCAAATAAAGACAAGAGTTTGACGTGTAAA

S G S G T D F T L K I S R V E A E D V G V Y F C S Q T A H F
  ─────────────────────── 12G7 HuVK V1 ──────────────────────
                                                     ┌──────
                                                     │
                                                     └ CDR 3

BamHI

TCCCTACACCTTCGGAGGGGGACCAAGGTGGAAATCAAACGTGAGTAGAATTTAAACTTTGCTTCCTCAGTTGGATCCACTAGTCCAGT
                                                                                             540
AGGGATGTGGAAGCCTCCCCCTGGTTCCACCTTTAGTTTGCACTCATCTTAAATTTGAAACGAAGGAGTCAACCTAGGTGATCAGGTCA

P Y T F G G G T K V E I K
  ──────── 12G7 HuVK V1 ────
  ┌─────▶
  │
  └ CDR 3

Figure 5A-2

```
                EcoRI                                                                              SphI
GTGGTGGAATTCTAAACTCTGAGGGGTCGGATGACGTGGCCATTCTTTGCCTAAAGCATTGAGTTTACTGCAAGGTCAGAAAAGCATGC
+++++++++++++++++++++++++++++++++++++++++++++++++++++++++++++++++++++++++++++++++++++++++  630
CACCACCTTAAGATTTGAGACTCCCCAGCCTACTGCACCGGTAAGAAACGGATTTCGTAACTCAAATGACGTTCCAGTCTTTTCGTACG

SacI
AAAGCCCTCAGAATGGCTGCAAAGAGCTCCAACAAAACAATTTAGAACTTTATTAAGGAATAGGGGGAAGCTAGGAAGAAACTCAAAACA
+++++++++++++++++++++++++++++++++++++++++++++++++++++++++++++++++++++++++++++++++++++++++  720
TTTCGGGAGTCTTACCGACGTTTCTCGAGGTTGTTTTGTTAAATCTTGAAATAATTCCTTATCCCCCTTCGATCCTTCTTTGAGTTTTGT

SphI
TCAAGATTTTAAATACGTTCTTGGTCTCCTTGCTATAATTATCTGGGATAAGCATGCTGTTTTCTGTCTGTCCCTAACATGCCCTGTGA
+++++++++++++++++++++++++++++++++++++++++++++++++++++++++++++++++++++++++++++++++++++++++  810
AGTTCTAAAATTTATGCGAAGAACCAGAGGAACGATATTAATAGACCCTATTCGTACGACAAAAGACAGACAGGGATTGTACGGGACACT

TTATCCGCAAACAACACACCCAAGGCAGAACTTTGTTACTTAAACACCATCCTGTTTGCTTCTTTCCTCAGGAACTGTGGCTGCACCAT
+++++++++++++++++++++++++++++++++++++++++++++++++++++++++++++++++++++++++++++++++++++++++  900
AATAGGCGTTTGTTGTGTGGGTTCCCGTCTTGAAACAATGAATTTGTCGTAGGACAAACGAAGAAAGGAGTCCTTGACACCGACGTGGTA

T  V  A  A  P
                                                      R ──── HuCK ────

XmnI
CTGTCTTCATCTTCCCGCCATCTGATGAGCAGTTGAAATCTGGAACTGCCTCTGTTGTGTGCCTGCTGAATAACTTCTATCCCAGAGAGG
+++++++++++++++++++++++++++++++++++++++++++++++++++++++++++++++++++++++++++++++++++++++++  990
GACAGAAGTAGAAGGGCGGTAGACTACTCGTCAACTTTAGACCTTGACGGAGACAACACACGGACGACTTATTGAAGATAGGGTCTCTCC

S  V  F  I  F  P  P  S  D  E  Q  L  K  S  G  T  A  S  V  V  C  L  L  N  N  F  Y  P  R  E
 ════════════════════════════════════ HuCK ═══════════════════════════════════════
```

Figure 5B-1

```
CGAAAGTACAGTGGAAGGTGGATAACGCCCTCCAATCGGGTAACTCCCAGGAGAGTGTCACAGAGCAGGACAGCAAGGACAGCACCTACA
─────────────────────────────────────────────────────────────────────────────────────────── 1080
GCTTTCATGTCACCTTCCACCTATTGCGGGAGGTTAGCCCATTGAGGGTCCTCTCACAGTGTCTCGTCCTGTCGTTCCTGTCGTGGATGT
```

A K V Q W K V D N A L Q S G N S Q E S V T E Q D S K D S T Y
────────────────────────── HuCK ──────────────────────────

```
                                                                                     SacI
                                                                                      │
GCCTCAGCAGCACCCTGACGCTGAGCAAAGCAGACTACGAGAAACACAAAGTCTACGCCTGCGAAGTCACCCATCAGGGCCTGAGCTCGC
─────────────────────────────────────────────────────────────────────────────────────────── 1170
CGGAGTCGTCGTGGGACTGCGACTCGTTTCGTCTGATGCTCTTTGTGTTTCAGATGCGGACGCTTCAGTGGGTAGTCCGGACTCGAGCG
```

S L S S T L T L S K A D Y E K H K V Y A C E V T H Q G L S S
────────────────────────── HuCK ──────────────────────────

```
CCGTCACAAAGAGCTTCAACAGGGGAGAGTGTTAGAGGGAGAAGTGCCCCCACCTGCTCCTCAGTTCCAGCCTGACCCCCTCCATCCTT
─────────────────────────────────────────────────────────────────────────────────────────── 1260
GGCAGTGTTTCTCGAAGTTGTCCCCTCTCACAATCTCCCTCTTCACGGGGGTGGACGAGGAGTCAAGGTCGGACTGGGGAGGGTAGGAA
```

P V T K S F N R G E C .
────────── HuCK ──────────

```
TGGCCTCTGACCCTTTTTCACAGGGGACCTACCCCTATTGCGGTCCTCCAGCTCATCTTTCACCTCACCCCCTCCTCCTCCTTGGCTT
─────────────────────────────────────────────────────────────────────────────────────────── 1350
ACCGGAGACTGGGAAAAAGGTGTCCCCTGGATGGGATAACGCCAGGAGGTCGAGTAGAAAGTGGAGTGGGGGAGGAGGAGGAACCGAA
```

Figure 5B-2

```
TAATTATGCTAATGTTGGAGGAGAATGAATAAATAAAGTGAATCTTTGCACCTGTGGTTTCTCTCTTTCCTCATTTAATAATTATTATCT
++++++++|++++++++|++++++++|++++++++|++++++++|++++++++|++++++++|++++++++|++++++++|++++++++| 1440
ATTAATACGATTACAACCTCCTCTTACTTATTTATTTCACTTAGAAACGTGGACACCAAAGAGAGAAGGAGTAAATTATTAATAATAGA

GTTGTTTTACCAACTACTCAATTTCTCTTATAAGGACTAAATATGTAGTCATCCTAAGGCGCATAACCATTTATAAAAATCATCCTTCA
++++++++|++++++++|++++++++|++++++++|++++++++|++++++++|++++++++|++++++++|++++++++|++++++++| 1530
CAACAAAATGGTTGATGAGTTAAAGAGAATATTCCCTGATTTATACATCAGTAGGATTCCGCGTATTGGTAAATATTTTTAGTAGGAAGT

NcoI
                                                                     |
TTCTATTTTACCCTATCATCCTCTGCAAGACAGTCCTCCCTCAAACCCACAAGCCTTCTGCCTCACAGTCCCCTGGCCATGGTAGGAG
++++++++|++++++++|++++++++|++++++++|++++++++|++++++++|++++++++|++++++++|++++++++|++++++++| 1620
AAGATAAAATGGGATAGTAGGAGACGTTCTGTCAGGAGGGAGTTTGGGTGTTCGGAAGACAGGAGTGTCAGGGACCGGTACCATCCTC

AGACTTGCTTCCTTGTTTCCCCTCCTCAGCAAGCCCTCATAGTCCTTTTAAGGGTGACAGGTCTTACAGTCATATATCCTTTGATTCA
++++++++|++++++++|++++++++|++++++++|++++++++|++++++++|++++++++|++++++++|++++++++|++++++++| 1710
TCTGAACGAAGGAACAAAAGGGAGGAGTCGTTCGGAGTATCAGGAAAATTCCCACTGTCCAGAATGTCAGTATATAGGAAACTAAGT
```

```
CCGCTGTGCCAACCTCTGTCCCTACAGGGCAGCCCGGAGAGCCACAGGTGTACACCCTGCCCCCATCCCAGGAGGAGATGACCAAGAACC
++++++++++|++++++++++|++++++++++|++++++++++|++++++++++|++++++++++|++++++++++|++++++++++|++  2250
GGCGACACGGTTGGAGACAGGGATGTCCCGTCGGGCCTCTCGGTGTCCACATGTGGGACGGGGGTAGGGTCCTCCTCTACTGGTTCTTGG
```

G Q P R E P Q V Y T L P P S Q E E M T K N
           |_____ CH3 _____

```
AGGTCAGCCTGACCTGCCTGGTCAAAGGCTTCTACCCCAGCGACATCGCCGTGGAGTGGGAGAGCAATGGGCAGCCGGAGAACAACTACA
++++++++++|++++++++++|++++++++++|++++++++++|++++++++++|++++++++++|++++++++++|++++++++++|++  2340
TCCAGTCGGACTGGACGGACCAGTTTCCGAAGATGGGGTCGCTGTAGCGGCACCTCACCCTCTCGTTACCCGTCGGCCTCTTGTTGATGT
```

Q V S L T C L V K G F Y P S D I A V E W E S N G Q P E N N Y
           |_____ CH3 _____

Xmnl
                                                                               |
```
AGACCACGCCTCCCGTGCTGGATTCCGACGGCTCCTTCTTCCTCTACAGCAGGCTAACCGTGGACAAGAGCAGGTGGCAGGAGGGGAATG
++++++++++|++++++++++|++++++++++|++++++++++|++++++++++|++++++++++|++++++++++|++++++++++|++  2430
TCTGGTGCGGAGGGCACGACCTAAGGCTGCCGAGGAAGAAGGAGATGTCGTCCGATTGGCACCTGTTCTCGTCCACCGTCCTCCCCTTAC
```

K T T P P V L D S D G S F F L Y S R L T V D K S R W Q E G N
           |_____ CH3 _____

Bsgl
     |
```
TCTTCTCATGCTCCGTGATGCATGAGGCTCTGCACAACCACTACACACAGAAGAGCCTCTCCCTGTCTCTGGGTTGATGAGTGCCAGGGC
++++++++++|++++++++++|++++++++++|++++++++++|++++++++++|++++++++++|++++++++++|++++++++++|++  2520
AGAAGAGTACGAGGCACTACGTACTCCGAGACGTGTTGGTGATGTGTGTCTTCTCGGAGAGGGACAGAGACCCAACTACTCACGGTCCCG
```

```
                    XmaI
                    | SmaI
                    |  |
CGGCAAGCCCCGGCTCCCGGGCTCTCGGGGTCGCCGAGGATGCTTGGCACGTACCCGTCTACATACTTCCAGGCACCCAGCATGGA
++++++++|++++++++|++++++++|++++++++|++++++++|++++++++|++++++++|++++++++|++++++++|++++++++|  2610
GCCGTTCGGGGCGAGGGCCCGAGAGCCCCAGCGGCTCCTACGAACCGTGCATGGGCAGATGTATGAAGGTCCGTGGGTCGTACCT

ApaI
                              |
AATAAAGCACCCACCACTGCCCTGGGCCCTGTGAGACTGTGATGGTTCTTTCCACGGGTCAGGCGAGTCTGAGCCCTGAGTGACATGA
++++++++|++++++++|++++++++|++++++++|++++++++|++++++++|++++++++|++++++++|++++++++|++++++++|  2700
TTATTTCGTGGGTGGTGACGGGACCCGGGACACTCTGACACTACCAAGAAAGGTGCCCAGTCCGCTCAGACTCGGACTCACTGTACT

BsgI
                                                        |
GGGAGGCAGAGCGGGTCCGACTGTCCCGACACTGGCCCAGGCTGTGCAGGTGTGCCTGGGCCGCTAGGGTGGGGTCAGCCAGGGCTG
++++++++|++++++++|++++++++|++++++++|++++++++|++++++++|++++++++|++++++++|++++++++|++++++++|  2790
CCCTCCGTCTCGCCCAGGCTGACAGGGCTGTGACCGGGTCCGACACGTCCACACGGACCCGGCGATCCCACCCCAGTCGGTCCCGAC

KpnI
                                    | XhoI
                                    |  |
CCCTCGGCAGGGTGGGGATTTGCCAGCGTGGCCCTCCTCCAGCAGCAGGTACCTCGAG
++++++++|++++++++|++++++++|++++++++|++++++++|++++++++|++++++++→  2850
GGGAGCCGTCCCACCCCTAAACGGTCGCACCGGGAGGAGGTCGTCGTCCATGGAGCTC
```

Figure 6D-2

SEQUENCE LISTING

```
<160> NUMBER OF SEQ ID NOS: 70

<210> SEQ ID NO 1
<211> LENGTH: 10
<212> TYPE: PRT
<213> ORGANISM: Artificial Sequence
<220> FEATURE:
<223> OTHER INFORMATION: Synthetic

<400> SEQUENCE: 1

Gly Tyr Thr Phe Thr Asp Tyr Tyr Met Asn
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthetic

<400> SEQUENCE: 2

Asp Ile Asn Pro Asn Arg Gly Gly Thr Thr Tyr Asn Gln Lys Phe Lys
1               5                   10                  15

Gly

<210> SEQ ID NO 3
<211> LENGTH: 6
<212> TYPE: PRT
<213> ORGANISM: Artificial Sequence
<220> FEATURE:
<223> OTHER INFORMATION: Synthetic

<400> SEQUENCE: 3

Tyr Tyr Ala Val Gly Tyr
1               5

<210> SEQ ID NO 4
<211> LENGTH: 16
<212> TYPE: PRT
<213> ORGANISM: Artificial Sequence
<220> FEATURE:
<223> OTHER INFORMATION: Synthetic

<400> SEQUENCE: 4
```

```
Arg Ser Ser Gln Arg Leu Val His Ser His Gly Lys Thr Tyr Leu His
1               5                   10                  15
```

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

```
Lys Val Ser Asn Arg Phe Ser
1               5
```

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

```
Ser Gln Thr Ala His Phe Pro Tyr Thr
1               5
```

<210> SEQ ID NO 7
<211> LENGTH: 115
<212> TYPE: PRT
<213> ORGANISM: Artificial Sequence
<220> FEATURE:
<223> OTHER INFORMATION: Synthetic

<400> SEQUENCE: 7

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Ile
        35                  40                  45

Gly Asp Ile Asn Pro Asn Arg Gly Gly Thr Thr Tyr Asn Gln Lys Phe
    50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Tyr Tyr Ala Val Gly Tyr Trp Gly Gln Gly Thr Thr Val Thr
                100                 105                 110

Val Ser Ser
        115
```

<210> SEQ ID NO 8
<211> LENGTH: 112
<212> TYPE: PRT
<213> ORGANISM: Artificial Sequence
<220> FEATURE:
<223> OTHER INFORMATION: Synthetic

<400> SEQUENCE: 8

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Arg Leu Val His Ser
            20                  25                  30
```

His Gly Lys Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Ala His Phe Pro Tyr Thr Phe Gly Gly Gly Thr Lys Val Glu Ile Lys
            100                 105                 110

<210> SEQ ID NO 9
<211> LENGTH: 112
<212> TYPE: PRT
<213> ORGANISM: Artificial Sequence
<220> FEATURE:
<223> OTHER INFORMATION: Synthetic

<400> SEQUENCE: 9

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

His Gly Lys Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Ala His Phe Pro Tyr Thr Phe Gly Gly Gly Thr Lys Val Glu Ile Lys
            100                 105                 110

<210> SEQ ID NO 10
<211> LENGTH: 16
<212> TYPE: PRT
<213> ORGANISM: Artificial Sequence
<220> FEATURE:
<223> OTHER INFORMATION: Synthetic

<400> SEQUENCE: 10

Arg Ser Ser Gln Ser Leu Val His Ser His Gly Lys Thr Tyr Leu His
1               5                   10                  15

<210> SEQ ID NO 11
<211> LENGTH: 2850
<212> TYPE: DNA
<213> ORGANISM: Artificial Sequence
<220> FEATURE:
<223> OTHER INFORMATION: Synthetic

<400> SEQUENCE: 11
aagcttgccg ccaccatggg atggagctgt atcatcctct tcttggtagc aacagctaca      60
ggtaaggggc tcacagtagc aggcttgagg tctggacata tatatgggtg acaatgacat     120
ccactttgcc tttctctcca caggtgtcca ctcccaggtc cagctggtgc aatctggagc     180
cgaagtgaag aagcctgggt cctcagtgaa ggtgtcctgt aaggcttctg gatatacctt     240
cactgactac tacatgaact gggtgaggca ggcccctgga cagggccttg agtggattgg     300

```
agatattaat cctaaccgcg gtggaactac ttacaaccag aagttcaagg gcagggtgac    360
catcactgtg gacaagtcca ccagcacagc ctacatggaa ctcagcagcc tgagatctga    420
ggacaccgca gtctattact gtgcaagtta ctacgccgtg ggctactggg gccaaggcac    480
cactgtgaca gtctcctcag gtgagtcctt acaacctctc tcttctattc agcttaaata    540
gattttactg catttgttgg gggggaaatg tgtgtatctg aatttcaggt catgaaggac    600
tagggacacc ttgggagtca gaaagggtca ttggagcccc gggctgatgc agacagacat    660
cctcagctcc cagacttcat ggccagagat ttataggatc cagctttctg gggcaggcca    720
ggcctgacct tggctggggg cagggagggg gctaaggtga cgcaggtggc gccagccagg    780
tgcacaccca atgcccatga gcccagacac tggaccctgc atggaccatc gcggatagac    840
aagaaccgag gggcctctgc gccctgggcc cagctctgtc ccacaccgcg gtcacatggc    900
accacctctc ttgcagcttc caccaagggc ccatccgtct tccccctggc gccctgctcc    960
agatcgacct ccgagagcac agccgccctg ggctgcctgg tcaaggacta cttccccgaa   1020
ccggtgacgg tgtcgtggaa ctcaggcgcc ctgaccagcg gcgtgcacac cttcccggct   1080
gtcctacagt cctcaggact ctactccctc agcagcgtgg tgaccgtgcc ctccagcagc   1140
ttgggcacga agacctacac ctgcaacgta gatcacaagc ccagcaacac caaggtggac   1200
aagagagttg gtgagaggcc agcacaggga gggagggtgt ctgctggaag ccaggctcag   1260
ccctcctgcc tggacgcacc ccggctgtgc agccccagcc cagggcagca aggcatgccc   1320
catctgtctc ctcacccgga ggcctctgac cacccactc atgctcaggg agagggtctt    1380
ctggattttt ccaccaggct ccgggcagcc acaggctgga tgcccctacc ccaggccctg   1440
cgcatacagg ggcaggtgct gcgctcgac ctgccaagag ccatatccgg gaggaccctg     1500
cccctgacct aagcccaccc caaaggccaa actctccact ccctcagctc agacaccttc   1560
tctcctccca gatcgatctg agtaactccc aatcttctct ctgcagagtc caaatatggt   1620
cccccgtgtc ccccatgccc aggtaagcca acccaggcct cgcctccag ctcaaggcgg    1680
gacaggtgcc ctagagtagc ctgcatccag ggacaggccc cagccgggtg ctgacgcatc   1740
cacctccatc tcttcctcag cacctgagtt cctggggga ccatcagtct tcctgttccc    1800
cccaaaaccc aaggacactc tcatgatctc ccggacccct gaggtcacgt gcgtggtggt   1860
ggacgtgagc caggaagacc ccgaggtcca gttcaactgg tacgtggatg gcgtggaggt   1920
gcataatgcc aagacaaagc cgcgggagga gcagttcaac agcacgtacc gtgtggtcag   1980
cgtcctcacc gtcctgcacc aggactggct gaacggcaag gagtacaagt gcaaggtctc   2040
caacaaaggc ctcccgtcct ccatcgagaa aaccatctcc aaagccaaag gtgggaccca   2100
cggggtgcga gggccacatg gacagaggtc agctcggccc accctctgcc ctgggagtga   2160
ccgctgtgcc aacctctgtc cctacagggc agccccgaga gccacaggtg tacaccctgc   2220
ccccatccca ggaggagatg accaagaacc aggtcagcct gacctgcctg gtcaaaggct   2280
tctaccccag cgacatcgcc gtggagtggg agagcaatgg gcagccggag aacaactaca   2340
agaccacgcc tcccgtcctc gattccgacg gctccttctt cctctacagc aggctaaccg   2400
tggacaagag caggtggcag gaggggaatg tcttctcatg ctccgtgatg catgaggctc   2460
tgcacaacca ctacacacag aagagcctct ccctgtctct gggttgatga gtgccagggc   2520
cggcaagccc ccgctccccg ggctctcggg gtcgcgcgag gatgcttggc acgtaccccg   2580
tctacatact tcccaggcac ccagcatgga aataaagcac ccaccactgc cctgggcccc   2640
```

```
tgtgagactg tgatggttct ttccacgggt caggccgagt ctgaggcctg agtgacatga       2700 ggaggcaga gcgggtccca ctgtccccac actggcccag gctgtgcagg tgtgcctggg       2760
ccgcctaggg tggggctcag ccaggggctg ccctcggcag ggtggggat ttgccagcgt        2820 ggccctccct ccagcagcag gtacctcgag                                        2850

<210> SEQ ID NO 12
<211> LENGTH: 2067
<212> TYPE: DNA
<213> ORGANISM: Artificial Sequence
<220> FEATURE:
<223> OTHER INFORMATION: Synthetic

<400> SEQUENCE: 12
aagcttgccg ccaccatggg atggagctgt atcatcctct tcttggtagc aacagctaca         60 ggtaagggc tcacagtagc aggcttgagg tctggacata tatatgggtg acaatgacat         120
ccactttgcc tttctctcca caggtgtcca ctccgatatc gtgatgaccc aaactccact        180
ctccctgcct gtcaccccctg agagcccgc ctccatctct tgcagatcta gtcagaggct        240
tgtgcacagt catggaaaaa cctatctgca ttggtacctg cagaagccag gccagtctcc       300
acagctcctg atctacaaag tttccaaccg gttttctggg gtcccagaca ggttcagtgg       360
cagtggatca gggacagatt tcacactcaa gatcagcaga gtggaggctg aggatgtggg       420
agtttatttc tgttctcaaa ctgcacattt tccctcacacc ttcggagggg ggaccaaggt       480
ggaaatcaaa cgtgagtaga atttaaactt tgcttcctca gttggatcca ctagtccagt       540
gtggtggaat tctaaactct gaggggggtcg atgacgtgg ccattctttg cctaaagcat       600
tgagtttact gcaaggtcag aaaagcatgc aaagccctca gaatggctgc aaagagctcc      660
aacaaaacaa tttagaactt tattaaggaa taggggggaag ctaggaagaa actcaaaaca      720
tcaagatttt aaatacgctt cttggtctcc ttgctataat tatctgggat aagcatgctg      780
ttttctgtct gtccctaaca tgccctgtga ttatccgcaa acaacacacc caagggcaga      840
actttgttac ttaaacacca tcctgttttgc ttcttttcctc aggaactgtg gctgcaccat     900
ctgtcttcat cttcccgcca tctgatgagc agttgaaatc tggaactgcc tctgttgtgt     960
gcctgctgaa taacttctat cccagagagg ccaaagtaca gtggaaggtg gataacgccc     1020
tccaatcggg taactcccag gagagtgtca cagagcagga cagcaaggac agcacctaca     1080
gcctcagcag caccctgacg ctgagcaaag cagactacga gaaacacaaa gtctacgcct     1140
gcgaagtcac ccatcagggc ctgagctcgc ccgtcacaaa gagcttcaac aggggagagt      1200
gttagaggga gaagtgcccc cacctgctcc tcagttccag cctgaccccc tcccatcctt     1260
tggcctctga ccctttttcc acaggggacc taccccctatt gcggtcctcc agctcatctt    1320
tcacctcacc cccctcctcc tccttggctt taattatgct aatgttggag gagaatgaat    1380
aaataaagtg aatcttttgca cctgtggttt ctctctttcc tcatttaata attattatct   1440
gttgttttac caactactca atttctctta taagggacta aatatgtagt catcctaagg    1500
cgcataacca tttataaaaa tcatccttca ttctatttta ccctatcatc ctctgcaaga   1560
cagtcctccc tcaaacccac aagccttctg tcctcacagt ccctgggcc atggtaggag    1620 agacttgctt ccttgttttc ccctcctcag caagccctca tagtccttttt taagggtgac   1680 aggtcttaca gtcatatatc ctttgattca attcctgag aatcaaccaa agcaaatttt    1740
tcaaaagaag aaacctgcta taagagaat cattcattgc aacatgatat aaaataacaa    1800
cacaataaaa gcaattaaat aaacaaacaa tagggaaatg tttaagttca tcatggtact   1860
```

```
tagacttaat ggaatgtcat gccttattta cattttaaa caggtactga gggactcctg      1920
tctgccaagg gccgtattga gtactttcca caacctaatt taatccacac tatactgtga      1980
gattaaaaac attcattaaa atgttgcaaa ggttctataa agctgagaga caaatatatt      2040
ctataactca gcaatcccac ttctaga                                          2067
```

<210> SEQ ID NO 13
<211> LENGTH: 2067
<212> TYPE: DNA
<213> ORGANISM: Artificial Sequence
<220> FEATURE:
<223> OTHER INFORMATION: Synthetic

<400> SEQUENCE: 13

```
aagcttgccg ccaccatggg atggagctgt atcatcctct tcttggtagc aacagctaca        60 ggtaagggc tcacagtagc aggcttgagg tctggacata tatatgggtg acaatgacat       120
ccactttgcc tttctctcca caggtgtcca ctccgatatc gtgatgaccc aaactccact       180
ctccctgcct gtcaccctg gagagcccgc ctccatctct tgcagatcta gtcagagcct       240
tgtgcacagt catggaaaaa cctatctgca ttggtacctg cagaagccag gccagtctcc       300
acagctcctg atctacaaag ttttccaaccg gttttctggg gtcccagaca ggttcagtgg       360
cagtggatca gggacagatt tcacactcaa gatcagcaga gtggaggctg aggatgtggg       420
agtttatttc tgttctcaaa ctgcacattt tcctacacc ttcggagggg ggaccaaggt       480
ggaaatcaaa cgtgagtaga atttaaactt gcttcctca gttggatcca ctagtccagt       540
gtggtggaat tctaaactct gagggggtcg gatgacgtgg ccattctttg cctaaagcat       600
tgagtttact gcaaggtcag aaaagcatgc aaagccctca gaatggctgc aaagagctcc       660
aacaaaacaa tttagaactt tattaaggaa taggggggaag ctaggaagaa actcaaaaca       720
tcaagatttt aaatacgctt cttggtctcc ttgctataat tatctgggat aagcatgctg       780
ttttctgtct gtccctaaca tgccctgtga ttatccgcaa acaacacacc caagggcaga       840
actttgttac ttaaacacca tcctgtttgc ttctttcctc aggaactgtg gctgcaccat       900
ctgtcttcat cttcccgcca tctgatgagc agttgaaatc tggaactgcc tctgttgtgt       960
gcctgctgaa taacttctat cccagagagg ccaaagtaca gtggaaggtg gataacgccc      1020
tccaatcggg taactcccag gagagtgtca cagagcagga cagcaaggac agcacctaca      1080
gcctcagcag caccctgacg ctgagcaaag cagactacga aaacacaaa gtctacgcct      1140 gcgaagtcac ccatcagggc ctgagctcgc ccgtcacaaa gagcttcaac aggggagagt      1200
gttagaggga gaagtgcccc cacctgctcc tcagttccag cctgaccccc tcccatcctt      1260
tggcctctga ccctttttcc acaggggacc taccctatt gcggtcctcc agctcatctt      1320
tcacctcacc cccctcctcc tccttggctt taattatgct aatgttggag gagaatgaat      1380
aaataaagtg aatctttgca cctgtggttt ctctctttcc tcatttaata attattatct      1440
gttgttttac caactactca atttctctta taagggacta aatatgtagt catcctaagg      1500
cgcataacca tttataaaaa tcatccttca ttctatttta ccctatcatc ctctgcaaga      1560
cagtcctccc tcaaacccac aagccttctg tcctcacagt ccctgggcc atggtaggag      1620 agacttgctt ccttgttttc ccctcctcag caagccctca tagtcctttt taagggtgac      1680
aggtcttaca gtcatatatc ctttgattca attccctgag aatcaaccaa agcaaatttt      1740
tcaaaagaag aaacctgcta taagagaat cattcattgc aacatgatat aaaataacaa      1800
```

```
cacaataaaa gcaattaaat aaacaaacaa tagggaaatg tttaagttca tcatggtact    1860
tagacttaat ggaatgtcat gccttattta cattttaaa caggtactga gggactcctg    1920
tctgccaagg gccgtattga gtactttcca caacctaatt taatccacac tatactgtga    1980
gattaaaaac attcattaaa atgttgcaaa ggttctataa agctgagaga caaatatatt    2040
ctataactca gcaatcccac ttctaga                                        2067
```

```
<210> SEQ ID NO 14
<211> LENGTH: 98
<212> TYPE: PRT
<213> ORGANISM: Artificial Sequence
<220> FEATURE:
<223> OTHER INFORMATION: Synthetic

<400> SEQUENCE: 14

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val
```

```
<210> SEQ ID NO 15
<211> LENGTH: 12
<212> TYPE: PRT
<213> ORGANISM: Artificial Sequence
<220> FEATURE:
<223> OTHER INFORMATION: Synthetic

<400> SEQUENCE: 15

Glu Ser Lys Tyr Gly Pro Pro Cys Pro Pro Cys Pro
1               5                   10
```

```
<210> SEQ ID NO 16
<211> LENGTH: 110
<212> TYPE: PRT
<213> ORGANISM: Artificial Sequence
<220> FEATURE:
<223> OTHER INFORMATION: Synthetic

<400> SEQUENCE: 16

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
```

```
                           85                  90                  95

Gly Leu Pro Ser Ser Ile Glu Lys Thr Ile Ser Lys Ala Lys
                100                 105                 110

<210> SEQ ID NO 17
<211> LENGTH: 106
<212> TYPE: PRT
<213> ORGANISM: Artificial Sequence
<220> FEATURE:
<223> OTHER INFORMATION: Synthetic

<400> SEQUENCE: 17

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly
                100                 105

<210> SEQ ID NO 18
<211> LENGTH: 107
<212> TYPE: PRT
<213> ORGANISM: Artificial Sequence
<220> FEATURE:
<223> OTHER INFORMATION: Synthetic

<400> SEQUENCE: 18

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 19
<211> LENGTH: 441
<212> TYPE: PRT
<213> ORGANISM: Artificial Sequence
<220> FEATURE:
<223> OTHER INFORMATION: Synthetic

<400> SEQUENCE: 19

Met Ala Glu Pro Arg Gln Glu Phe Glu Val Met Glu Asp His Ala Gly
1               5                   10                  15
```

```
Thr Tyr Gly Leu Gly Asp Arg Lys Asp Gln Gly Gly Tyr Thr Met His
            20                  25                  30
Gln Asp Gln Glu Gly Asp Thr Asp Ala Gly Leu Lys Glu Ser Pro Leu
        35                  40                  45
Gln Thr Pro Thr Glu Asp Gly Ser Glu Pro Gly Ser Glu Thr Ser
 50                  55                  60
Asp Ala Lys Ser Thr Pro Thr Ala Glu Asp Val Thr Ala Pro Leu Val
 65                  70                  75                  80
Asp Glu Gly Ala Pro Gly Lys Gln Ala Ala Gln Pro His Thr Glu
                 85                  90                  95
Ile Pro Glu Gly Thr Thr Ala Glu Glu Ala Gly Ile Gly Asp Thr Pro
                100                 105                 110
Ser Leu Glu Asp Glu Ala Ala Gly His Val Thr Gln Ala Arg Met Val
            115                 120                 125
Ser Lys Ser Lys Asp Gly Thr Gly Ser Asp Asp Lys Lys Ala Lys Gly
        130                 135                 140
Ala Asp Gly Lys Thr Lys Ile Ala Thr Pro Arg Gly Ala Ala Pro Pro
145                 150                 155                 160
Gly Gln Lys Gly Gln Ala Asn Ala Thr Arg Ile Pro Ala Lys Thr Pro
                165                 170                 175
Pro Ala Pro Lys Thr Pro Ser Ser Gly Glu Pro Pro Lys Ser Gly
            180                 185                 190
Asp Arg Ser Gly Tyr Ser Ser Pro Gly Ser Pro Gly Thr Pro Gly Ser
            195                 200                 205
Arg Ser Arg Thr Pro Ser Leu Pro Thr Pro Pro Thr Arg Glu Pro Lys
210                 215                 220
Lys Val Ala Val Val Arg Thr Pro Pro Lys Ser Pro Ser Ser Ala Lys
225                 230                 235                 240
Ser Arg Leu Gln Thr Ala Pro Val Pro Met Pro Asp Leu Lys Asn Val
                245                 250                 255
Lys Ser Lys Ile Gly Ser Thr Glu Asn Leu Lys His Gln Pro Gly Gly
            260                 265                 270
Gly Lys Val Gln Ile Ile Asn Lys Lys Leu Asp Leu Ser Asn Val Gln
        275                 280                 285
Ser Lys Cys Gly Ser Lys Asp Asn Ile Lys His Val Pro Gly Gly Gly
    290                 295                 300
Ser Val Gln Ile Val Tyr Lys Pro Val Asp Leu Ser Lys Val Thr Ser
305                 310                 315                 320
Lys Cys Gly Ser Leu Gly Asn Ile His His Lys Pro Gly Gly Gly Gln
                325                 330                 335
Val Glu Val Lys Ser Glu Lys Leu Asp Phe Lys Asp Arg Val Gln Ser
            340                 345                 350
Lys Ile Gly Ser Leu Asp Asn Ile Thr His Val Pro Gly Gly Gly Asn
        355                 360                 365
Lys Lys Ile Glu Thr His Lys Leu Thr Phe Arg Glu Asn Ala Lys Ala
    370                 375                 380
Lys Thr Asp His Gly Ala Glu Ile Val Tyr Lys Ser Pro Val Val Ser
385                 390                 395                 400
Gly Asp Thr Ser Pro Arg His Leu Ser Asn Val Ser Ser Thr Gly Ser
                405                 410                 415
Ile Asp Met Val Asp Ser Pro Gln Leu Ala Thr Leu Ala Asp Glu Val
            420                 425                 430
```

Ser Ala Ser Leu Ala Lys Gln Gly Leu
        435                 440

<210> SEQ ID NO 20
<211> LENGTH: 115
<212> TYPE: PRT
<213> ORGANISM: Artificial Sequence
<220> FEATURE:
<223> OTHER INFORMATION: Synthetic

<400> SEQUENCE: 20

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Ile
        35                  40                  45

Gly Asp Ile Asn Pro Asn Arg Gly Gly Thr Thr Tyr Asn Gln Lys Phe
    50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Tyr Tyr Ala Val Gly Tyr Trp Gly Gln Gly Thr Thr Val Thr
            100                 105                 110

Val Ser Ser
        115

<210> SEQ ID NO 21
<211> LENGTH: 115
<212> TYPE: PRT
<213> ORGANISM: Artificial Sequence
<220> FEATURE:
<223> OTHER INFORMATION: Synthetic

<400> SEQUENCE: 21

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Ile
        35                  40                  45

Gly Asp Ile Asn Pro Asn Arg Gly Gly Thr Thr Tyr Asn Gln Lys Phe
    50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Tyr Tyr Ala Val Gly Tyr Trp Gly Gln Gly Thr Thr Val Thr
            100                 105                 110

Val Ser Ser
        115

<210> SEQ ID NO 22
<211> LENGTH: 219
<212> TYPE: PRT
<213> ORGANISM: Artificial Sequence
<220> FEATURE:
<223> OTHER INFORMATION: Synthetic -continued

<400> SEQUENCE: 22

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Arg Leu Val His Ser
            20                  25                  30

His Gly Lys Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Ala His Phe Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 23
<211> LENGTH: 219
<212> TYPE: PRT
<213> ORGANISM: Artificial Sequence
<220> FEATURE:
<223> OTHER INFORMATION: Synthetic

<400> SEQUENCE: 23

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

His Gly Lys Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95

Ala His Phe Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
```

-continued

```
                130                 135                 140
Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
                210                 215

<210> SEQ ID NO 24
<211> LENGTH: 441
<212> TYPE: PRT
<213> ORGANISM: Artificial Sequence
<220> FEATURE:
<223> OTHER INFORMATION: Synthetic

<400> SEQUENCE: 24

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
                20                  25                  30

Tyr Met Asn Trp Val Arg Gln Ala Pro Gly Gln Gly Leu Glu Trp Ile
                35                  40                  45

Gly Asp Ile Asn Pro Asn Arg Gly Gly Thr Thr Tyr Asn Gln Lys Phe
50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Tyr Tyr Ala Val Gly Tyr Trp Gly Gln Gly Thr Thr Val Thr
                100                 105                 110

Val Ser Ser Ala Ser Thr Lys Gly Pro Ser Val Phe Pro Leu Ala Pro
                115                 120                 125

Cys Ser Arg Ser Thr Ser Glu Ser Thr Ala Ala Leu Gly Cys Leu Val
                130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Lys Thr Tyr Thr Cys Asn Val Asp His Lys Pro Ser Asn Thr Lys
                195                 200                 205

Val Asp Lys Arg Val Glu Ser Lys Tyr Gly Pro Pro Cys Pro Pro Cys
                210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
                260                 265                 270

Tyr Val Asp Gly Val Glu Val His Asn Ala Lys Thr Lys Pro Arg Glu
```

```
              275                 280                 285
Glu Gln Phe Asn Ser Thr Tyr Arg Val Val Ser Val Leu Thr Val Leu
        290                 295                 300
His Gln Asp Trp Leu Asn Gly Lys Glu Tyr Lys Cys Lys Val Ser Asn
305                 310                 315                 320
Lys Gly Leu Pro Ser Ser Ile Glu Lys Thr Ile Ser Lys Ala Lys Gly
                325                 330                 335
Gln Pro Arg Glu Pro Gln Val Tyr Thr Leu Pro Pro Ser Gln Glu Glu
            340                 345                 350
Met Thr Lys Asn Gln Val Ser Leu Thr Cys Leu Val Lys Gly Phe Tyr
                355                 360                 365
Pro Ser Asp Ile Ala Val Glu Trp Glu Ser Asn Gly Gln Pro Glu Asn
370                 375                 380
Asn Tyr Lys Thr Thr Pro Pro Val Leu Asp Ser Asp Gly Ser Phe Phe
385                 390                 395                 400
Leu Tyr Ser Arg Leu Thr Val Asp Lys Ser Arg Trp Gln Glu Gly Asn
                405                 410                 415
Val Phe Ser Cys Ser Val Met His Glu Ala Leu His Asn His Tyr Thr
                420                 425                 430
Gln Lys Ser Leu Ser Leu Ser Leu Gly
                435                 440

<210> SEQ ID NO 25
<211> LENGTH: 441
<212> TYPE: PRT
<213> ORGANISM: Artificial Sequence
<220> FEATURE:
<223> OTHER INFORMATION: Synthetic

<400> SEQUENCE: 25

Gln Val Gln Leu Val Gln Ser Gly Ala Glu Val Lys Lys Pro Gly Ser
1               5                   10                  15
Ser Val Lys Val Ser Cys Lys Ala Ser Gly Tyr Thr Phe Thr Asp Tyr
                20                  25                  30
Tyr Met Asn Trp Val Arg Gln Ala Pro Gly Gln Gly Leu Glu Trp Ile
            35                  40                  45
Gly Asp Ile Asn Pro Asn Arg Gly Gly Thr Thr Tyr Asn Gln Lys Phe
        50                  55                  60
Lys Gly Arg Val Thr Ile Thr Val Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Ser Tyr Tyr Ala Val Gly Tyr Trp Gly Gln Gly Thr Thr Val Thr
                100                 105                 110
Val Ser Ser Ala Ser Thr Lys Gly Pro Ser Val Phe Pro Leu Ala Pro
            115                 120                 125
Cys Ser Arg Ser Thr Ser Glu Ser Thr Ala Ala Leu Gly Cys Leu Val
        130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Lys Thr Tyr Thr Cys Asn Val Asp His Lys Pro Ser Asn Thr Lys
```

```
            195                 200                 205
Val Asp Lys Arg Val Glu Ser Lys Tyr Gly Pro Pro Cys Pro Pro Cys
210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly
        435                 440

<210> SEQ ID NO 26
<211> LENGTH: 442
<212> TYPE: PRT
<213> ORGANISM: Artificial Sequence
<220> FEATURE:
<223> OTHER INFORMATION: Synthetic

<400> SEQUENCE: 26

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Ile
        35                  40                  45

Gly Asp Ile Asn Pro Asn Arg Gly Gly Thr Thr Tyr Asn Gln Lys Phe
    50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Tyr Tyr Ala Val Gly Tyr Trp Gly Gln Gly Thr Thr Val Thr
            100                 105                 110

Val Ser Ser Ala Ser Thr Lys Gly Pro Ser Val Phe Pro Leu Ala Pro
```

```
            115                 120                 125
Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
    210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly Lys
        435                 440

<210> SEQ ID NO 27
<211> LENGTH: 445
<212> TYPE: PRT
<213> ORGANISM: Artificial Sequence
<220> FEATURE:
<223> OTHER INFORMATION: Synthetic

<400> SEQUENCE: 27

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Ile
```

```
            35                  40                  45
Gly Asp Ile Asn Pro Asn Arg Gly Thr Thr Tyr Asn Gln Lys Phe
 50                  55                  60

Lys Gly Arg Val Thr Ile Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Ser Tyr Tyr Ala Val Gly Tyr Trp Gly Gln Gly Thr Thr Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 28
```

```
<211> LENGTH: 445
<212> TYPE: PRT
<213> ORGANISM: Artificial Sequence
<220> FEATURE:
<223> OTHER INFORMATION: Synthetic

<400> SEQUENCE: 28
```

| | | | | | | | | | | | | | | | |
|---|---|---|---|---|---|---|---|---|---|---|---|---|---|---|---|
| Glu | Val | Gln | Leu | Val | Gln | Ser | Gly | Ala | Glu | Val | Lys | Lys | Pro | Gly | Ser |
| 1 | | | | 5 | | | | | 10 | | | | | 15 | |
| Ser | Val | Lys | Val | Ser | Cys | Lys | Ala | Ser | Gly | Tyr | Thr | Phe | Thr | Asp | Tyr |
| | | | 20 | | | | | 25 | | | | | 30 | | |
| Tyr | Met | Asn | Trp | Val | Arg | Gln | Ala | Pro | Gly | Gln | Gly | Leu | Glu | Trp | Ile |
| | | 35 | | | | | 40 | | | | | 45 | | | |
| Gly | Asp | Ile | Asn | Pro | Asn | Arg | Gly | Gly | Thr | Thr | Tyr | Asn | Gln | Lys | Phe |
| | 50 | | | | | 55 | | | | | 60 | | | | |
| Lys | Gly | Arg | Val | Thr | Ile | Thr | Val | Asp | Lys | Ser | Thr | Ser | Thr | Ala | Tyr |
| 65 | | | | | 70 | | | | | 75 | | | | | 80 |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Ala | Ser | Tyr | Tyr | Ala | Val | Gly | Tyr | Trp | Gly | Gln | Gly | Thr | Thr | Val | Thr |
| | | | 100 | | | | | 105 | | | | | 110 | | |
| Val | Ser | Ser | Ala | Ser | Thr | Lys | Gly | Pro | Ser | Val | Phe | Pro | Leu | Ala | Pro |
| | | 115 | | | | | 120 | | | | | 125 | | | |
| Ser | Ser | Lys | Ser | Thr | Ser | Gly | Gly | Thr | Ala | Ala | Leu | Gly | Cys | Leu | Val |
| | 130 | | | | | 135 | | | | | 140 | | | | |
| Lys | Asp | Tyr | Phe | Pro | Glu | Pro | Val | Thr | Val | Ser | Trp | Asn | Ser | Gly | Ala |
| 145 | | | | | 150 | | | | | 155 | | | | | 160 |
| Leu | Thr | Ser | Gly | Val | His | Thr | Phe | Pro | Ala | Val | Leu | Gln | Ser | Ser | Gly |
| | | | | 165 | | | | | 170 | | | | | 175 | |
| Leu | Tyr | Ser | Leu | Ser | Ser | Val | Val | Thr | Val | Pro | Ser | Ser | Ser | Leu | Gly |
| | | | 180 | | | | | 185 | | | | | 190 | | |
| Thr | Gln | Thr | Tyr | Ile | Cys | Asn | Val | Asn | His | Lys | Pro | Ser | Asn | Thr | Lys |
| | | 195 | | | | | 200 | | | | | 205 | | | |
| Val | Asp | Lys | Lys | Val | Glu | Pro | Lys | Ser | Cys | Asp | Lys | Thr | His | Thr | Cys |
| | 210 | | | | | 215 | | | | | 220 | | | | |
| Pro | Pro | Cys | Pro | Ala | Pro | Glu | Leu | Leu | Gly | Gly | Pro | Ser | Val | Phe | Leu |
| 225 | | | | | 230 | | | | | 235 | | | | | 240 |
| Phe | Pro | Pro | Lys | Pro | Lys | Asp | Thr | Leu | Met | Ile | Ser | Arg | Thr | Pro | Glu |
| | | | | 245 | | | | | 250 | | | | | 255 | |
| Val | Thr | Cys | Val | Val | Val | Asp | Val | Ser | His | Glu | Asp | Pro | Glu | Val | Lys |
| | | | 260 | | | | | 265 | | | | | 270 | | |
| Phe | Asn | Trp | Tyr | Val | Asp | Gly | Val | Glu | Val | His | Asn | Ala | Lys | Thr | Lys |
| | | 275 | | | | | 280 | | | | | 285 | | | |
| Pro | Arg | Glu | Glu | Gln | Tyr | Gly | Ser | Thr | Tyr | Arg | Val | Val | Ser | Val | Leu |
| | 290 | | | | | 295 | | | | | 300 | | | | |
| Thr | Val | Leu | His | Gln | Asp | Trp | Leu | Asn | Gly | Lys | Glu | Tyr | Lys | Cys | Lys |
| 305 | | | | | 310 | | | | | 315 | | | | | 320 |
| Val | Ser | Asn | Lys | Ala | Leu | Pro | Ala | Pro | Ile | Glu | Lys | Thr | Ile | Ser | Lys |
| | | | | 325 | | | | | 330 | | | | | 335 | |
| Ala | Lys | Gly | Gln | Pro | Arg | Glu | Pro | Gln | Val | Tyr | Thr | Leu | Pro | Pro | Ser |
| | | | 340 | | | | | 345 | | | | | 350 | | |
| Arg | Glu | Glu | Met | Thr | Lys | Asn | Gln | Val | Ser | Leu | Thr | Cys | Leu | Val | Lys |
| | | 355 | | | | | 360 | | | | | 365 | | | |
| Gly | Phe | Tyr | Pro | Ser | Asp | Ile | Ala | Val | Glu | Trp | Glu | Ser | Asn | Gly | Gln |
| | 370 | | | | | 375 | | | | | 380 | | | | |

```
Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 29
<211> LENGTH: 442
<212> TYPE: PRT
<213> ORGANISM: Artificial Sequence
<220> FEATURE:
<223> OTHER INFORMATION: Synthetic

<400> SEQUENCE: 29

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
                20                  25                  30

Tyr Met Asn Trp Val Arg Gln Ala Pro Gly Gln Gly Leu Glu Trp Ile
            35                  40                  45

Gly Asp Ile Asn Pro Asn Arg Gly Gly Thr Thr Tyr Asn Gln Lys Phe
        50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Tyr Tyr Ala Val Gly Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300
```

```
His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
            325                 330                 335

Gln Pro Arg Glu Pro Gln Val Tyr Thr Leu Pro Pro Ser Gln Glu Glu
        340                 345                 350

Met Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
        370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
            405                 410                 415

Val Phe Ser Cys Ser Val Met His Glu Ala Leu His Asn His Tyr Thr
            420                 425                 430

Gln Lys Ser Leu Ser Leu Ser Leu Gly Lys
            435                 440

<210> SEQ ID NO 30
<211> LENGTH: 408
<212> TYPE: PRT
<213> ORGANISM: Artificial Sequence
<220> FEATURE:
<223> OTHER INFORMATION: Synthetic

<400> SEQUENCE: 30

Arg Gln Ala Pro Gly Gln Gly Leu Glu Trp Ile Gly Asp Ile Asn Pro
1               5                   10                  15

Asn Arg Gly Gly Thr Thr Tyr Asn Gln Lys Phe Lys Gly Arg Val Thr
            20                  25                  30

Ile Thr Val Asp Lys Ser Thr Ser Thr Ala Tyr Met Glu Leu Ser Ser
        35                  40                  45

Leu Arg Ser Glu Asp Thr Ala Val Tyr Tyr Cys Ala Ser Tyr Tyr Ala
    50                  55                  60

Val Gly Tyr Trp Gly Gln Gly Thr Thr Val Thr Val Ser Ser Ala Ser
65                  70                  75                  80

Thr Lys Gly Pro Ser Val Phe Pro Leu Ala Pro Ser Ser Lys Ser Thr
            85                  90                  95

Ser Gly Gly Thr Ala Ala Leu Gly Cys Leu Val Lys Asp Tyr Phe Pro
        100                 105                 110

Glu Pro Val Thr Val Ser Trp Asn Ser Gly Ala Leu Thr Ser Gly Val
    115                 120                 125

His Thr Phe Pro Ala Val Leu Gln Ser Ser Gly Leu Tyr Ser Leu Ser
130                 135                 140

Ser Val Val Thr Val Pro Ser Ser Ser Leu Gly Thr Gln Thr Tyr Ile
145                 150                 155                 160

Cys Asn Val Asn His Lys Pro Ser Asn Thr Lys Val Asp Lys Lys Val
            165                 170                 175

Glu Pro Lys Ser Cys Asp Lys Thr His Thr Cys Pro Pro Cys Pro Ala
        180                 185                 190

Pro Glu Leu Leu Gly Gly Pro Ser Val Phe Leu Phe Pro Pro Lys Pro
    195                 200                 205

Lys Asp Thr Leu Met Ile Ser Arg Thr Pro Glu Val Thr Cys Val Val
210                 215                 220
```

```
Val Asp Val Ser His Glu Asp Pro Glu Val Lys Phe Asn Trp Tyr Val
225                 230                 235                 240

Asp Gly Val Glu Val His Asn Ala Lys Thr Lys Pro Arg Glu Glu Gln
            245                 250                 255

Tyr Asn Ser Thr Tyr Arg Val Val Ser Val Leu Thr Val Leu His Gln
        260                 265                 270

Asp Trp Leu Asn Gly Lys Glu Tyr Lys Cys Lys Val Ser Asn Lys Ala
    275                 280                 285

Leu Pro Ala Pro Ile Glu Lys Thr Ile Ser Lys Ala Lys Gly Gln Pro
290                 295                 300

Arg Glu Pro Gln Val Tyr Thr Leu Pro Pro Ser Arg Glu Glu Met Thr
305                 310                 315                 320

Lys Asn Gln Val Ser Leu Thr Cys Leu Val Lys Gly Phe Tyr Pro Ser
                325                 330                 335

Asp Ile Ala Val Glu Trp Glu Ser Asn Gly Gln Pro Glu Asn Asn Tyr
            340                 345                 350

Lys Thr Thr Pro Pro Val Leu Asp Ser Asp Gly Ser Phe Phe Leu Tyr
        355                 360                 365

Ser Lys Leu Thr Val Asp Lys Ser Arg Trp Gln Gln Gly Asn Val Phe
    370                 375                 380

Ser Cys Ser Val Met His Glu Ala Leu His Asn His Tyr Thr Gln Lys
385                 390                 395                 400

Ser Leu Ser Leu Ser Pro Gly Lys
                405

<210> SEQ ID NO 31
<211> LENGTH: 445
<212> TYPE: PRT
<213> ORGANISM: Artificial Sequence
<220> FEATURE:
<223> OTHER INFORMATION: Synthetic

<400> SEQUENCE: 31

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Ile
        35                  40                  45

Gly Asp Ile Asn Pro Asn Arg Gly Gly Thr Thr Tyr Asn Gln Lys Phe
    50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Tyr Tyr Ala Val Gly Tyr Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175
```

Leu Tyr Ser Leu Ser Val Thr Val Pro Ser Ser Leu Gly
                180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Gly Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 32
<211> LENGTH: 23
<212> TYPE: PRT
<213> ORGANISM: Artificial Sequence
<220> FEATURE:
<223> OTHER INFORMATION: Synthetic

<400> SEQUENCE: 32

His Lys Lys Gly Asp Thr Ser Pro Arg His Leu Ser Asn Val Ser Ser
1               5                   10                  15

Thr Gly Ser Ile Asp Lys Lys
            20

<210> SEQ ID NO 33
<211> LENGTH: 8
<212> TYPE: PRT
<213> ORGANISM: Artificial Sequence
<220> FEATURE:
<223> OTHER INFORMATION: Synthetic

<400> SEQUENCE: 33

Gly Asp Thr Ser Pro Arg His Leu 1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic

<400> SEQUENCE: 34

Asp Thr Ser Pro Arg His Leu Ser
1               5

<210> SEQ ID NO 35
<211> LENGTH: 8
<212> TYPE: PRT
<213> ORGANISM: Artificial Sequence
<220> FEATURE:
<223> OTHER INFORMATION: Synthetic

<400> SEQUENCE: 35

Thr Ser Pro Arg His Leu Ser Asn
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

Ser Pro Arg His Leu Ser Asn Val
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic

<400> SEQUENCE: 37

Pro Arg His Leu Ser Asn Val Ser
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic

<400> SEQUENCE: 38

Arg His Leu Ser Asn Val Ser Ser
1               5

<210> SEQ ID NO 39
<211> LENGTH: 8
<212> TYPE: PRT
<213> ORGANISM: Artificial Sequence
<220> FEATURE:
<223> OTHER INFORMATION: Synthetic

<400> SEQUENCE: 39

His Leu Ser Asn Val Ser Ser Thr
1               5

<210> SEQ ID NO 40
<211> LENGTH: 8
<212> TYPE: PRT
<213> ORGANISM: Artificial Sequence
<220> FEATURE:
<223> OTHER INFORMATION: Synthetic

<400> SEQUENCE: 40

Leu Ser Asn Val Ser Ser Thr Gly
1               5

<210> SEQ ID NO 41
<211> LENGTH: 8
<212> TYPE: PRT
<213> ORGANISM: Artificial Sequence
<220> FEATURE:
<223> OTHER INFORMATION: Synthetic

<400> SEQUENCE: 41

Ser Asn Val Ser Ser Thr Gly Ser
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic

<400> SEQUENCE: 42

Asn Val Ser Ser Thr Gly Ser Ile
1               5

<210> SEQ ID NO 43
<211> LENGTH: 8
<212> TYPE: PRT
<213> ORGANISM: Artificial Sequence
<220> FEATURE:
<223> OTHER INFORMATION: Synthetic

<400> SEQUENCE: 43

Val Ser Ser Thr Gly Ser Ile Asp
1               5

<210> SEQ ID NO 44
<211> LENGTH: 8
<212> TYPE: PRT
<213> ORGANISM: Artificial Sequence
<220> FEATURE:
<223> OTHER INFORMATION: Synthetic

<400> SEQUENCE: 44

Gly Asp Thr Ser Pro Arg His Leu
1               5

<210> SEQ ID NO 45
<211> LENGTH: 8
<212> TYPE: PRT
<213> ORGANISM: Artificial Sequence
<220> FEATURE:
<223> OTHER INFORMATION: Synthetic

<400> SEQUENCE: 45

Asp Thr Ser Pro Arg His Leu Ser
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic

<400> SEQUENCE: 46

Thr Ser Pro Arg His Leu Ser Asn
1               5

<210> SEQ ID NO 47
<211> LENGTH: 8
<212> TYPE: PRT
<213> ORGANISM: Artificial Sequence
<220> FEATURE:
<223> OTHER INFORMATION: Synthetic

<400> SEQUENCE: 47

Ser Pro Arg His Leu Ser Asn Val
1               5

<210> SEQ ID NO 48
<211> LENGTH: 8
<212> TYPE: PRT
<213> ORGANISM: Artificial Sequence
<220> FEATURE:
<223> OTHER INFORMATION: Synthetic

<400> SEQUENCE: 48

Pro Arg His Leu Ser Asn Val Ser
1               5

<210> SEQ ID NO 49
<211> LENGTH: 8
<212> TYPE: PRT
<213> ORGANISM: Artificial Sequence
<220> FEATURE:
<223> OTHER INFORMATION: Synthetic

<400> SEQUENCE: 49

Arg His Leu Ser Asn Val Ser Ser
1               5

<210> SEQ ID NO 50
<211> LENGTH: 8
<212> TYPE: PRT
<213> ORGANISM: Artificial Sequence
<220> FEATURE:
<223> OTHER INFORMATION: Synthetic

<400> SEQUENCE: 50

His Leu Ser Asn Val Ser Ser Thr
1               5

<210> SEQ ID NO 51
<211> LENGTH: 8
<212> TYPE: PRT
<213> ORGANISM: Artificial Sequence
<220> FEATURE:
<223> OTHER INFORMATION: Synthetic

<400> SEQUENCE: 51

Leu Ser Asn Val Ser Ser Thr Gly
1               5

```
<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

Ser Asn Val Ser Ser Thr Gly Ser
1               5

<210> SEQ ID NO 53
<211> LENGTH: 8
<212> TYPE: PRT
<213> ORGANISM: Artificial Sequence
<220> FEATURE:
<223> OTHER INFORMATION: Synthetic

<400> SEQUENCE: 53

Asn Val Ser Ser Thr Gly Ser Ile
1               5

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Val Ser Ser Thr Gly Ser Ile Asp
1               5

<210> SEQ ID NO 55
<211> LENGTH: 8
<212> TYPE: PRT
<213> ORGANISM: Artificial Sequence
<220> FEATURE:
<223> OTHER INFORMATION: Synthetic

<400> SEQUENCE: 55

Pro Arg His Leu Ser Asn Val Ser
1               5

<210> SEQ ID NO 56
<211> LENGTH: 8
<212> TYPE: PRT
<213> ORGANISM: Artificial Sequence
<220> FEATURE:
<223> OTHER INFORMATION: Synthetic

<400> SEQUENCE: 56

Pro Arg His Leu Ser Asn Val Ser
1               5

<210> SEQ ID NO 57
<211> LENGTH: 8
<212> TYPE: PRT
<213> ORGANISM: Artificial Sequence
<220> FEATURE:
<223> OTHER INFORMATION: Synthetic

<400> SEQUENCE: 57

Ala Arg His Leu Ser Asn Val Ser
1               5

<210> SEQ ID NO 58
```

```
<211> LENGTH: 8
<212> TYPE: PRT
<213> ORGANISM: Artificial Sequence
<220> FEATURE:
<223> OTHER INFORMATION: Synthetic

<400> SEQUENCE: 58

Pro Ala His Leu Ser Asn Val Ser
1               5

<210> SEQ ID NO 59
<211> LENGTH: 8
<212> TYPE: PRT
<213> ORGANISM: Artificial Sequence
<220> FEATURE:
<223> OTHER INFORMATION: Synthetic

<400> SEQUENCE: 59

Pro Arg Ala Leu Ser Asn Val Ser
1               5

<210> SEQ ID NO 60
<211> LENGTH: 8
<212> TYPE: PRT
<213> ORGANISM: Artificial Sequence
<220> FEATURE:
<223> OTHER INFORMATION: Synthetic

<400> SEQUENCE: 60

Pro Arg His Ala Ser Asn Val Ser
1               5

<210> SEQ ID NO 61
<211> LENGTH: 8
<212> TYPE: PRT
<213> ORGANISM: Artificial Sequence
<220> FEATURE:
<223> OTHER INFORMATION: Synthetic

<400> SEQUENCE: 61

Pro Arg His Leu Ala Asn Val Ser
1               5

<210> SEQ ID NO 62
<211> LENGTH: 8
<212> TYPE: PRT
<213> ORGANISM: Artificial Sequence
<220> FEATURE:
<223> OTHER INFORMATION: Synthetic

<400> SEQUENCE: 62

Pro Arg His Leu Ser Ala Val Ser
1               5

<210> SEQ ID NO 63
<211> LENGTH: 8
<212> TYPE: PRT
<213> ORGANISM: Artificial Sequence
<220> FEATURE:
<223> OTHER INFORMATION: Synthetic

<400> SEQUENCE: 63

Pro Arg His Leu Ser Asn Ala Ser
1               5

<210> SEQ ID NO 64
<211> LENGTH: 8
```

```
<212> TYPE: PRT
<213> ORGANISM: Artificial Sequence
<220> FEATURE:
<223> OTHER INFORMATION: Synthetic

<400> SEQUENCE: 64

Pro Arg His Leu Ser Asn Val Ala
1               5

<210> SEQ ID NO 65
<211> LENGTH: 8
<212> TYPE: PRT
<213> ORGANISM: Artificial Sequence
<220> FEATURE:
<223> OTHER INFORMATION: Synthetic

<400> SEQUENCE: 65

Pro Ala Ala Leu Ser Asn Val Ser
1               5

<210> SEQ ID NO 66
<211> LENGTH: 8
<212> TYPE: PRT
<213> ORGANISM: Artificial Sequence
<220> FEATURE:
<223> OTHER INFORMATION: Synthetic

<400> SEQUENCE: 66

Pro Arg Ala Ala Ser Asn Val Ser
1               5

<210> SEQ ID NO 67
<211> LENGTH: 8
<212> TYPE: PRT
<213> ORGANISM: Artificial Sequence
<220> FEATURE:
<223> OTHER INFORMATION: Synthetic

<400> SEQUENCE: 67

Pro Ala His Ala Ser Asn Val Ser
1               5

<210> SEQ ID NO 68
<211> LENGTH: 8
<212> TYPE: PRT
<213> ORGANISM: Artificial Sequence
<220> FEATURE:
<223> OTHER INFORMATION: Synthetic

<400> SEQUENCE: 68

Pro Ala Ala Ala Ser Asn Val Ser
1               5

<210> SEQ ID NO 69
<211> LENGTH: 18
<212> TYPE: PRT
<213> ORGANISM: Artificial sequence
<220> FEATURE:
<223> OTHER INFORMATION: Synthetic

<400> SEQUENCE: 69

Gly Asp Thr Ser Pro Arg His Leu Ser Asn Val Ser Ser Thr Gly Ser
1               5                   10                  15

Ile Asp

<210> SEQ ID NO 70
```

```
<211> LENGTH: 18
<212> TYPE: PRT
<213> ORGANISM: Artificial sequence
<220> FEATURE:
<223> OTHER INFORMATION: Synthetic

<400> SEQUENCE: 70

Gly Asp Thr Ser Pro Arg His Leu Ser Asn Val Ser Ser Thr Gly Ser
1               5                   10                  15

Ile Asp
```

HUMANIZED TAU ANTIBODY

INCORPORATION OF SEQUENCE LISTING

The present application contains a Sequence Listing in electronic format. The Sequence Listing is provided as a file entitled "2015-11-20_01147-0003-00US_Sequence_Listing_ST25.txt" created on Nov. 20, 2015, which is 66,510 bytes in size. The information in the electronic format of the sequence listing is incorporated herein by reference in its entirety.

The present invention is related to methods and compositions for the therapeutic and diagnostic use in the treatment of diseases and disorders which are caused by or associated with neurofibrillary tangles. In particular, the invention relates to humanized antibodies, which specifically recognize and bind to phosphorylated pathological protein tau-conformers and to methods and compositions involving said antibodies for the therapeutic and diagnostic use in the treatment of tauopathies including Alzheimer's Disease (AD).

Neurofibrillary tangles and neuropil threads (NTs) are the major neuropathological hallmarks of Alzheimer's Disease (AD). They are composed of the microtubule-associated protein tau that has undergone posttranslational modifications, including phosphorylation, deamidation and isomerization on asparaginyl or aspartyl residues. They originate by the aggregation of hyper-phosphorylated protein tau and its conformers. AD shares this pathology with many neurodegenerative tauopathies, in particularly with specified types of frontotemporal dementia (FTD).

Protein Tau is a freely soluble, "naturally unfolded" protein that binds avidly to microtubules (MTs) to promote their assembly and stability. MTs are of major importance for the cytoskeletal integrity of neurons—and thereby for the proper formation and functioning of neuronal circuits, hence for learning and memory. The binding of tau to MT is controlled by dynamic phosphorylation and de-phosphorylation, as demonstrated mainly in vitro and in non-neuronal cells. Due to the large number of possible phosphorylation sites (>80), the exact contribution of each and the identity of the responsible kinases remain largely undefined in vivo.

In AD brain, tau pathology develops later than, and therefore probably in response to amyloid pathology, which constitutes the essence of the amyloid cascade hypothesis. This is based on and indicated by studies in AD and Down syndrome patients, and is corroborated by studies in transgenic mice with combined amyloid and tau pathology (Lewis et al., 2001; Oddo et al., 2004; Ribe et al., 2005; Muyllaert et al, 2006; 2008; Terwel et al, 2008).

The exact timing of both pathologies in human AD patients as well as mechanisms that link amyloid to tau pathology remain largely unknown, but are proposed to involve activation of neuronal signaling pathways that act on or by GSK3 and cdk5 as the major "tau-kinases" (reviewed by Muyllaert et al, 2006, 2008).

The hypothesis that tauopathy is not an innocent side-effect but a major pathological executor in AD is based on sound genetic, pathological and experimental observations that corroborate each other fully:
- in early-onset familial AD cases that are caused by mutations in amyloid protein precursor (APP) or presenilin, the obligate pathogenic cause is amyloid accumulation, but invariably the pathology comprises collateral tauopathy, identical to that in the late-onset sporadic AD cases;
- severity of cognitive dysfunction and dementia correlates with tauopathy, not with amyloid pathology, exemplified most recently by several clinical phase-1&2 studies that include PIB-PET imaging for amyloid and identify many "false positives": cognitively normal individuals with high brain amyloid load;
- in familial FTD, the tauopathy is provoked by mutant tau and causes neurodegeneration directly, without amyloid pathology;
- in experimental mouse models the cognitive defects caused by amyloid pathology are nearly completely alleviated by the absence of protein tau (Roberson et al, 2007).

The combined arguments support the hypothesis that protein tau is a major player in the cognitive demise in AD and related neurodegenerative tauopathies.

A prominent emerging treatment of AD is by passive immunotherapy with specific mAbs, to clear amyloid peptides and their aggregates that are presumed to be neurotoxic or synapto-toxic.

Immunotherapy targeting tau pathology, as proposed here, is anticipated to counteract the pathological protein tau-conformers that are known or postulated to cause synaptic dysfunction and neurodegeneration. Amyloid pathology caused and intra-neuronal aggregates of hyper-phosphorylated protein tau are proposed to act synergistically in the cognitive and degenerative cascade of pathological events that lead from mild cognitive impairment (MCI) to the severe dementia of AD. The combination of tau-directed medication with amyloid-directed (or any other) medication will therefore constitute the preferred and, substantially more efficacious treatment of AD, as opposed to current mono-therapy.

Other therapeutic approaches that target protein tau are scarce and comprise mainly:
- inhibitors of the kinases that are thought to increase the phosphorylation of tau to pathological levels
- compounds that block the cytoplasmic aggregation of hyper-phosphorylated protein tau.

These approaches suffer various draw-backs of specificity and efficacy, a problem they share with attempts to modify the metabolism of APP and amyloid, all emphasizing the importance of a continuous search for additional treatment options, including immunotherapy against tau.

Practically no efforts have been devoted to define—let alone target—the pathological tau conformers in vivo. In the Aβ42 phase II clinical trial, the tangle pathology did not appear to be well considered nor analyzed in much depth (Nicoll et al., 2003; Masliah et al., 2005). On the other hand, experimental immunotherapy targeting amyloid in a pre-clinical mouse model with combined AD-like pathology demonstrated also an effect on tau pathology although tau aggregates persisted (Oddo et al., 2004).

Some doubts have been cast on the feasibility of approaching intra-cellular protein tau by immunotherapy. These have been countered by the most recent experimental study in a tauopathy mouse model (Asuni et al., 2007). They showed reduction in tangle pathology and functional improvements by vaccination with a protein tau derived phospho-peptide. These data corroborate previous reports of immunotherapy targeting α-synuclein in Parkinson's Disease (PD) and Lewy body disease models (Masliah et al., 2005, 2011) and of superoxide dismutase in an amyotrophic lateral sclerosis (ALS) model (Urushitiani et al., 2007). These diseases are examples wherein intra-cellular proteins lead to synaptic defects and neurodegeneration by as yet not fully understood mechanisms. On the other hand, full-length recombinant protein tau produced in and isolated from bacteria appears not suitable as vaccine, although the adjuvants used, i.e. complete Freunds and pertussis toxin, could have contributed to the negative outcome of that study (Rosenmann et al., 2006).

A Tau epitope that requires the phosphorylation of Ser-409 (pS409) has been used as a marker for a Tau phosphosite that appears early in AD (Jicha et al., 1999). This phosphorylation is protein kinase A (PKA)-dependent, and precedes or coincides with the initial stages of paired helical filament (PHF) formation and the eventual spread of neurofibrillary pathology in affected neurons in early AD cases. In mechanistic studies pS409 was also shown to be a direct determinant for the oligomerization of Tau, a process involved in the assembly of PHF and neurofibrillary tangles (Vanhelmont et al., 2010; Alonso et al., 2008). Furthermore, pS409 reduced the ability of Tau to bind to microtubules (MT) even if not part of the MT-binding domain of Tau, demonstrating that phosphorylation of S409 is also detrimental for Tau-microtubule interaction (Vandebroek et al., 2006). A liposomal vaccine comprising the antigenic peptide Tau 401-418 [pS404/pS409] was shown to induce specific IgG antibodies in wildtype C57BL/6 mice and in Tau-deficient mice (WO2010/115843).

Prolonged therapy in humans with rodent antibodies will result in an antiglobulin immune response which is detectable at about 8-12 days after administration and reaches a peak at about 20-30 days. If such an antiglobulin response is encountered, the treatment must be discontinued after no more than about 10 days and re-iteration of the treatment at a later date is usually precluded because it will lead to renewed and more rapid onset of the secondary antiglobulin response. Although rodent antibodies share a considerable degree of sequence conservation with human antibodies, there are many sequence differences between rodents and human antibodies that are sufficient for the rodent antibodies to be immunogenic in humans.

This problem may be overcome by generating antibodies directly in humans or by the creation of "human", "humanized" (a.k.a. "reshaped" antibodies) or "humaneered" antibodies. Humanized antibodies have variable region amino acid sequences that contains the rodent-derived CDRs spliced into human or human-like framework sequences. Since the specificity of the humanized antibody is provided by the rodent-derived CDRs, their residues are to be used essentially unchanged with only minor modifications being allowable, which do not significantly interfere with the affinity and specificity of the antibody for its target antigen. Framework residues may be derived from any primate or, particularly, from any human variable region or may be a combination thereof and the resultant designed variable region would be considered reshaped.

To maximise the likelihood that affinity will be retained in the reshaped antibody it is important to make a proper selection of the framework region. It is known that the framework sequences serve to hold the CDRs in their correct spatial orientation for interaction with antigen, and that framework residues can sometimes even participate in antigen binding. In order to maintain the affinity of the antibody for its antigen it is advantageous to select human framework sequences that are most similar to the sequences of the rodent frameworks. It then may still be necessary to replace one or more amino acids in the human framework sequence with the corresponding residue in the rodent framework to avoid losses with the affinity. This replacement may be aided by computer modelling.

There is a long existing unmet need for passive and/or active immunotherapies in human patients that work to counteract the pathological protein conformers that are known—or presumed—to cause neurodegenerative disorders, such as the amyloid peptides and their aggregates in AD but also the intra-neuronal aggregates of hyper-phosphorylated protein tau that are as typical for AD as amyloid.

This unmet need was met within the scope of the present invention, which provides novel methods and compositions comprising highly specific and highly effective antibodies, particularly chimeric antibodies including fragments thereof, more particularly partially or fully humanized antibodies including fragments thereof, having the ability to specifically recognize and bind to specific major pathological phospho-epitopes of the tau protein. In particular, the present invention provides specific antibodies against linear and conformational, simple and complex phospho-epitopes on protein tau, particularly on aggregated tau protein that are believed to be responsible for synapto- and neuro-toxicity in tauopathies, including AD.

In one embodiment, the invention relates to an antibody, particularly a monoclonal antibody, particularly a chimeric antibody or a fragment thereof, or a humanized antibody or a fragment thereof, which recognizes and binds to at least one distinct binding site on the Tau protein.

The antibody, particularly the monoclonal antibody, particularly the chimeric or humanized antibodies according to the invention as described in the various embodiments, recognizes and specifically binds to a phospho-epitope on a mammalian, particularly on the human Tau protein or on a fragment thereof, particularly to a phospho-epitope on aggregated Tau protein, particularly to a pathological protein tau conformer, but does not bind to the corresponding unphosphorylated epitope and/or to non-related epitopes, wherein said antibody has a high binding affinity to soluble and insoluble Tau protein, and modulates soluble and insoluble Tau levels, particularly in the brain, particularly with a (a) dissociation constant of at least 100 nM, particularly at least 80 nM, particularly at least 70 nM, particularly at least 50 nM, particularly at least 10 nM, particularly of at least 8 nM, particularly of at least 5 nM, particularly of at least 2 nM, particularly of at least 1 nM, particularly of at least 500 pM, particularly of at least 400 pM, particularly of at least 300 pM, particularly of at least 200 pM, particularly of at least 100 pM, particularly of at least 50 pM and/or (b) an association rate constant of $10^4$ $M^{-1}s^{-1}$ or greater, particularly of between 3-5×$10^4$ $M^{-1}s^{-1}$ or greater, particularly of $10^5$ $M^{-1}s^{-1}$ or greater; particularly of 0.5-9×$10^5$ $M^{-1}s^{-1}$ or greater; particularly of $10^8$ $M^{-1}s^{-1}$ or greater, particularly of 1-4×$10^5$ $M^{-1}s^{-1}$ or greater, particularly of $10^7$ $M^{-1}s^{-1}$ or greater.

In certain embodiments, the present invention relates to an antibody, particularly a monoclonal antibody, particularly a chimeric or humanized antibody according to the invention as described in the various embodiments, which antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes, wherein said antibody has a high binding affinity with a dissociation constant of at least 100 nM and an association rate constant of $10^5$ $M^{-1}s^{-1}$ or greater, particularly a dissociation constant of at least 80 nM and an association rate constant of $10^5$ $M^{-1}s^{-1}$ or greater, particularly a dissociation constant of at least 70 nM and an association rate constant of $10^5$ $M^{-1}s^{-1}$ or greater, particularly a dissociation constant of at least 10 nM and an association rate constant of $10^5$ $M^{-1}s^{-1}$ or greater, particularly a dissociation constant of at least 200 pM and an association rate constant of $10^5$ $M^{-1}s^{-1}$ or greater, particularly a dissociation constant of at least 100 pM and an association rate constant of $10^8$ $M^{-1}s^{-1}$ or greater.

In various embodiments of the invention, the antibody, particularly the monoclonal antibody, particularly the chimeric or humanized antibody according to the invention as described in the various embodiments specifically recognizes and binds to a phospho-epitope on a mammalian, particularly on the human Tau protein, particularly a microtubule-associated protein tau, particularly an aggregated microtubule-associated and hyperphosphorylated protein tau such as that present in paired helical filaments (PHF), which are the predominant structures in neurofibrillary tangles, neuropil threads and dystrophic neurites, but, in one embodiment, does not bind to the corresponding unphosphorylated epitope and/or to non-related epitopes.

In a specific embodiment of the invention, the human tau protein is the human Tau protein as shown in SEQ ID NO: 19.

In one embodiment, the present invention provides an antibody, particularly a monoclonal antibody, particularly a chimeric antibody or a functional fragment thereof, or a humanized antibody or a functional fragment thereof, particularly a humanized monoclonal antibody or a functional fragment thereof, particularly an antibody of any of the preceding embodiments, which antibody recognizes and specifically binds to a phospho-epitope on a mammalian, particularly on the human Tau protein as shown in SEQ ID NO: 19 or on a fragment thereof, particularly to a pathological protein tau conformer, but, in one embodiment, does not bind to the corresponding unphosphorylated epitope and/or to non-related epitopes, wherein said epitope comprises amino acid residues aa 404-411 of the human Tau protein as shown in SEQ ID NO: 19 with the requirement of phosphorylated Serine at position 409 (pS409).

In a specific embodiment, the present invention provides an antibody, particularly a monoclonal antibody, particularly a chimeric antibody or a functional fragment thereof, or a humanized antibody or a functional fragment thereof, particularly a humanized monoclonal antibody or a functional fragment thereof, particularly an antibody of any of the preceding embodiments, which antibody preferentially recognizes and binds to some or all Tau amino acid residues selected from the group consisting of H407, pS409, N410, and V411, but particularly to pS409.

In another specific embodiment said antibody or fragment also recognizes and binds to the pS404 residue, even though to a lesser extent. In particular, the binding to the pS404 residue amounts to about 10%, particularly to about 20%, particularly to about 30% of the binding to the pS409 residue.

In one embodiment, the present invention provides an antibody, particularly a monoclonal antibody, particularly a chimeric antibody or a functional fragment thereof, or a humanized antibody or a functional fragment thereof, particularly a humanized monoclonal antibody or a functional fragment thereof, particularly an antibody of any of the preceding embodiments, which antibody recognizes and specifically binds to a phospho-epitope on a mammalian, particularly on the human Tau protein as shown in SEQ ID NO: 19 or on a fragment thereof, particularly to a pathological protein tau conformer, but, in one embodiment, does not bind to the corresponding unphosphorylated epitope and/or to non-related epitopes, wherein said epitope comprises amino acid residues aa 405-411 of the human Tau protein as shown in SEQ ID NO: 19 comprising a phosphorylated Serine (Ser) at position 409 (pS409) and wherein said antibody or functional fragment thereof preferentially recognizes and binds to some or all Tau amino acid residues selected from the group consisting of H407, pS409, N410, and V411, but particularly to pS409.

In one embodiment, the present invention provides a chimeric antibody or a functional fragment thereof, or a humanized antibody or a functional fragment thereof, particularly a humanized monoclonal antibody or a functional fragment thereof, particularly a humanized antibody of any of the preceding embodiments, which antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes, wherein said binding antibody comprises a first binding domain, particularly a binding domain of a Heavy Chain Variable Region (HCVR), which contains integrated into human- or primate-derived framework regions in sequence a CDR1 with the amino acid sequence shown in SEQ ID NO: 1, a CDR2 with the amino acid sequence shown in SEQ ID NO: 2, and a CDR3 with the amino acid sequence shown in SEQ ID NO: 3, or an amino acid sequence at least 50%, at least 60%, at least 70%, at least 80%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical thereto and/or a second binding domain, particularly a binding domain of a Light Chain Variable Region (LCVR), which contains integrated into human- or primate-derived framework regions in sequence a CDR1 with the amino acid sequence shown in SEQ ID NO: 4 or SEQ ID NO: 10, a CDR2 with the amino acid sequence shown in SEQ ID NO: 5, and a CDR3 with the amino acid sequence shown in SEQ ID NO: 6, or an amino acid sequence at least 50%, at least 60%, at least 70%, at least 80%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical thereto.

One embodiment of the present invention relates to a chimeric antibody or a functional fragment thereof, or a humanized antibody or a functional fragment thereof, particularly a humanized monoclonal antibody or a functional fragment thereof, particularly a humanized antibody of any of the preceding embodiments, which antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding antibody comprises a first binding domain, particularly a binding domain of a Heavy Chain Variable Region (HCVR), which contains integrated into human- or primate-derived framework regions in sequence a CDR1 with the amino acid sequence shown in SEQ ID NO: 1 or an amino acid sequence at least 60%, at least 70%, at least 80%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical thereto, a CDR2 with the amino acid sequence shown in SEQ ID NO: 2 or an amino acid sequence at least 60%, at least 70%, at least 80%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical thereto, and a CDR3 with the amino acid sequence shown in SEQ ID NO: 3, or an amino acid sequence at least 20%, at least 30%, at least 40%, at least 50%, at least 60%, at least 70%, at least 80%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical thereto and/or a second binding domain, particularly a binding domain of a Light Chain Variable Region (LCVR), which contains integrated into human- or primate-derived framework regions in sequence a CDR1 with the amino acid sequence shown in SEQ ID NO: 4 or SEQ ID NO: 10, or an amino acid sequence at least 60%, at least 70%, at least 80%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical thereto, a CDR2 with the amino acid sequence shown in SEQ ID NO: 5, and a CDR3 with the amino acid sequence shown in SEQ ID NO: 6 or an amino acid sequence at least 60%, at least 70%, at least 80%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical thereto.

In one embodiment, the present invention provides a chimeric antibody or a functional fragment thereof, or a humanized antibody or a functional fragment thereof, particularly a humanized monoclonal antibody or a functional fragment thereof, particularly a humanized antibody of any of the preceding embodiments, which antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding antibody comprises a first binding domain, particularly a binding domain of a Heavy Chain Variable Region (HCVR), which contains integrated into human- or primate-derived framework regions in sequence a CDR1 with the amino acid sequence shown in SEQ ID NO: 1 or an amino acid sequence at least at least 81%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical thereto, a CDR2 with the amino acid sequence shown in SEQ ID NO: 2 or an amino acid sequence at least at least 71%, at least 75%, at least 8%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical thereto, and a CDR3 with the amino acid sequence shown in SEQ ID NO: 3 at least 20%, at least 30%, at least 40%, at least 50%, at least 60%, at least 70%, at least 80%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical thereto, and/or a second binding domain, particularly a binding domain of a Light Chain Variable Region (LCVR), which contains integrated into human- or primate-derived framework regions in sequence a CDR1 with the amino acid sequence shown in SEQ ID NO: 4 or SEQ ID NO: 10, or an amino acid sequence at least 82%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical thereto, a CDR2 with the amino acid sequence shown in SEQ ID NO: 5, and a CDR3 with the amino acid sequence shown in SEQ ID NO: 6, or an amino acid sequence at least 50%, at least 68%, at least 70%, at least 80%, particularly at least 85%, particularly at least 90%, at least 91%, at least 92%, at least 93%, at least 94%, particularly at least 95%, particularly at least 96%, particularly at least 97%, particularly at least 98%, particularly at least 99% or 100% identical thereto.

In one embodiment, the present invention provides a chimeric antibody or a functional fragment thereof, or a humanized antibody or a functional fragment thereof, particularly a humanized monoclonal antibody or a functional fragment thereof, particularly a humanized antibody of any of the preceding embodiments, which antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding antibody comprises a first binding domain, particularly a binding domain of a Heavy Chain Variable Region (HCVR), which contains integrated into human- or primate-derived framework regions in sequence a CDR1 with the amino acid sequence shown in SEQ ID NO: 1 or an amino acid sequence at least at least 85% identical thereto, a CDR2 with the amino acid sequence shown in SEQ ID NO: 2 or an amino acid sequence at least 75% identical thereto, and a CDR3 with the amino acid sequence shown in SEQ ID NO: 3 at least 20% identical thereto, and/or a second binding domain, particularly a binding domain of a Light Chain Variable Region (LCVR), which contains integrated into human- or primate-derived framework regions in sequence a CDR1 with the amino acid sequence shown in SEQ ID NO: 4 or SEQ ID NO: 10, or an amino acid sequence at least 85% identical thereto, a CDR2 with the amino acid sequence shown in SEQ ID NO: 5, and a CDR3 with the amino acid sequence shown in SEQ ID NO: 6, or an amino acid sequence at least 70% identical thereto.

In one embodiment, the present invention provides a chimeric antibody or a functional fragment thereof, or a humanized antibody or a functional fragment thereof, particularly a humanized monoclonal antibody or a functional fragment thereof, particularly a humanized antibody of any of the preceding embodiments, which antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding antibody comprises a first binding domain, particularly a binding domain of a Heavy Chain Variable Region (HCVR), which contains integrated into human- or primate-derived framework regions in sequence a CDR1 with the amino acid sequence shown in SEQ ID NO: 1, a CDR2 with the amino acid sequence shown in SEQ ID NO 2, and a CDR3 with the amino acid sequence shown in SEQ ID NO: 3, or an amino acid sequence at least 90% identical thereto, and/or a second binding domain, particularly a binding domain of a Light Chain Variable Region (LCVR), which contains integrated into human- or primate-derived framework regions in sequence a CDR1 with the amino acid sequence shown in SEQ ID NO: 4 or SEQ ID NO: 10, a CDR2 with the amino acid sequence shown in SEQ ID NO: 5, and a CDR3 with the amino acid sequence shown in SEQ ID NO: 6, or an amino acid sequence at least 90% identical thereto.

In one embodiment, the present invention provides a chimeric antibody or a functional fragment thereof, or a humanized antibody or a functional fragment thereof, particularly a humanized monoclonal antibody or a functional fragment thereof, particularly a humanized antibody of any of the preceding embodiments, which antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding antibody comprises a first binding domain, particularly a binding domain of a Heavy Chain Variable Region (HCVR), which contains integrated into human- or primate-derived framework regions in sequence a CDR1 with the amino acid sequence shown in SEQ ID NO: 1, a CDR2 with the amino acid sequence shown in SEQ ID NO: 2, and a CDR3 with the amino acid sequence shown in SEQ ID NO: 3, or an amino acid sequence at least 95% identical thereto, and/or a second binding domain, particularly a binding domain of a Light Chain Variable Region (LCVR), which contains integrated into human- or primate-derived framework regions in sequence a CDR1 with the amino acid sequence shown in SEQ ID NO: 4 or SEQ ID NO: 10, a CDR2 with the amino acid sequence shown in SEQ ID NO: 5, and a CDR3 with the amino acid sequence shown in SEQ ID NO: 6, or an amino acid sequence at least 95% identical thereto.

In one embodiment, the present invention provides a chimeric antibody or a functional fragment thereof, or a humanized antibody or a functional fragment thereof, particularly a humanized monoclonal antibody or a functional fragment thereof, particularly a humanized antibody of any of the preceding embodiments, which antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding antibody comprises a first binding domain, particularly a binding domain of a Heavy Chain Variable Region (HCVR), which contains integrated into human- or primate-derived framework regions in sequence a CDR1 with the amino acid sequence shown in SEQ ID NO: 1, a CDR2 with the amino acid sequence shown in SEQ ID NO: 2, and a CDR3 with the amino acid sequence shown in SEQ ID NO: 3, or an amino acid sequence at least 98% identical thereto, and/or a second binding domain, particularly a binding domain of a Light Chain Variable Region (LCVR), which contains integrated into human- or primate-derived framework regions in sequence a CDR1 with the amino acid sequence shown in SEQ ID NO: 4 or SEQ ID NO: 10, a CDR2 with the amino acid sequence shown in SEQ ID NO: 5, and a CDR3 with the amino acid sequence shown in SEQ ID NO: 6, or an amino acid sequence at least 98% identical thereto.

In one embodiment, the present invention provides a chimeric antibody or a functional fragment thereof, or a humanized antibody or a functional fragment thereof, particularly a humanized monoclonal antibody or a functional fragment thereof, particularly a humanized antibody of any of the preceding embodiments, which antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding antibody comprises a first binding domain, particularly a binding domain of a Heavy Chain Variable Region (HCVR), which contains integrated into human- or primate-derived framework regions in sequence a CDR1 with the amino acid sequence shown in SEQ ID NO: 1, a CDR2 with the amino acid sequence shown in SEQ ID NO: 2, and a CDR3 with the amino acid sequence shown in SEQ ID NO: 3, and/or a second binding domain, particularly a binding domain of a Light Chain Variable Region (LCVR), which contains integrated into human- or primate-derived framework regions in sequence a CDR1 with the amino acid sequence shown in SEQ ID NO: 4, a CDR2 with the amino acid sequence shown in SEQ ID NO: 5, and a CDR3 with the amino acid sequence shown in SEQ ID NO: 6.

In one embodiment, the present invention provides a chimeric antibody or a functional fragment thereof, or a humanized antibody or a functional fragment thereof, particularly a humanized monoclonal antibody or a functional fragment thereof, particularly a humanized antibody of any of the preceding embodiments, which antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding antibody comprises a first binding domain, particularly a binding domain of a Heavy Chain Variable Region (HCVR), which contains integrated into human- or primate-derived framework regions in sequence a CDR1 with the amino acid sequence shown in SEQ ID NO: 1, a CDR2 with the amino acid sequence shown in SEQ ID NO: 2, and a CDR3 with the amino acid sequence shown in SEQ ID NO: 3, and/or a second binding domain, particularly a binding domain of a Light Chain Variable Region (LCVR), which contains integrated into human- or primate-derived framework regions in sequence a CDR1 with the amino acid sequence shown in SEQ ID NO: 10, a CDR2 with the amino acid sequence shown in SEQ ID NO: 5, and a CDR3 with the amino acid sequence shown in SEQ ID NO: 6. The invention further relates to a chimeric antibody or a functional fragment thereof, or a humanized antibody or a fragment thereof, which comprises integrated into human- or primate-derived framework regions at least two peptides, particularly at least three peptides, particularly at least four peptides, particularly at least five peptides, particularly six peptides, which peptides are different and exhibit an amino acid sequence selected from the group of sequences consisting of SEQ ID NO:1 representing CDR1, SEQ ID NO: 2 representing CDR2 and SEQ ID NO: 3 representing CDR3 of the Heavy Chain Variable Region (HCVR) and SEQ ID NO: 4 representing CDR1, SEQ ID NO: 5 representing CDR2 and SEQ ID NO: 6 representing CDR3 of the Light Chain Variable Region (LCVR), wherein the same CDR cannot be present twice in the antibody.

The invention further relates to a chimeric antibody or a functional fragment thereof, or a humanized antibody or a fragment thereof, which comprises integrated into human- or primate-derived framework regions at least two peptides, particularly at least three peptides, particularly at least four peptides, particularly at least five peptides, particularly six peptides, which peptides are different and exhibit an amino acid sequence selected from the group of sequences consisting of SEQ ID NO:1 representing CDR1, SEQ ID NO: 2 representing CDR2 and SEQ ID NO: 3 representing CDR3 of the Heavy Chain Variable Region (HCVR) and SEQ ID NO: 10 representing CDR1, SEQ ID NO: 5 representing CDR2 and SEQ ID NO: 6 representing CDR3 of the Light Chain Variable Region (LCVR), wherein the same CDR cannot be present twice in the antibody.

In a specific embodiment, the invention relates to a chimeric antibody or a functional fragment thereof, or a humanized antibody or a fragment thereof, which comprises integrated into human- or primate-derived framework regions peptides with an amino acid sequence of SEQ ID NO: 1 representing CDR1, SEQ ID NO: 2 representing CDR2 and SEQ ID NO: 3 representing CDR3 of the Heavy Chain Variable Region (HCVR) and SEQ ID NO: 4 representing CDR1, SEQ ID NO: 5 representing CDR2 and SEQ ID NO: 6 representing CDR3 of the Light Chain Variable Region (LCVR).

In a specific embodiment, the invention relates to a chimeric antibody or a functional fragment thereof, or a humanized antibody or a fragment thereof, which comprises integrated into human- or primate-derived framework regions peptides with an amino acid sequence of SEQ ID NO: 1 representing CDR1, SEQ ID NO: 2 representing CDR2 and SEQ ID NO: 3 representing CDR3 of the Heavy Chain Variable Region (HCVR) and SEQ ID NO: 10 representing CDR1 SEQ ID NO 5 representing CDR2 and SEQ ID NO: 6 representing CDR3 of the Light Chain Variable Region (LCVR). In one embodiment, the present invention provides a humanized antibody or a functional fragment thereof, particularly a humanized monoclonal antibody or a functional fragment thereof, particularly a humanized antibody of any of the preceding embodiments, which antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said antibody or antibody fragment comprises a a. first binding domain, particularly a binding domain of a Heavy Chain Variable Region (HCVR), which contains an amino acid sequence having at least 84%, particularly at least 85%, at least 86%, at least 87%, at least 88%, at least 89%, particularly at least 90%, at least 91%, at least 92%, at least 93%, at least 94%, particularly at least 95%, particularly at least 96%, particularly at least 97%, particularly at least 98%, particularly at least 99% or 100% identity to the sequence shown in SEQ ID NO: 7, SEQ ID NO: 20 or SEQ ID NO: 21, and/or a second binding domain, particularly a binding domain of a Light Chain Variable Region (LCVR), which contains an amino acid sequence having at least 89%, particularly at least 90%, particularly at least 91%, at least 92%, at least 93%, at least 94%, particularly at least 95%, particularly at least 96%, particularly at least 97%, particularly at least 98%, particularly at least 99% or 100% identity to the sequence shown in SEQ ID NO: 8; or a b. first binding domain, particularly a binding domain of a Heavy Chain Variable Region (HCVR), which contains an amino acid sequence having at least 84%, particularly at least 85%, at least 86%, at least 87%, at least 88%, at least 89%, particularly at least 90%, at least 91%, at least 92%, at least 93%, at least 94%, particularly at least 95%, particularly at least 96%, particularly at least 97%, particularly at least 98%, particularly at least 99% or 100% identity to the sequence shown in SEQ ID NO: 7, SEQ ID NO: 20 or SEQ ID NO: 21, and/or a second binding domain, particularly a binding domain of a Light Chain Variable Region (LCVR), which contains an amino acid sequence having at least 90%, at least 91%, at least 92%, at least 93%, at least 94%, particularly at least 95%, particularly at least 96%, particularly at least 97%, particularly at least 98%, particularly at least 99% or 100% identity to the sequence shown in SEQ ID NO: 9.

In one embodiment, the present invention provides a humanized antibody or a functional fragment thereof, particularly a humanized monoclonal antibody or a functional fragment thereof, particularly a humanized antibody of any of the preceding embodiments, which antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding antibody comprises a. first binding domain, particularly a binding domain of a Heavy Chain Variable Region (HCVR), which contains an amino acid sequence having at least 84% identity to the sequence shown in SEQ ID NO: 7, SEQ ID NO: 20 or SEQ ID NO: 21, and/or a second binding domain, particularly a binding domain of a Light Chain Variable Region (LCVR), which contains an amino acid sequence having at least 89% identity to the sequence shown in SEQ ID NO: 8; or a b. first binding domain, particularly a binding domain of a Heavy Chain Variable Region (HCVR), which contains an amino acid sequence having at least 84% identity to the sequence shown in SEQ ID NO: 7, SEQ ID NO: 20 or SEQ ID NO: 21 and/or a second binding domain, particularly a binding domain of a Light Chain Variable Region (LCVR), which contains an amino acid sequence having at least 90% identity to the sequence shown in SEQ ID NO: 9.

In one embodiment, the present invention provides a humanized antibody or a functional fragment thereof, particularly a humanized monoclonal antibody or a functional fragment thereof, particularly a humanized antibody of any of the preceding embodiments, which antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding antibody comprises a. first binding domain, particularly a binding domain of a Heavy Chain Variable Region (HCVR), which contains an amino acid sequence having at least 90% identity to the sequence shown in SEQ ID NO: 7, SEQ ID NO: 20 or SEQ ID NO: 21, and/or a second binding domain, particularly a binding domain of a Light Chain Variable Region (LCVR), which contains an amino acid sequence having at least 90% identity to the sequence shown in SEQ ID NO: 8; or a b. first binding domain, particularly a binding domain of a Heavy Chain Variable Region (HCVR), which contains an amino acid sequence having at least 90% identity to the sequence shown in SEQ ID NO: 7, SEQ ID NO: 20 or SEQ ID NO: 21, and/or a second binding domain, particularly a binding domain of a Light Chain Variable Region (LCVR), which contains an amino acid sequence having at least 90% identity to the sequence shown in SEQ ID NO: 9.

In one embodiment, the present invention provides a humanized antibody or a functional fragment thereof, particularly a humanized monoclonal antibody or a functional fragment thereof, particularly a humanized antibody of any of the preceding embodiments, which antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding antibody comprises a. first binding domain, particularly a binding domain of a Heavy Chain Variable Region (HCVR), which contains an amino acid sequence having at least 95% identity to the sequence shown in SEQ ID NO: 7, SEQ ID NO: 20 or SEQ ID NO: 21, and/or a second binding domain, particularly a binding domain of a Light Chain Variable Region (LCVR), which contains an amino acid sequence having at least 95% identity to the sequence shown in SEQ ID NO: 8; or a b. first binding domain, particularly a binding domain of a Heavy Chain Variable Region (HCVR), which contains an amino acid sequence having at least 95% identity to the sequence shown in SEQ ID NO: 7, SEQ ID NO: 20 or SEQ ID NO: 21, and/or a second binding domain, particularly a binding domain of a Light Chain Variable Region (LCVR), which contains an amino acid sequence having at least 95% identity to the sequence shown in SEQ ID NO: 9.

In one embodiment, the present invention provides a humanized antibody or a functional fragment thereof, particularly a humanized monoclonal antibody or a functional fragment thereof, particularly a humanized antibody of any of the preceding embodiments, which antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes wherein said binding antibody comprises a. first binding domain, particularly a binding domain of a Heavy Chain Variable Region (HCVR), which contains an amino acid sequence shown in SEQ ID NO: 7, SEQ ID NO: 20 or SEQ ID NO: 21, and/or a second binding domain, particularly a binding domain of a Light Chain Variable Region (LCVR), which contains an amino acid sequence shown in SEQ ID NO: 8; or a b. first binding domain, particularly a binding domain of a Heavy Chain Variable Region (HCVR), which contains an amino acid sequence shown in SEQ ID NO: 7, SEQ ID NO: 20 or SEQ ID NO: 21, and/or a second binding domain, particularly a binding domain of a Light Chain Variable Region (LCVR), which contains an amino acid sequence shown in SEQ ID NO: 9.

In one embodiment, the present invention provides a humanized antibody or a functional fragment thereof, particularly a humanized monoclonal antibody or a functional fragment thereof, particularly a humanized antibody of any of the preceding embodiments, which antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes, which antibody further comprises a heavy chain constant region and a light chain constant region, particularly the heavy chain constant region as shown in SEQ ID NOs: 14-17 and the light chain constant region as shown in SEQ ID NO: 18.

In one embodiment said humanized antibody or a functional fragment thereof according to any of the preceding embodiments comprises a heavy chain constant region with a mutation in the hinge region, particularly a mutation in the hinge region which prevents Fab arm exchange and thus generation of bi-specific antibodies. In a specific embodiment, the heavy chain hinge region comprises a Ser to Pro exchange at position 228 (S228P).

In one embodiment said humanized antibody or a functional fragment thereof according to any of the preceding embodiments comprises a heavy chain constant region with a modification (e.g., a deletion or a mutation) at the C-terminus. In a specific embodiment, the heavy chain comprises a deletion of the C-terminal lysine (des-K). This C-terminal lysine (residue 447 according to the EU numbering system) of the Fc region of the constant region may be removed, for example, during purification of the antibody or by recombinant engineering of the nucleic acid encoding the antibody. This mutation prevents random enzymatic cleavage of the C-terminal lysine by antibody producing cells such as, for example, CHO cells.

In another embodiment, said humanized antibody or a functional fragment thereof according to any of the preceding embodiments comprises a heavy chain constant region without a modification (e.g., a deletion or a mutation) at the C-terminus. In a specific embodiment, the heavy chain constant region comprises the C-terminal lysine (a lysine at the C-terminal end of the heavy chain constant region). As such, an antibody according to the present invention can comprise an antibody with K447, with all K447 removed, or a mixture of antibodies with and without the K447 residue.

In one embodiment of the invention, the binding peptide of any of the preceding embodiments is an antibody, particularly an antibody of the—IgG1, IgG2, IgG3 or the IgG4 isotype, particularly a polyclonal antibody, a monoclonal antibody, a chimeric antibody, a humanized antibody or a fully human antibody. In one embodiment of the invention, the binding peptide of any of the preceding embodiments is an antibody, particularly an antibody of the IgG1 N297G isotype, having an asparagine to glycine substitution at position 297 (EU numbering system) in the Fc region of the antibody, particularly a polyclonal antibody, a monoclonal antibody, a chimeric antibody, a humanized antibody or a fully human antibody.

One embodiment of the invention relates to a polynucleotide encoding the binding peptide of any one of the preceding embodiments.

In one embodiment, said polynucleotide comprises a nucleic acid molecule comprising a nucleotide sequence encoding an antibody variable region comprising SEQ ID NO: 1-3 representing the Complementarity Determining Regions (CDRs) 1, 2 and 3 of the Heavy Chain Variable Region (HCVR).

In another embodiment, said polynucleotide comprises nucleic acid molecule comprising a nucleotide sequence encoding an antibody variable region comprising SEQ ID NO: 4-6 representing the Complementarity Determining Regions (CDRs) 1, 2 and 3 of the Light Chain Variable Region (LCVR).

In another embodiment, said polynucleotide comprises nucleic acid molecule comprising a nucleotide sequence encoding an antibody variable region comprising SEQ ID NO: 10, 5 and 6 representing the Complementarity Determining Regions (CDRs) 1, 2 and 3 of the Light Chain Variable Region (LCVR).

In one embodiment, the invention relates to a polynucleotide comprising a nucleic acid molecule selected from the group consisting of
  a. a nucleic acid molecule comprising a nucleotide sequence as depicted in SEQ ID NOs: 11 and/or a nucleotide sequence as depicted in SEQ ID NOs: 12; or
  b. a nucleic acid molecule comprising a nucleotide sequence that has at least 85% sequence identity to the sequence shown in SEQ ID NO: 11 and/or a nucleotide sequence that has at least 85% sequence identity to the sequence shown in SEQ ID NO: 12; or
  c. a nucleic acid molecule comprising a nucleotide sequence that has at least 90% sequence identity to the sequence shown in SEQ ID NO: 11 and/or a nucleotide sequence that has at least 90% sequence identity to the sequence shown in SEQ ID NO. 12; or
  d. a nucleic acid molecule comprising a nucleotide sequence that has at least 95% sequence identity to the sequence shown in SEQ ID NO: 11 and/or a nucleotide sequence that has at least 95% sequence identity to the sequence shown in SEQ ID NO: 12; or
  e. a nucleic acid molecule comprising a nucleotide sequence that has at least 98% sequence identity to the sequence shown in SEQ ID NO: 11 and/or a nucleotide sequence that has at least 98% sequence identity to the sequence shown in SEQ ID NO: 12; or;
  f. a nucleic acid molecule comprising a nucleotide sequence the complementary strand of which hybridizes to the nucleic acid molecule of any of a)-e);
  g. a nucleic acid molecule comprising a nucleotide sequence that deviates from the nucleotide sequence defined in any of a)-f) by the degeneracy of the genetic code.

In one embodiment, the invention relates to a polynucleotide comprising a nucleic acid molecule selected from the group consisting of
  a. a nucleic acid molecule comprising a nucleotide sequence as depicted in SEQ ID NOs: 11 and/or a nucleotide sequence as depicted in SEQ ID NOs: 13; or
  b. a nucleic acid molecule comprising a nucleotide sequence that has at least 85% sequence identity to the sequence shown in SEQ ID NO: 11 and/or a nucleotide sequence that has at least 85% sequence identity to the sequence shown in SEQ ID NO: 13; or
  c. a nucleic acid molecule comprising a nucleotide sequence that has at least 90% sequence identity to the sequence shown in SEQ ID NO: 11 and/or a nucleotide sequence that has at least 90% sequence identity to the sequence shown in SEQ ID NO: 13; or
  d. a nucleic acid molecule comprising a nucleotide sequence that has at least 95% sequence identity to the sequence shown in SEQ ID NO: 11 and/or a nucleotide sequence that has at least 95% sequence identity to the sequence shown in SEQ ID NO: 13; or
  e. a nucleic acid molecule comprising a nucleotide sequence that has at least 98% sequence identity to the sequence shown in SEQ ID NO: 11 and/or a nucleotide sequence that has at least 98% sequence identity to the sequence shown in SEQ ID NO: 13; or;
  f. a nucleic acid molecule comprising a nucleotide sequence the complementary strand of which hybridizes to the nucleic acid molecule of any of a)-e);
  g. a nucleic acid molecule comprising a nucleotide sequence that deviates from the nucleotide sequence defined in any of a)-f) by the degeneracy of the genetic code.

In one embodiment, the invention relates to a polynucleotide comprising a nucleic acid molecule comprising a nucleotide sequence as shown in SEQ ID NO: 11 and/or a nucleotide sequence as shown in SEQ ID NO: 12.

In one embodiment, the invention relates to a polynucleotide comprising a nucleic acid molecule comprising a nucleotide sequence as shown in SEQ ID NO: 11 and/or a nucleotide sequence as shown in SEQ ID NO: 13.

The present invention further provides a humanized antibody or a fragment thereof, which comprises the Heavy Chain Variable Region (HCVR) of SEQ ID NO: 7 and the heavy chain constant region of SEQ ID NOs: 14-17.

The present invention further provides a humanized antibody or a fragment thereof, which comprises the Heavy Chain Variable Region (HCVR) of SEQ ID NO: 20 or SEQ ID NO: 21.

The present invention further provides a humanized antibody or a fragment thereof, which comprises the Heavy Chain Variable Region (HCVR) of SEQ ID NO: 20 or SEQ ID NO: 21, and the heavy chain constant region of SEQ ID NOs: 14-17.

The present invention further provides a humanized antibody or a fragment thereof, which comprises the Heavy Chain of SEQ ID NO: 24, SEQ ID NO: 25, SEQ ID NO: 26, SEQ ID NO: 27, SEQ ID NO: 28, SEQ ID NO: 29, SEQ ID NO: 30, or SEQ ID NO: 31.

The present invention further provides a humanized antibody or a fragment thereof, which comprises the Light Chain Variable Region (LCVR) of SEQ ID NO: 8 and the light chain constant region of SEQ ID NO: 18.

The present invention further provides a humanized antibody or a fragment thereof, which comprises the Light Chain Variable Region (LCVR) of SEQ ID NO: 9 and the light chain constant region of SEQ ID NO:18.

The present invention further provides a humanized antibody or a fragment thereof, which comprises the Light Chain of SEQ ID NO: 22 or SEQ ID NO: 23.

The present invention further provides a humanized antibody or a fragment thereof, which comprises the Heavy Chain of SEQ ID NO; 24, SEQ ID NO: 25, SEQ ID NO: 26, SEQ ID NO: 27, SEQ ID NO: 28, SEQ ID NO: 29, SEQ ID NO 30, or SEQ ID NO: 31, and the Light Chain of SEQ ID NO: 22 or SEQ ID NO: 23.

The present invention further provides a humanized antibody or a fragment thereof, which comprises the Heavy Chain Variable Region (HCVR) of SEQ ID NO: 7 and the heavy chain constant region of SEQ ID NOs: 14-17 and the Light Chain Variable Region (LCVR) of SEQ ID NO: 8 and the light chain constant region of SEQ ID NO: 18.

The present invention further provides a humanized antibody or a fragment thereof, which comprises the Heavy Chain Variable Region (HCVR) of SEQ ID NO: 7 and the heavy chain constant region of SEQ ID NOs: 14-17 and the Light Chain Variable Region (LCVR) of SEQ ID NO: 9 and the light chain constant region of SEQ ID NO: 18.

The present invention further provides a humanized antibody or a fragment thereof, which comprises the Heavy Chain Variable Region (HCVR) of SEQ ID NO: 20 or SEQ ID NO: 21, and the heavy chain constant region of SEQ ID NOs: 14-17, and the Light Chain Variable Region (LCVR) of SEQ ID NO: 8 or SEQ ID NO: 9, and the light chain constant region of SEQ ID NO: 18.

In one embodiment, the invention relates to a polynucleotide encoding the humanized antibodies of any one of the preceding embodiments.

The chimeric or humanized antibodies according to the invention as described in the various embodiments, recognize and specifically bind to a phospho-epitope on a mammalian, particularly on the human Tau protein or on a fragment thereof, particularly to a phospho-epitope on aggregated Tau protein, particularly to a pathological protein tau conformer, but does not bind to the corresponding unphosphorylated epitope and/or to non-related epitopes, wherein said antibodies have a high binding affinity to soluble and insoluble Tau protein, and modulates soluble and insoluble Tau levels, particularly in the brain, particularly with a (c) dissociation constant of at least 100 nM, particularly at least 80 nM, particularly at least 70 nM, particularly at least 50 nM, particularly at least 10 nM, particularly of at least 8 nM, particularly of at least 5 nM, particularly of at least 2 nM, particularly of at least 1 nM, particularly of at least 500 pM, particularly of at least 400 pM, particularly of at least 300 pM, particularly of at least 200 pM, particularly of at least 100 pM, particularly of at least 50 pM and/or (d) an association rate constant of $10^4$ $M^{-1}s^{-1}$ or greater, particularly of between $3\text{-}5\times10^4$ $M^{-1}s^{-1}$ or greater, particularly of $10^5$ $M^{-1}s^{-1}$ or greater; particularly of $0.5\text{-}9\times10^5$ $M^{-1}s^{-1}$ or greater; particularly of $10^6$ $M^{-1}s^{-1}$ or greater, particularly of $1\text{-}4\times10^6$ $M^{-1}s^{-1}$ or greater, particularly of $10^7$ $M^{-1}s^{-1}$ or greater.

In certain embodiments, the present invention relates to chimeric or humanized antibodies according to the invention as described in the various embodiments, which antibodies recognize and specifically bind to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes, wherein said antibodies have a high binding affinity with a dissociation constant of at least 100 nM and an association rate constant of $10^5$ $M^{-1}s^{-1}$ or greater, particularly a dissociation constant of at least 80 nM and an association rate constant of $10^5$ $M^{-1}s^{-1}$ or greater, particularly a dissociation constant of at least 70 nM and an association rate constant of $10^5$ $M^{-1}s^{-1}$ or greater, particularly a dissociation constant of at least 10 nM and an association rate constant of $10^5$ $M^{-1}s^{-1}$ or greater, particularly a dissociation constant of at least 200 pM and an association rate constant of $10^5$ $M^{-1}s^{-1}$ or greater, particularly a dissociation constant of at least 100 pM and an association rate constant of $10^6$ $M^{-1}s^{-1}$ or greater.

In various embodiments of the invention, the chimeric or humanized antibodies according to the invention as described in the various embodiments specifically recognize and bind to a phospho-epitope on a mammalian, particularly on the human Tau protein, particularly a microtubule-associated protein tau, particularly an aggregated microtubule-associated and hyperphosphorylated protein tau such as that present in paired helical filaments (PHF), which are the predominant structures in neurofibrillary tangles, neuropil threads and dystrophic neurites, but, in one embodiment, does not bind to the corresponding unphosphorylated epitope and/or to non-related epitopes.

In a specific embodiment of the invention, the human tau protein is the human Tau protein as shown in SEQ ID NO: 19.

The chimeric or humanized antibodies according to any one of the preceding embodiments can thus be used for reducing the levels of total soluble tau protein, particularly of soluble phosphorylated tau protein, in the brain, particularly in the brain cortex and/or hippocampus, of a mammal or a human containing increased levels of soluble tau protein and/or soluble phosphorylated tau protein.

The chimeric or humanized antibodies according to any one of the preceding embodiments can also be used for reducing the levels of paired helical filaments containing hyperphosphorylated tau protein (pTau PHF) in the brain, particularly in the brain cortex and/or hippocampus, of a mammal or a human containing increased levels of said pTau paired helical filaments (pTau PHF).

Reduction of the level of total soluble tau protein and/or soluble phosphorylated tau protein and/or pTau paired helical filaments (pTau PHF) in the brain, particularly in the brain cortex and/or hippocampus, of a mammal or a human containing increased levels of said tau protein variants, which contribute to tau-protein-associated diseases, disorders or conditions in said mammal or human, may lead to an improvement and/or alleviation of the symptoms associated with such tau-protein-associated diseases, disorders or conditions.

The chimeric or humanized antibodies according to any one of the preceding embodiments can therefore be used in therapy, particularly in human therapy, for slowing or halting the progression of a tau-protein-associated disease, disorder or condition.

The chimeric or humanized antibodies according to any one of the preceding embodiments can further be used in therapy, particularly in human therapy, for improving or alleviating the symptoms associated with tau-protein-associated diseases, disorders or conditions such as, for example, impairment or loss of cognitive functions including reasoning, situational judgement, memory capacity, learning, special navigation, etc.

In one embodiment, the invention relates to the chimeric or humanized antibodies according to any one of the preceding embodiments for use in therapy, particularly for use in the prevention or treatment of tauopathies, a group of tau-protein-associated diseases and disorders, or for alleviating the symptoms associated with tauopathies.

In one embodiment, the invention relates to the chimeric or humanized antibodies according to any one of the preceding embodiments for retaining or increasing cognitive memory capacity in a mammal suffering from a tauopathy.

Binding of the peptides or antibodies according to the preceding embodiments to tau tangles and pTau on brains may be determined by applying protein immuno-reactivity testing of selected brain sections and by Western blotting of brain homogenates, respectively, as described in the Examples.

In another embodiment, the present invention provides a pharmaceutical composition comprising a chimeric or humanized antibody or a functional fragment thereof, or a polynucleotide, according to any one of the preceding embodiments, or a combination thereof, in a therapeutically effective amount, optionally together with a pharmaceutically acceptable carrier.

In one embodiment, the chimeric or humanized antibody or a functional fragment thereof, or a polynucleotide, or a pharmaceutical composition, according to any one of the preceding embodiments, or a combination thereof, is used in therapy, particularly in human therapy for the treatment or alleviation of the symptoms of tau-protein-associated diseases or disorders including neurodegenerative disorders such as tauopathies.

The chimeric or humanized antibodies and/or pharmaceutical compositions according to any one of the preceding embodiments may thus be used for slowing or halting the progression of a tau-protein-associated disease, disorder or condition, upon administration of said antibodies and/or pharmaceutical compositions to an animal, particularly a mammal, particularly a human, suffering from such a disease or condition.

The chimeric or humanized antibodies and/or pharmaceutical compositions according to any one of the preceding embodiments may further be used for improving or alleviating the symptoms associated with tau-protein-associated diseases, disorders or conditions such as, for example, impairment or loss of cognitive functions including reasoning, situational judgement, memory capacity, learning, special navigation, etc, upon administration of said antibodies and/or pharmaceutical compositions to an animal, particularly a mammal, particularly a human, suffering from such a disease or condition.

In one embodiment, the chimeric or humanized antibody or a functional fragment thereof, or a polynucleotide, or a pharmaceutical composition, according to any one of the preceding embodiments, or a combination thereof, is used in the prevention or treatment of diseases and disorders which are caused by or associated with the formation of neurofibrillary lesions, the predominant brain pathology in tauopathy comprising a heterogeneous group of neurodegenerative diseases or disorders including diseases or disorders which show co-existence of tau and amyloid pathologies including, but not limited to, Alzheimer's Disease, Creutzfeldt-Jacob disease, Dementia pugilistica, Down's Syndrome, Gerstmann-Sträussler-Scheinker disease, inclusion-body myositis, and prion protein cerebral amyloid angiopathy, traumatic brain injury and further diseases or disorders which do not show a distinct amyloid pathology including, but not limited to, amyotrophic lateral sclerosis/parkinsonism-dementia complex of Guam, Non-Guamanian motor neuron disease with neurofibrillary tangles, argyrophilic grain dementia, corticobasal degeneration, diffuse neurofibrillary tangles with calcification, frontotemporal dementia with parkinsonism linked to chromosome 17, Hallevorden-Spatz disease, multiple system atrophy, Niemann-Pick disease, type C, Pallido-ponto-nigral degeneration, Pick's disease, progressive subcortical gliosis, progressive supranuclear palsy, Sub-acute sclerosing panencephalitis, Tangle only dementia, Postencephalitic Parkinsonism, Myotonic dystrophy.

In one embodiment, the chimeric or humanized antibody or a functional fragment thereof, or a polynucleotide, or a pharmaceutical composition, according to any one of the preceding embodiments, or a combination thereof, is used in the treatment of Alzheimer's Disease.

In one embodiment of the invention, a method is provided for modulating soluble and/or insoluble Tau levels, particularly in the brain, particularly in the brain cortex and/or hippocampus, of an animal, particularly a mammal or a human, comprising administering to said animal, particularly to said mammal or human, the chimeric or humanized antibody or a functional fragment thereof, or a polynucleotide, or a pharmaceutical composition, according to any one of the preceding embodiments, or a combination thereof.

In one aspect, modulation relates to reducing the levels of soluble tau protein, particularly of soluble phosphorylated tau protein, in the brain, particularly in the brain cortex and/or hippocampus, of an animal, particularly a mammal or a human containing increased levels of soluble tau protein and/or soluble phosphorylated tau protein.

In one embodiment of the invention, a method is provided for reducing the levels of insoluble tau protein, particularly of paired helical filaments containing hyperphosphorylated tau protein (pTau PHF) in the brain, particularly in the brain cortex and/or hippocampus, of an animal, particularly a mammal or a human, containing increased levels of insoluble tau protein, particularly of pTau paired helical filaments (pTau PHF) comprising administering to said animal, particularly to said mammal or human, the chimeric or humanized antibody or a functional fragment thereof, or a polynucleotide, or a pharmaceutical composition, according to any one of the preceding embodiments, or a combination thereof.

In one embodiment, the present invention relates to a method for slowing or halting the progression of a tau-protein-associated disease, disorder or condition in an animal, particularly a mammal or human comprising administering to said animal, particularly said mammal or human, suffering from such a disease or condition, the chimeric or humanized antibody or a functional fragment thereof, or a polynucleotide, or a pharmaceutical composition, according to any one of the preceding embodiments, or a combination thereof.

In one embodiment, the present invention relates to a method for improving or alleviating the symptoms associated with tau-protein-associated diseases, disorders or conditions such as, for example, impairment or loss of cognitive functions including reasoning, situational judgement, memory capacity, learning, special navigation, etc., in an animal, particularly a mammal or a human, comprising administering to said animal, particularly to said mammal or human, suffering from such a disease or condition, the chimeric or humanized antibody or a functional fragment thereof, or a polynucleotide, or a pharmaceutical composition, according to any one of the preceding embodiments, or a combination thereof.

In one embodiment, the present invention relates to a method for retaining or increasing cognitive memory capacity in a mammal suffering from a tauopathy.

In still another embodiment of the invention, a method is provided for the treatment of a tau-protein-associated disease or disorder including a neurodegenerative disease or disorder such as a tauopathy comprising administering to an animal, particularly to a mammal, but especially to human. suffering from such a disease or disorder, the chimeric or humanized antibody or a functional fragment thereof, or a polynucleotide, or a pharmaceutical composition, according to any one of the preceding embodiments, or a combination thereof.

In one embodiment of the invention, a method is provided for the treatment of diseases and disorders which are caused by or associated with the formation of neurofibrillary lesions, the predominant brain pathology in tauopathy comprising a heterogeneous group of neurodegenerative diseases or disorders including diseases or disorders which show co-existence of tau and amyloid pathologies including, but not limited to, Alzheimer's Disease, Creutzfeldt-Jacob disease, Dementia pugilistica, Down's Syndrome, Gerstmann-Sträussler-Scheinker disease, inclusion-body myositis, and prion protein cerebral amyloid angiopathy, traumatic brain injury and further diseases or disorders which do not show a distinct amyloid pathology including, but not limited to, amyotrophic lateral sclerosis/parkinsonism-dementia complex of Guam, Non-Guamanian motor neuron disease with neurofibrillary tangles, argyrophilic grain dementia, corticobasal degeneration, diffuse neurofibrillary tangles with calcification, frontotemporal dementia with parkinsonism linked to chromosome 17, Hallevorden-Spatz disease, multiple system atrophy, Niemann-Pick disease, type C, Pallido-ponto-nigral degeneration, Pick's disease, progressive subcortical gliosis, progressive supranuclear palsy, Subacute sclerosing panencephalitis Tangle only dementia, Postencephalitic Parkinsonism, Myotonic dystrophy, which method comprises administering to an animal, particularly to a mammal, but especially to human, suffering from such a disease or disorder, the chimeric or humanized antibody or a functional fragment thereof, or a polynucleotide, a pharmaceutical composition according to any one of the preceding embodiments, or a combination thereof.

In another embodiment of the invention, a method is provided for inducing a passive immune response in an animal, particularly a mammal or a human, suffering from a neurodegenerative disorder such as tauopathy by administering to said animal or human the chimeric or humanized antibody or a functional fragment thereof, or a polynucleotide, or a pharmaceutical composition, according to any one of the preceding embodiments, or a combination thereof.

In still another embodiment of the invention, a method of diagnosing a tau-protein-associated disease, disorder or condition in a patient is provided comprising detecting the immunospecific binding of the chimeric or humanized antibody or a functional fragment thereof according to any one of the preceding embodiments, to an epitope of the tau protein in a sample or in situ which includes the steps of
  a. bringing the sample or a specific body part or body area suspected to contain the tau protein into contact with the chimeric or humanized antibody or a functional fragment thereof to any one of the preceding embodiments, wherein said antibody or fragment thereof binds an epitope of the tau protein;
  b. allowing said antibody, or a functional fragment thereof, to bind to the tau protein to form an immunological complex;
  c. detecting the formation of the immunological complex; and
  d. correlating the presence or absence of the immunological complex with the presence or absence of tau protein in the sample or specific body part or area.

In still another embodiment of the invention, a method for diagnosing a predisposition to tau-protein-associated disease, disorder or condition in a patient is provided comprising detecting the immunospecific binding of the chimeric or humanized antibody or a functional fragment thereof according to any one of the preceding embodiments, to an epitope of the tau protein in a sample or in situ, which includes the steps of
  a. bringing the sample or a specific body part or body area suspected to contain the tau antigen into contact with the chimeric or humanized antibody or a functional fragment thereof according to any one of the preceding embodiments, which antibody or fragment thereof binds an epitope of the tau protein;
  b. allowing said antibody, or a functional fragment thereof, to bind to the tau antigen to form an immunological complex;
  c. detecting the formation of the immunological complex; and
  d. correlating the presence or absence of the immunological complex with the presence or absence of tau antigen in the sample or specific body part or area;
  e. comparing the amount of said immunological complex to a normal control value;
wherein an increase in the amount of said aggregate compared to a normal control value indicates that said patient is suffering from or is at risk of developing an tau-protein-associated disease or condition.

In one embodiment of the invention, a method is provided for monitoring minimal residual disease in a patient following treatment with the chimeric or humanized antibody or a functional fragment thereof according to any one of the preceding embodiments, wherein said method comprises:
  a. bringing the sample or a specific body part or body area suspected to contain the tau antigen into contact with the chimeric or humanized antibody or a functional fragment thereof according to any one of the preceding embodiments, which antibody or fragment thereof binds to an epitope of the tau protein;
  b. allowing said antibody, or a functional fragment thereof, to bind to the tau antigen to form an immunological complex;
  c. detecting the formation of the immunological complex; and
  d. correlating the presence or absence of the immunological complex with the presence or absence of tau antigen in the sample or specific body part or area,
  e. comparing the amount of said immunological complex to a normal control value,
wherein an increase in the amount of said aggregate compared to a normal control value indicates that said patient still suffers from a minimal residual disease.

In one embodiment, a method is provided for predicting responsiveness of a patient being treated with the chimeric or humanized antibody or a functional fragment thereof according to any one of the preceding embodiments, comprising
  a. bringing the sample or a specific body part or body area suspected to contain the tau antigen into contact with the chimeric or humanized antibody or a functional fragment thereof according to any one of the preceding embodiments, which antibody or fragment thereof binds to an epitope of the tau protein;
  b. allowing said antibody, or a functional fragment thereof, to bind to the tau antigen to form an immunological complex;
  c. detecting the formation of the immunological complex; and
  d. correlating the presence or absence of the immunological complex with the presence or absence of tau antigen in the sample or specific body part or area,
  e. comparing the amount of said immunological complex before and after onset of the treatment,
wherein a decrease in the amount of said aggregate indicates that said patient has a high potential of being responsive to the treatment.

In another embodiment, the invention relates to a test kit for detection and diagnosis of tau-protein-associated diseases, disorders or conditions comprising the chimeric or humanized antibody or a functional fragment thereof according to any one of the preceding embodiments.

In one embodiment said test kit comprises a container holding one or more the chimeric or humanized antibody or a functional fragment thereof according to any one of the preceding embodiments, and instructions for using the antibodies for the purpose of binding to tau antigen to form an immunological complex and detecting the formation of the immunological complex such that presence or absence of the immunological complex correlates with presence or absence of tau antigen.

In another embodiment, the invention relates to a cell line, particularly a bacterial cell line, particularly an *E. coli* cell line, producing the chimeric or humanized antibody or a functional fragment thereof according to any one of the preceding embodiments.

In one embodiment, the invention relates to a cell line, which is *Escherichia coli* 2B6A10C11-H deposited on Mar. 6, 2012 as DSM 25743.

In one embodiment, the invention relates to a cell line, which is *Escherichia coli* 2B6A10C11-L deposited on Mar. 6, 2012 as DSM 25744.

In one embodiment, the invention relates to a cell line, which is *Escherichia coli* 3A8A12G7-H deposited on Mar. 6, 2012 as DSM 25745.

In one embodiment, the invention relates to a cell line, which is *Escherichia coli* 3A8A12G7-L deposited on Mar. 6, 2012 as DSM 25746.

BRIEF DESCRIPTION OF FIGURES AND SEQUENCES

Figures

FIG. 4 shows Light chain of hACl-36-2B6-Ab1

FIG. 5 shows Light chain of hACl-36-3A8-Ab1

FIG. 6 shows Heavy chain of hACl-36-2B6-Ab1 and hACl-36-3A8-Ab1

SEQUENCES

Figure 1:
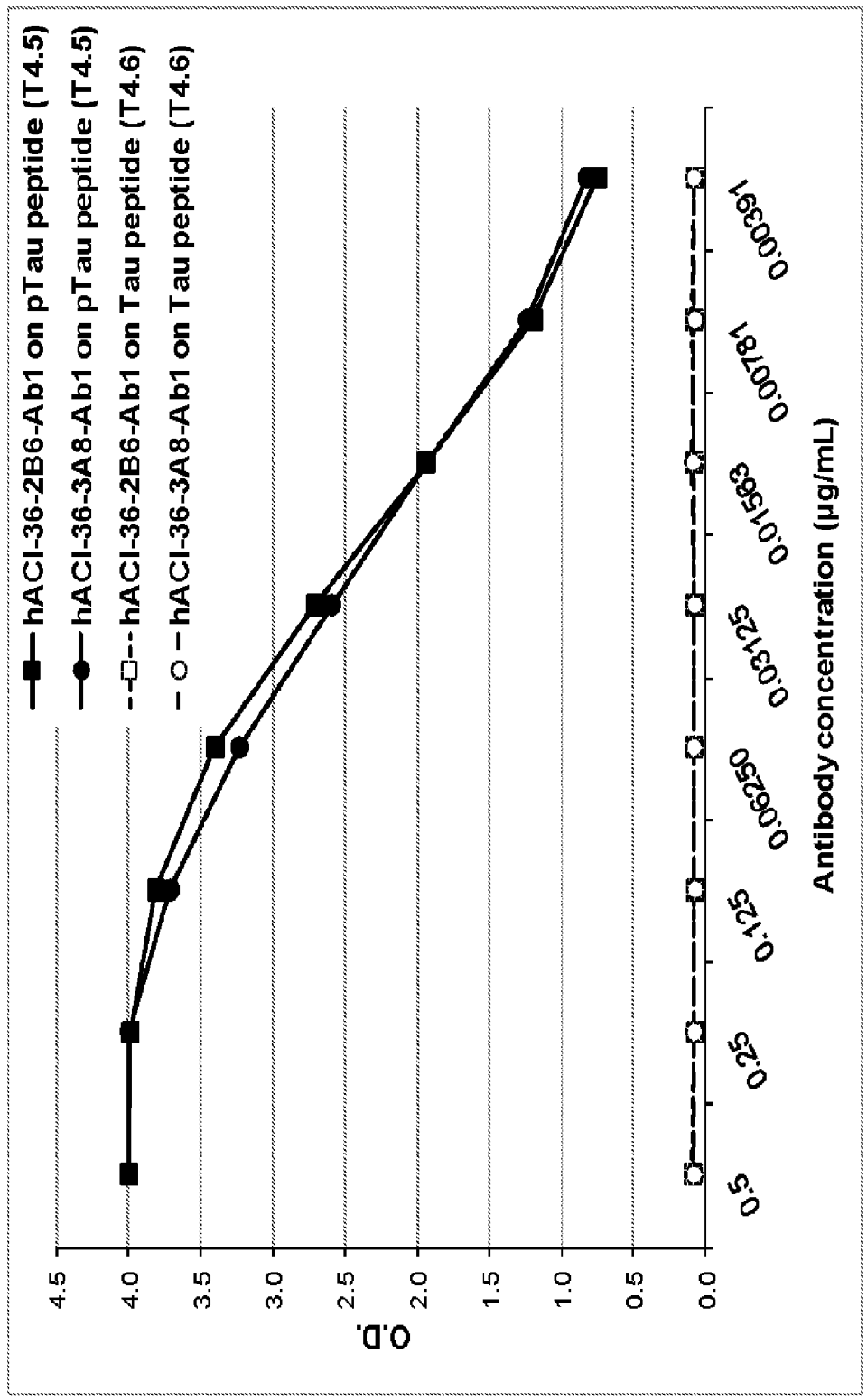
FIG. 1 shows binding of humanized anti-pTau antibodies hACl-36-2B6-Ab1 and hACl-36-3A8-Ab1 to pTau vaccine peptide (T4.5), without binding to the non-phosphorylated version of the same peptide (T4.6).

SEQ ID NO: 1 depicts the amino acid sequence of the CDR1 of the heavy chain variable region (HCVR) of humanized antibody hACl-36-3A8-Ab1 and hACl-36-2B6-Ab1 produced by *Escherichia coli* 3A8A12G7-H deposited on Mar. 6, 2012 as DSM 25745 and *Escherichia coli* 2B6A10C11-H deposited on Mar. 6, 2012 as DSM 25743, respectively.

SEQ ID NO: 2 depicts the amino acid sequence of the CDR2 of the heavy chain variable region (HCVR) of humanized antibody hACl-36-3A8-Ab1 and hACl-36-2B6-Ab1 produced by *Escherichia coli* 3A8A12G7-H deposited on Mar. 6, 2012 as DSM 25745 and *Escherichia coli* 2B6A10C11-H deposited on Mar. 6, 2012 as DSM 25743, respectively.

SEQ ID NO: 3 depicts the amino acid sequence of the CDR3 of the heavy chain variable region (HCVR) of humanized antibody hACl-36-3A8-Ab1 and hACl-36-2B6-Ab1 produced by *Escherichia coli* 3A8A12G7-H deposited on Mar. 6, 2012 as DSM 25745 and *Escherichia coli* 2B6A10C11-H deposited on Mar. 6, 2012 as DSM 25743, respectively.

SEQ ID NO: 4 depicts the amino acid sequence of the CDR1 of the light chain variable region (LCVR) of humanized antibody hACl-36-3A8-Ab1 produced by *Escherichia coli* 3A8A12G7-L deposited on Mar. 6, 2012

SEQ ID NO: 5 depicts the amino acid sequence of the CDR2 of the light chain variable region (LCVR) of humanized antibody hACl-36-3A8-Ab1 and hACl-36-2B6-Ab1 *Escherichia coli* 3A8A12G7-L deposited on Mar. 6, 2012 as DSM 25746 and *Escherichia coli* 2B6A10C11-L deposited on Mar. 6, 2012 as DSM 25744, respectively.

SEQ ID NO: 6 depicts the amino acid sequence of the CDR3 of the light chain variable region (LCVR) of humanized antibody hACl-36-3A8-Ab1 and hACl-36-2B6-Ab1 *Escherichia coli* 3A8A12G7-L deposited on Mar. 6, 2012 as DSM 25746 and *Escherichia coli* 2B6A10C11-L deposited on Mar. 6, 2012 as DSM 25744, respectively.

SEQ ID NO: 7 depicts the amino acid sequence of the heavy chain variable region (HCVR) of humanized antibody hACl-36-3A8-Ab1 and hACl-36-2B6-Ab1 produced by *Escherichia coli* 3A8A12G7-H deposited on Mar. 6, 2012 as DSM 25745 and *Escherichia coli* 2B6A10C11-H deposited on Mar. 6, 2012 as DSM 25743, respectively.

SEQ ID NO: 8 depicts the amino acid sequence of the light chain variable region (LCVR) of humanized antibody hACl-36-3A8-Ab1 produced by *Escherichia coli* 3A8A12G7-L deposited on Mar. 6, 2012 as DSM 25746.

SEQ ID NO: 9 depicts the amino acid sequence of the light chain variable region (LCVR) of humanized antibody hACl-36-2B6-Ab1 produced by *Escherichia coli* 2B6A10C11-L deposited on Mar. 6, 2012 as DSM 25744.

SEQ ID NO: 10 depicts the amino acid sequence of the CDR1 of the light chain variable region (LCVR) of humanized antibody hACl-36-2B6-Ab1 produced by *Escherichia coli* 2B6A10C11-L deposited on Mar. 6, 2012 as DSM 25744.

SEQ ID NO: 11 depicts the nucleotide sequence of the heavy chain (H) of humanized antibody hACl-36-3A8-Ab1 produced by *Escherichia coli* 3A8A12G7-H deposited on Mar. 6, 2012 as DSM 25745 and of the heavy chain (H) of humanized antibody hACl-36-2B6-Ab1 produced by *Escherichia coli* 2B6A10C11-H deposited on Mar. 6, 2012 as DSM 25743.

SEQ ID NO: 12 depicts the nucleotide sequence of the light chain (L) of humanized antibody hACl-36-3A8-Ab1 produced by *Escherichia coli* 3A8A12G7-L deposited on Mar. 6, 2012 as DSM 25746.

SEQ ID NO: 13 depicts the nucleotide sequence of the light chain (L) of humanized antibody hACl-36-2B6-Ab1 produced by *Escherichia coli* 2B6A10C11-L deposited on Mar. 6, 2012 as DSM 25744.

SEQ ID NO: 14 depicts the amino acid sequence of CH1 heavy chain constant region (HC) of the heavy chain of humanized antibody hACl-36-3A8-Ab1 produced by *Escherichia coli* 3A8A12G7-H deposited on Mar. 6, 2012 as DSM 25745 and of the heavy chain of humanized antibody hACl-36-2B6-Ab1 produced by *Escherichia coli* 2B6A10C11-H deposited on Mar. 6, 2012 as DSM 25743.

SEQ ID NO: 15 depicts the amino acid sequence of hinge heavy chain constant region (HC) of the heavy chain of humanized antibody hACl-36-3A8-Ab1 produced by Escherichia coli 3A8A12G7-H deposited on Mar. 6, 2012 as DSM 25745 and of the heavy chain of humanized antibody hACl-36-2B6-Ab1 produced by Escherichia coli 2B6A10C11-H deposited on Mar. 6, 2012 as DSM 25743.

Figures 1, 6A:
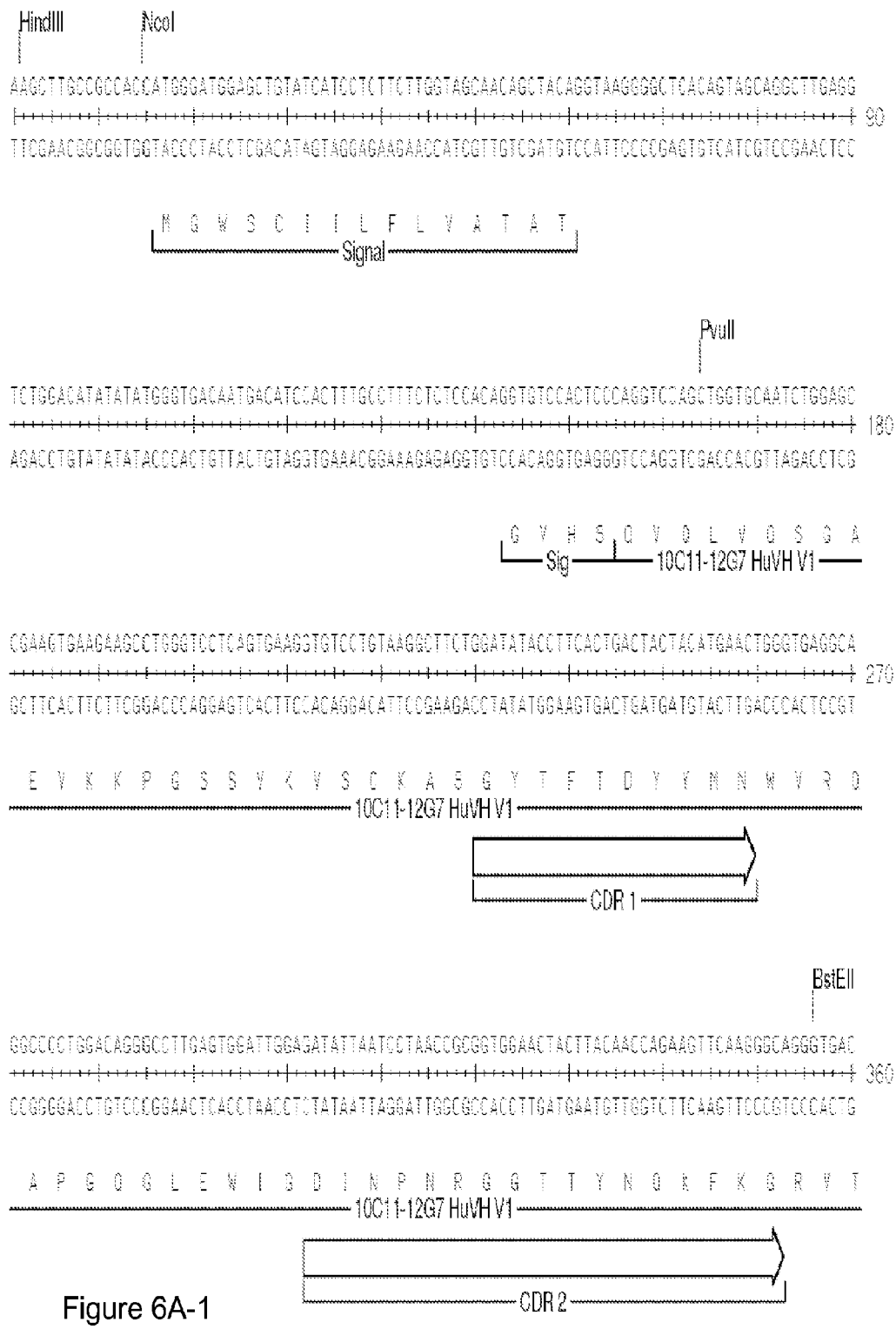
Figure 6B-1:
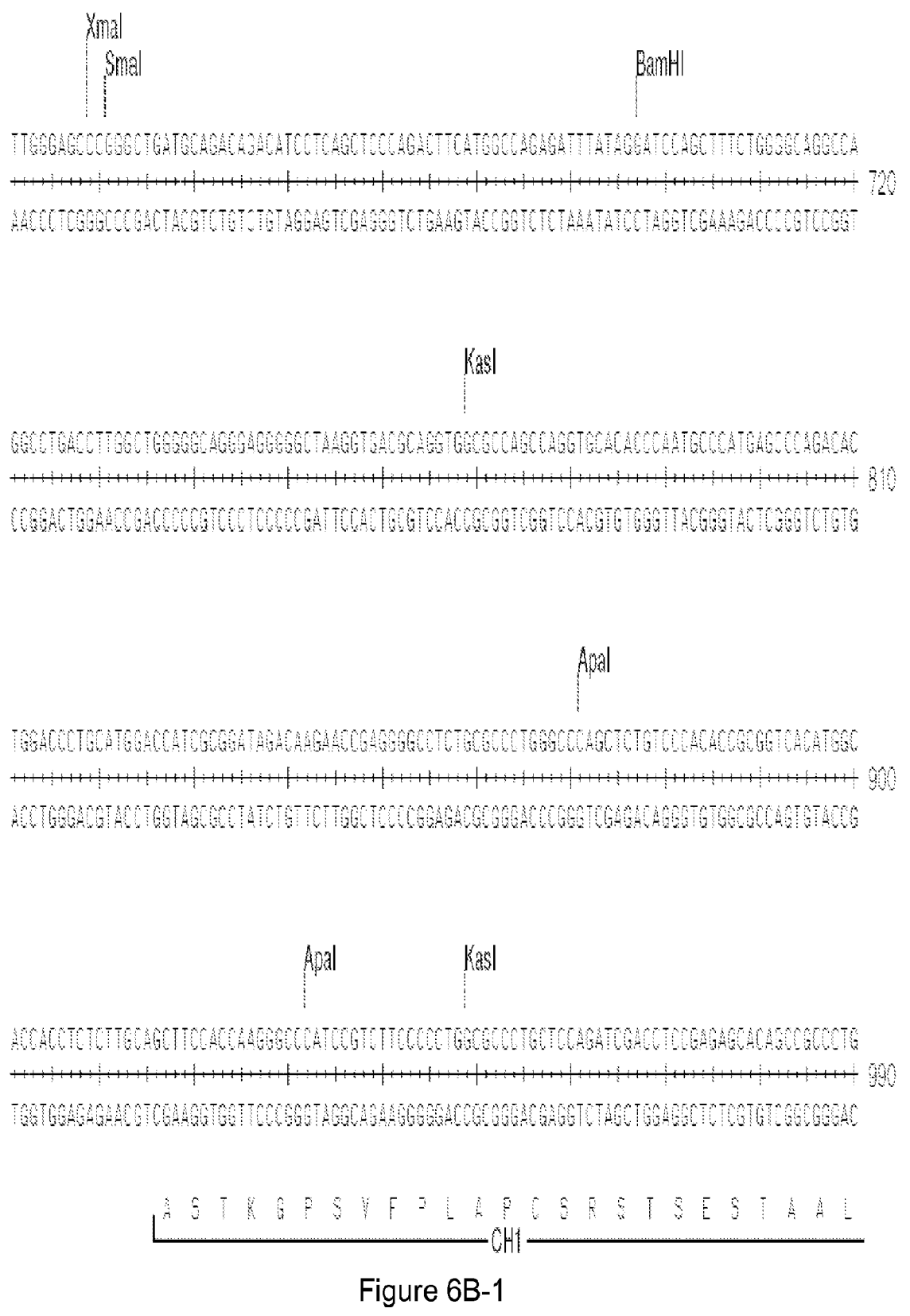
Figure 6B-2:
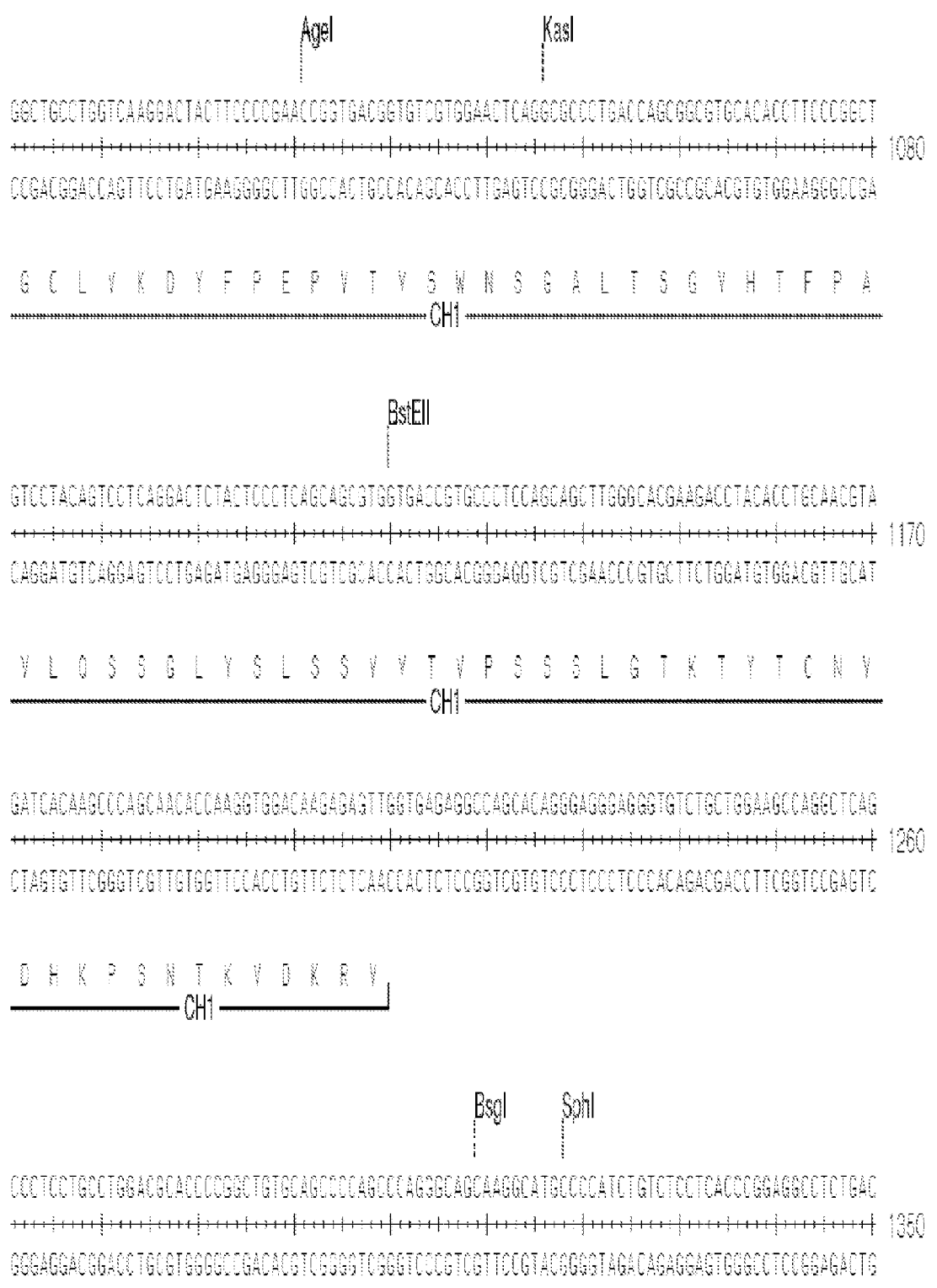
Figure 6C-1:
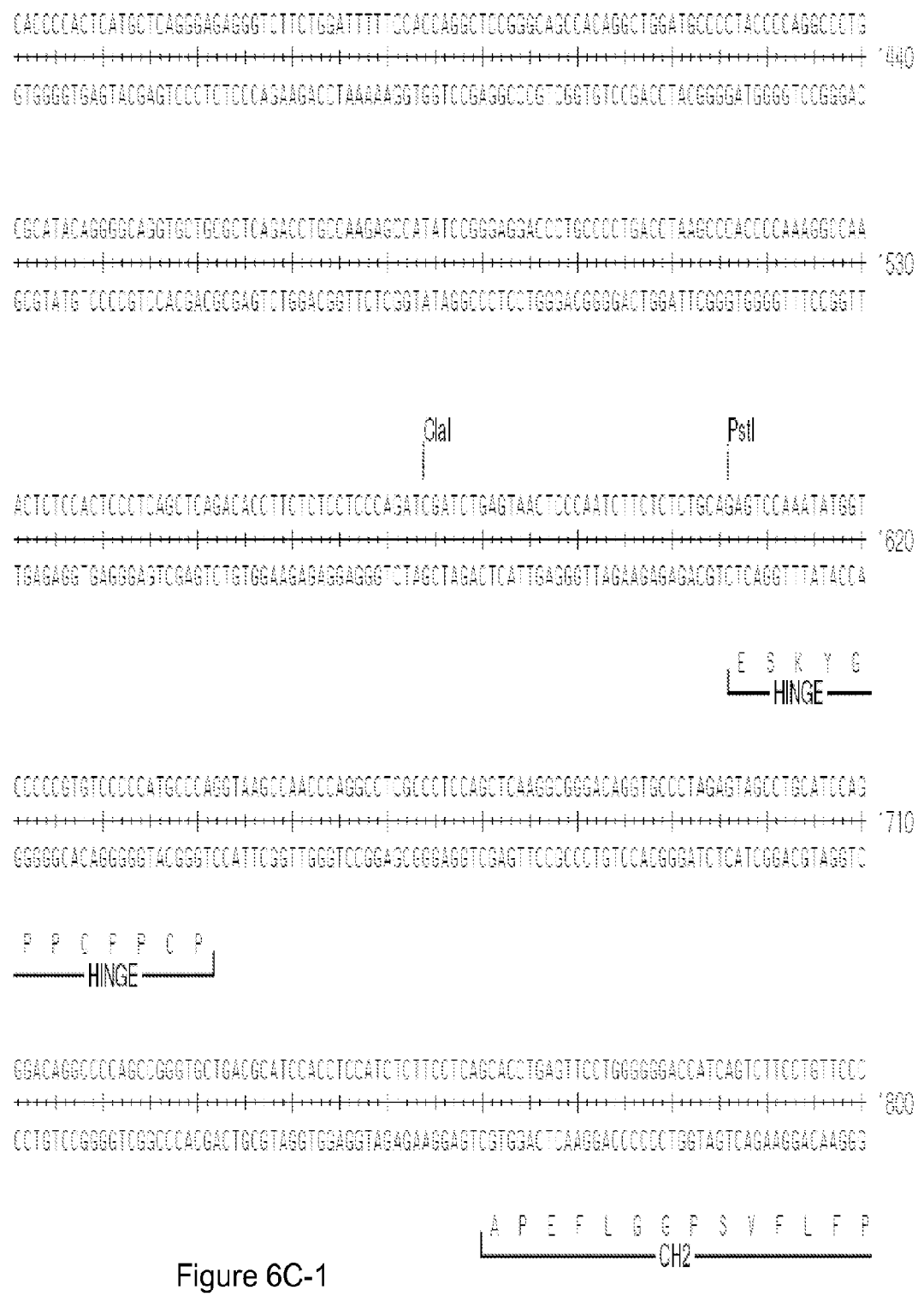
Figure 6C-2:
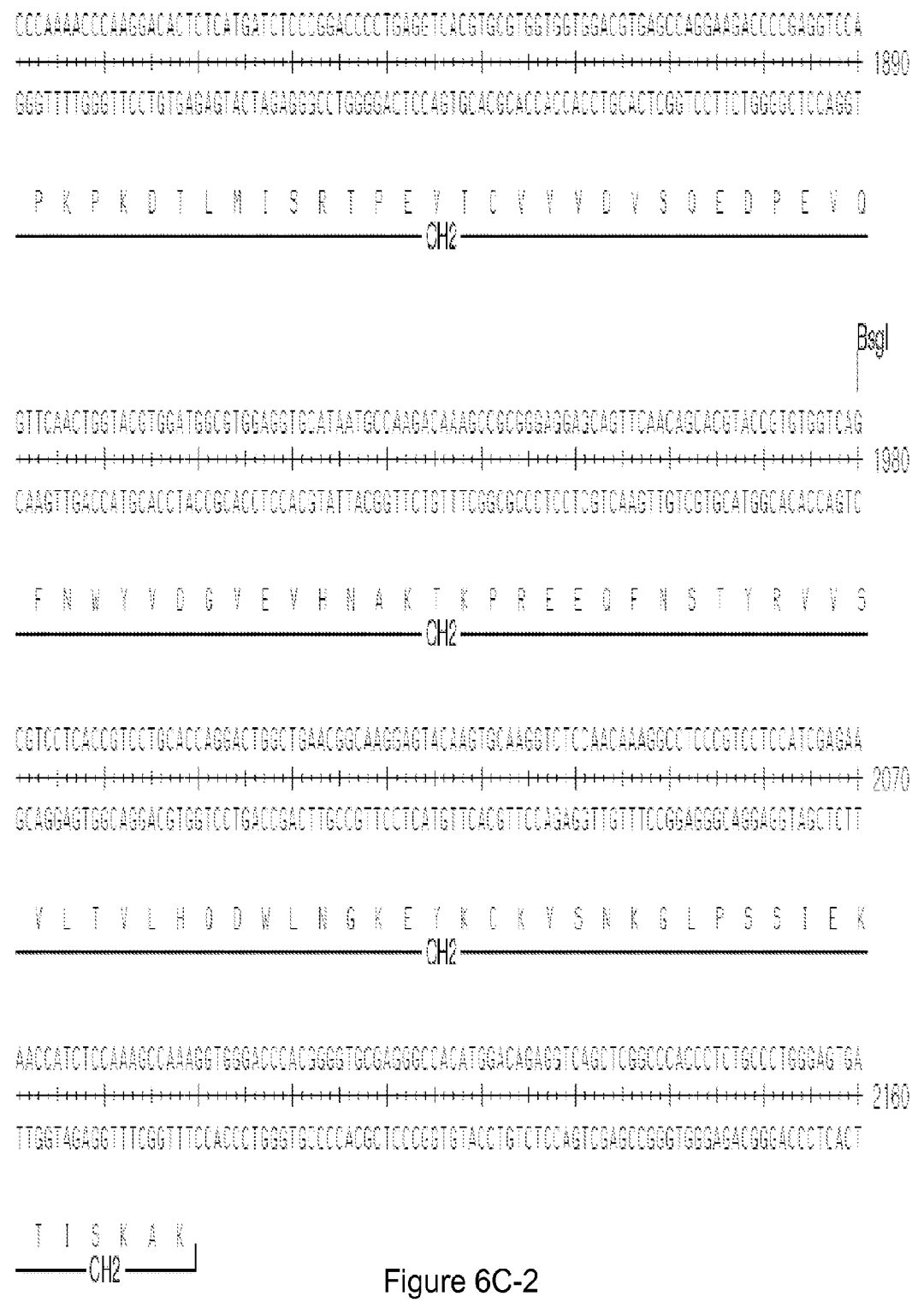

SEQ ID NO: 16 depicts the amino acid sequence of CH2 heavy chain constant region (HC) of the heavy chain of humanized antibody hACl-36-3A8-Ab1 produced by Escherichia coli 3A8A12G7-H deposited on Mar. 6, 2012 as DSM 25745 and of the heavy chain of humanized antibody hACl-36-2B6-Ab1 produced by Escherichia coli 2B6A10C11-H deposited on Mar. 6, 2012 as DSM 25743. The amino acid sequence of CH2 heavy chain constant region (HC) of the heavy chain of humanized antibody hACl-36-3A8-Ab1 is also depicted in FIG. 6C.

SEQ ID NO: 17 depicts the amino acid sequence of CH3 heavy chain constant region (HC) of the heavy chain of humanized antibody hACl-36-3A8-Ab1 produced by Escherichia coli 3A8A12G7-H deposited on Mar. 6, 2012 as DSM 25745 and of the heavy chain of humanized antibody hACl-36-2B6-Ab1 produced by Escherichia coli 2B6A10C11-H deposited on Mar. 6, 2012 as DSM 25743. SEQ ID NO: 17 depicts the amino acid sequence of CH3 heavy chain constant region (HC) of the heavy chain of humanized antibody hACl-36-3A8-Ab1 which has a deletion of the C-terminal lysine (des-K).

Figures 2, 4A:
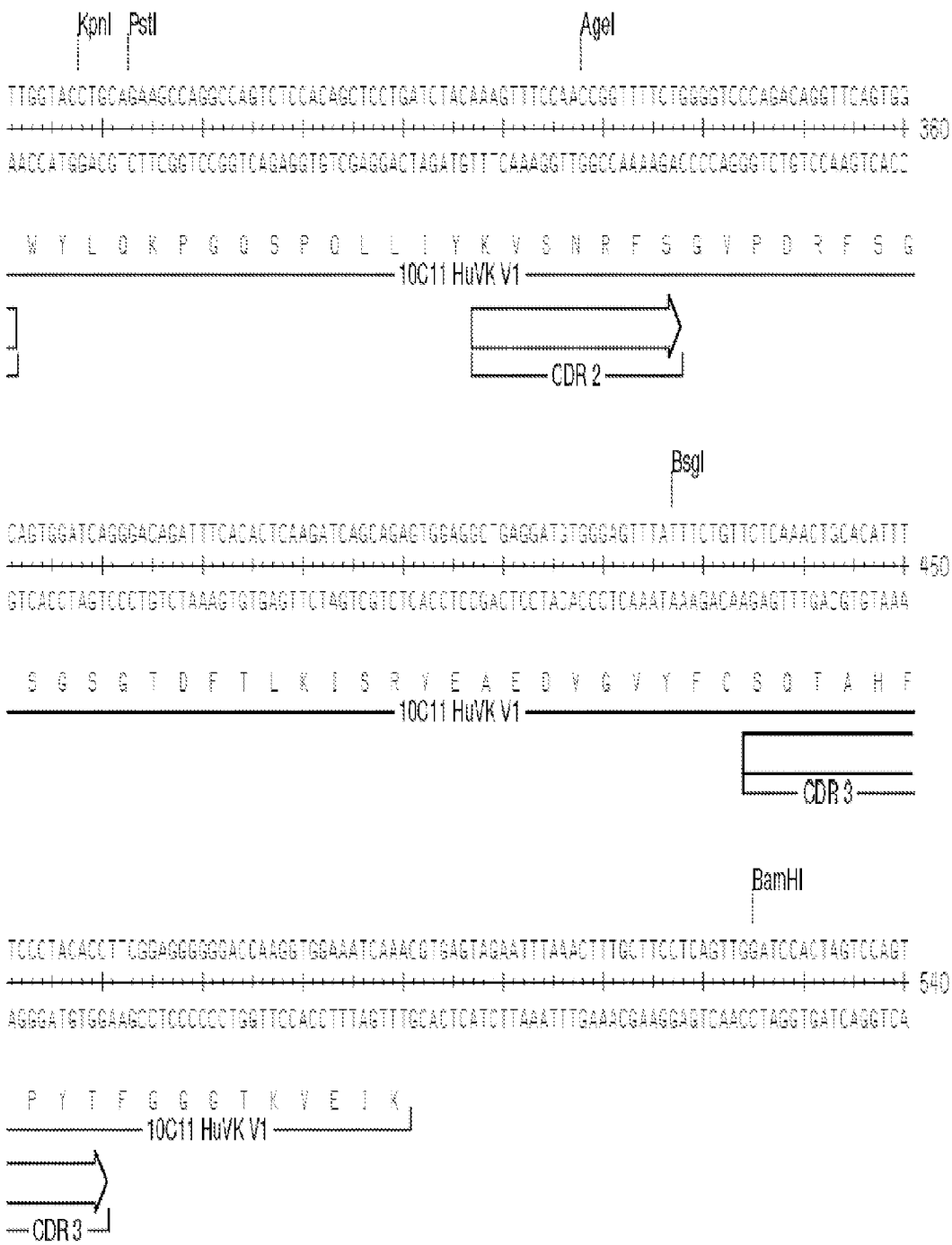
Figures 1, 4B:
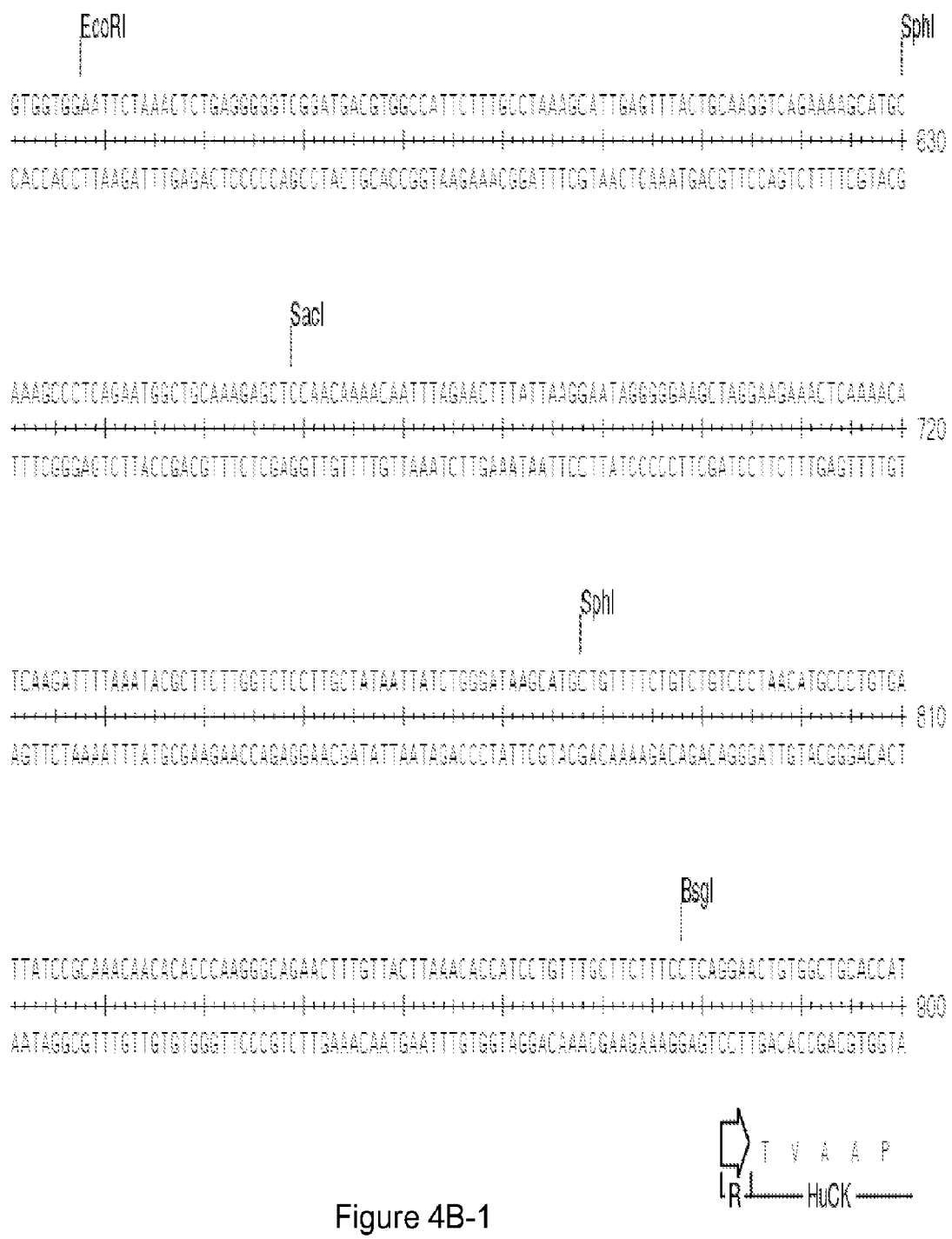
Figure 4C-1:
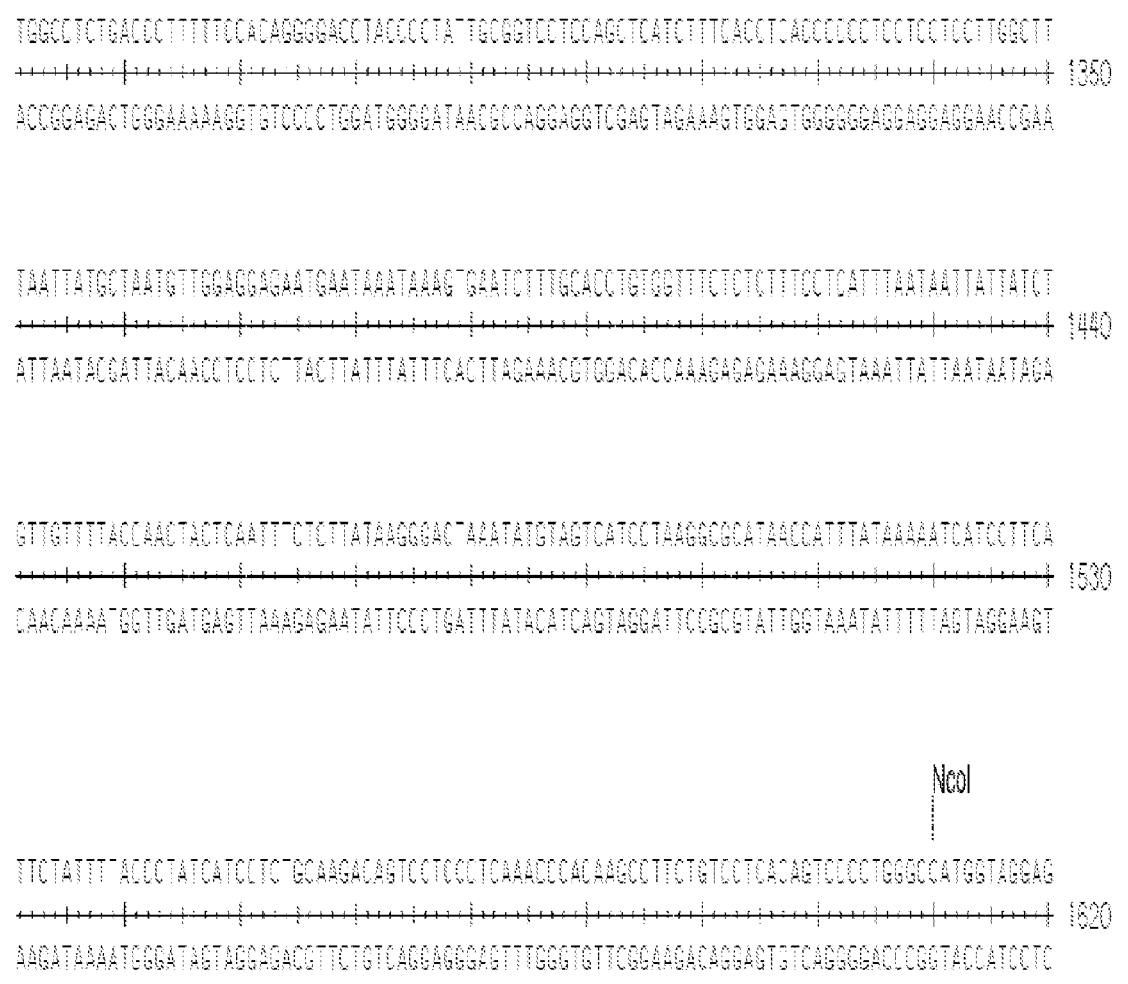
Figure 4C-2:
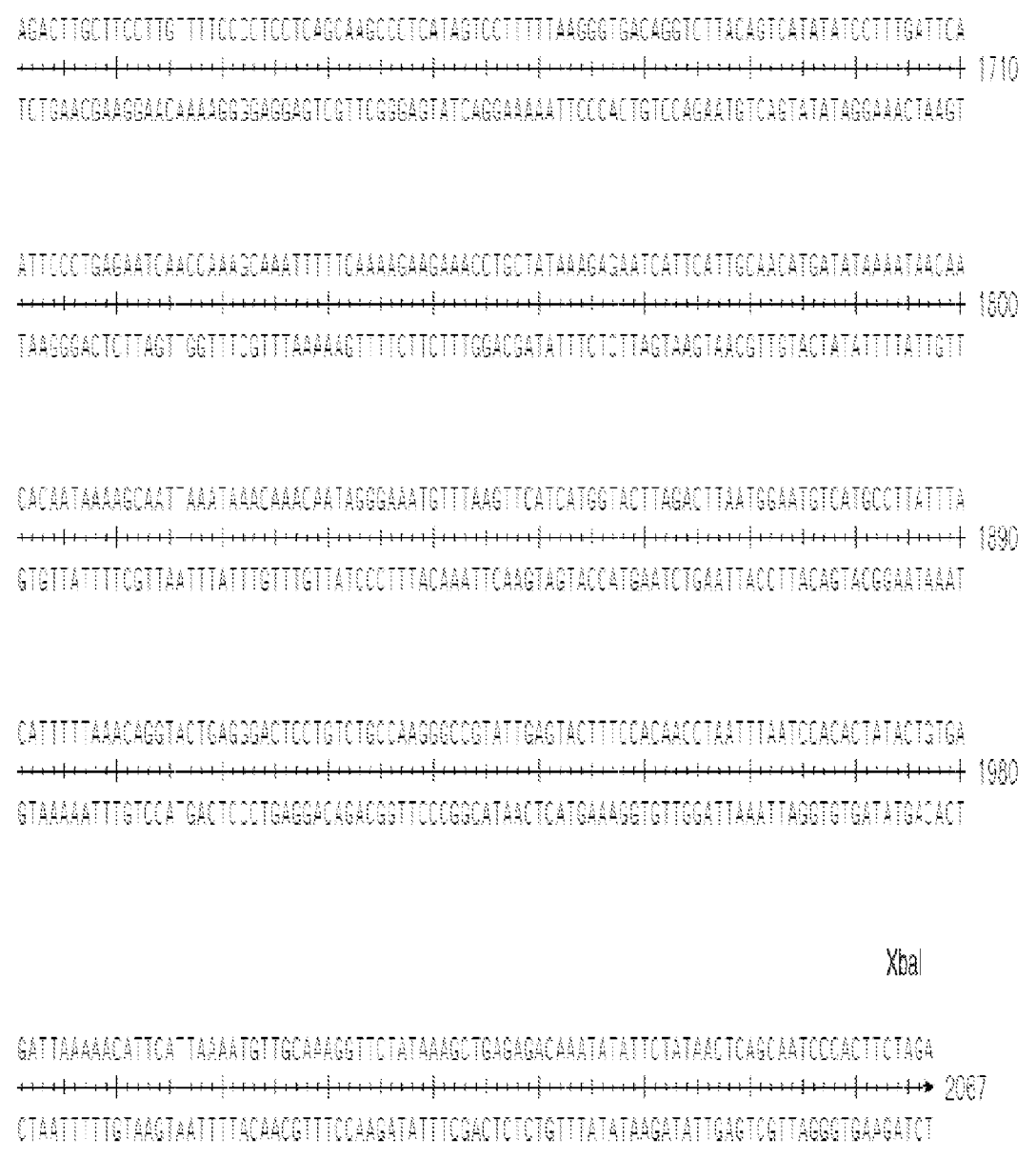
Figure 5A-1:
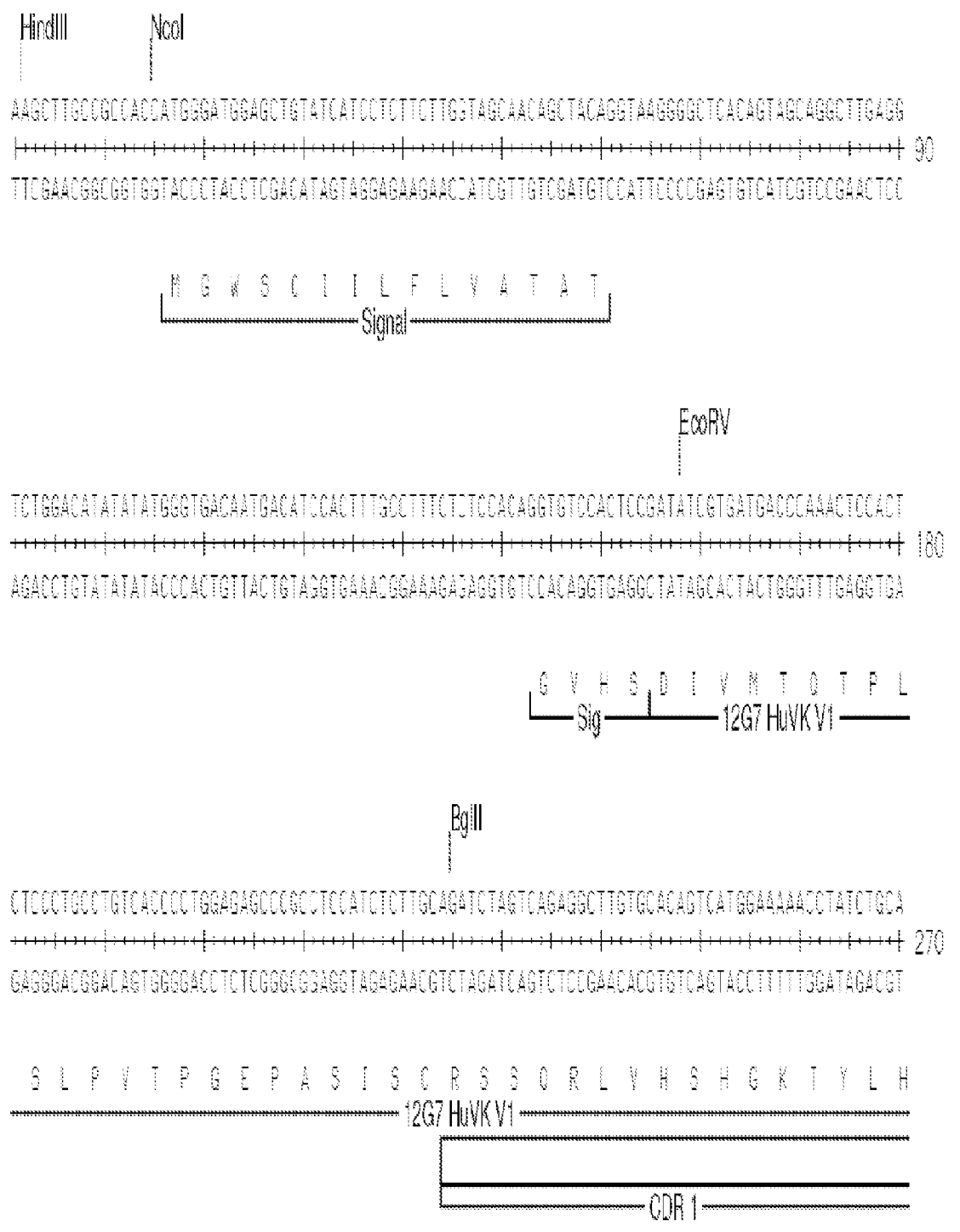

SEQ ID NO: 18 depicts the amino acid sequence of light chain constant region (LC) of humanized antibody hACl-36-3A8-Ab1 produced by Escherichia coli 3A8A12G7-H deposited on Mar. 6, 2012 as DSM 25745 and of the light chain constant region (LC) of humanized antibody hACl-36-2B6-Ab1 produced by Escherichia coli 2B6A10C11-H deposited on Mar. 6, 2012 as DSM 25743. The amino acid sequence of light chain constant region (LC) of humanized antibody hACl-36-3A8-Ab1 is also depicted in FIGS. 4B and 5B.

SEQ ID NO: 19 depicts longest isoform of human Tau (441aa), also called Tau40.

SEQ ID NO: 20 depicts the amino acid sequence of heavy chain variable region (HCVR) of humanized antibody hACl-36-3A8-Ab1.v2.

SEQ ID NO: 21 depicts the amino acid sequence of heavy chain variable region (HCVR) of humanized antibody hACl-36-2B6-Ab1.v2.

Figure 5C-2:
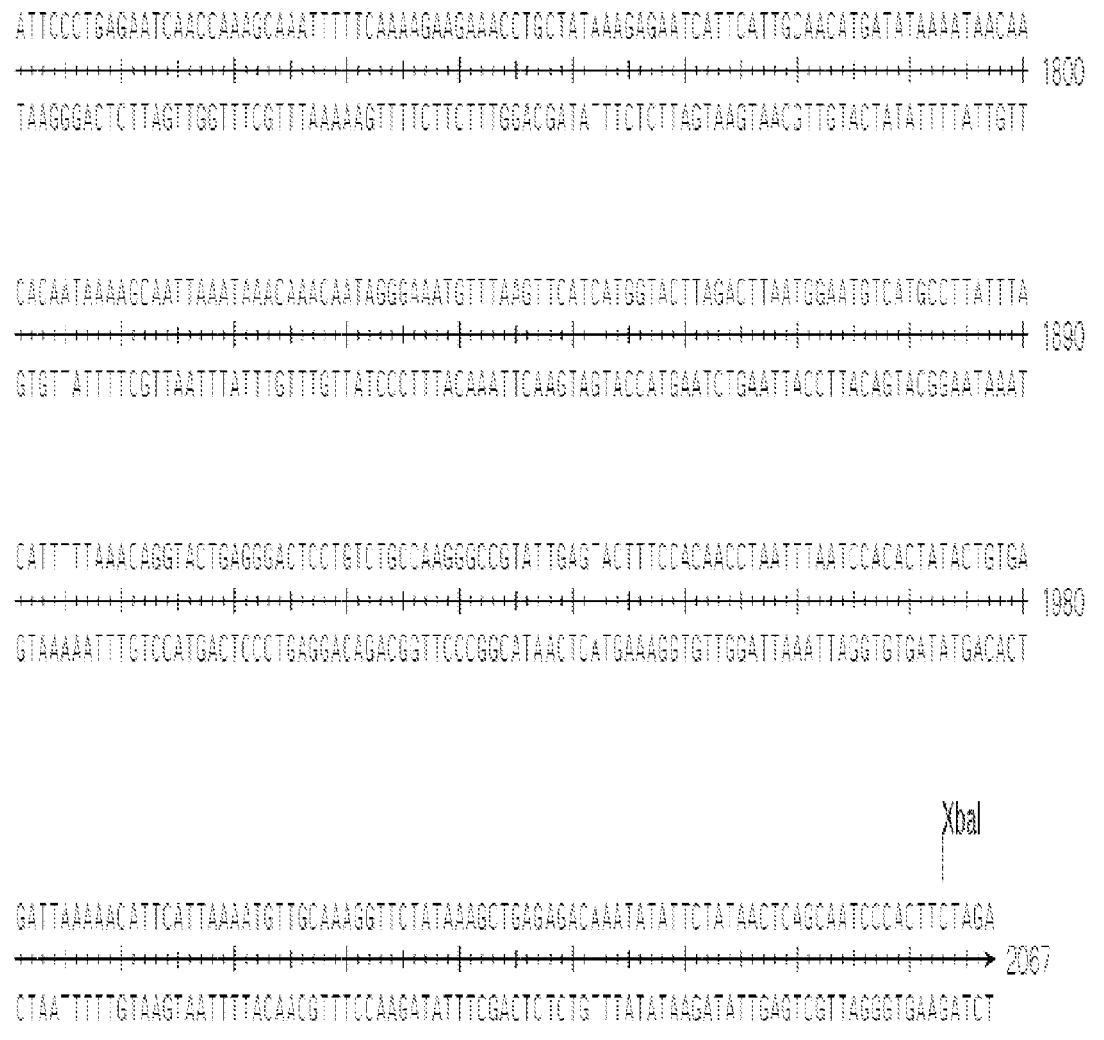

SEQ ID NO: 22 depicts the amino acid sequence of light chain (L) of the following humanized antibodies: hACl-36-3A8-Ab1 (IgG4), hACl-36-3A8-Ab1.v2 (IgG4), hACl-36-3A8-Ab1.v3 (IgG1), and hACl-36-3A8-Ab1.v4 (IgG1 N297G). The amino acid sequence of light chain (L) of hACl-36-3A8-Ab1 (IgG4), hACl-36-3A8-Ab1.v2 (IgG4), hACl-36-3A8-Ab1.v3 (IgG1), and hACl-36-3A8-Ab1.v4 (IgG1 N297G) is also depicted in FIG. 5.

SEQ ID NO: 23 depicts the amino acid sequence of light chain (L) of the following humanized antibodies: hACl-36-2B6-Ab1 (IgG4), hACl-36-2B6-Ab1.v2 (IgG4), hACl-36-2B6-Ab1.v3 (IgG1), and hACl-36-2B6-Ab1.v4 (IgG1 N297G). The amino acid sequence of light chain (L) of hACl-36-2B6-Ab1 (IgG4), hACl-36-2B6-Ab1.v2 (IgG4), hACl-36-2B6-Ab1.v3 (IgG1), and hACl-36-2B6-Ab1.v4 (IgG1 N297G) is also depicted in FIG. 4.

SEQ ID NO: 24 depicts the amino acid sequence of heavy chain (H) of humanized antibody hACl-36-3A8-Ab1 (IgG4). The amino acid sequence of heavy chain (H) of humanized antibody hACl-36-3A8-Ab1 (IgG4) is also depicted in FIG. 6.

SEQ ID NO: 25 depicts the amino acid sequence of heavy chain (H) of humanized antibody hACl-36-2B6-Ab1 (IgG4). Note: SEQ ID NO 25 is the same as SEQ ID NO: 24, and it is also depicted in FIG. 6.

SEQ ID NO: 26 depicts the amino acid sequence of heavy chain (H) of humanized antibody hACl-36-3A8-Ab1.v2 (IgG4).

SEQ ID NO: 27 depicts the amino acid sequence of heavy chain (H) of humanized antibody hACl-36-3A8-Ab1.v3 (IgG1).

SEQ ID NO: 28 depicts the amino acid sequence of heavy chain (H) of humanized antibody hACl-36-3A8-Ab1.v4 (IgG1 N297G).

SEQ ID NO: 29 depicts the amino acid sequence of heavy chain (H) of humanized antibody hACl-36-2B6-Ab1.v2 (IgG4).

SEQ ID NO: 30 depicts the amino acid sequence of heavy chain (H) of humanized antibody hACl-36-2B6-Ab1.v3 (IgG1).

SEQ ID NO: 31 depicts the amino acid sequence of heavy chain (H) of humanized antibody hACl-36-2B6-Ab1.v4 (IgG1 N297G).

DEFINITION OF TERMS

The terms "polypeptide", "peptide", and "protein", as used herein, are interchangeably and are defined to mean a biomolecule composed of amino acids linked by a peptide bond.

The terms "a", "an" and "the" as used herein are defined to mean "one or more" and include the plural unless the context is inappropriate.

The term "peptides," or "binding peptide" are used herein interchangeably and refer to chains of amino acids (typically L-amino acids) whose alpha carbons are linked through peptide bonds formed by a condensation reaction between the carboxyl group of the alpha carbon of one amino acid and the amino group of the alpha carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free alpha-amino group on the amino acid at the amino terminal of the peptide, or to the alpha-amino group (imino group when participating in a peptide bond) of an amino acid at any other location within the peptide. Similarly, the term "carboxy terminus" (abbreviated C-terminus) refers to the free carboxyl group on the amino acid at the carboxy terminus of a peptide, or to the carboxyl group of an amino acid at any other location within the peptide. A binding peptide may constitutes antibodies such as polyclonal or monoclonal antibodies, human or humanized antibodies, diabodies, camelid antibodies, etc, or functional parts thereof as defined herein.

The terms "functional fragment thereof" or "fragment" as used herein refer to a functional peptide fragment, i.e. to a part or portion of an antibody or antibody chain comprising fewer amino acid residues than an intact or complete antibody or antibody chain, but has essentially the same (biological) activity as the antibody from which it is derived, i.e. said fragments are still capable of eliciting a highly specific, particularly a conformation specific, immune response in an organism, but particularly within an animal, particularly a mammal or a human, which is highly effective and capable of preventing or alleviating tauopathies, or the symptoms associated with tauopathies. In particular, said fragments still contain the specific pathological phospho-epitope or -epitopes of the tau peptide, as used and defined herein. Fragments can be obtained via chemical or enzymatic treatment of an intact or complete antibody or antibody chain. Fragments can also be obtained by recombinant means. Exemplary fragments include Fab, Fab', F(ab')2, Fabc and/or Fv fragments. The term "antigen-binding fragment" refers to a polypeptide fragment of an immunoglobulin or antibody that binds antigen or competes with intact antibody (i.e., with the intact antibody from which they were derived) for antigen binding (i.e., specific binding).

Binding fragments are produced by recombinant DNA techniques, or by enzymatic or chemical cleavage of intact immunoglobulins. Binding fragments include Fab, Fab', F(ab')$_2$, Fabc, Fv, single chains, and single-chain antibodies.

"Fragment" also refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino acid residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of another polypeptide. In a specific embodiment, a fragment of a polypeptide retains at least one function of the polypeptide.

Typically, the amino acids making up a peptide are numbered in order, starting at the amino terminal and increasing in the direction toward the carboxy terminal of the peptide. Thus, when one amino acid is said to "follow" another, that amino acid is positioned closer to the carboxy terminal of the peptide than the preceding amino acid.

The term "residue" is used herein to refer to an amino acid that is incorporated into a peptide by an amide bond. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

The phrase "consisting essentially of" is used herein to exclude any elements that would substantially alter the essential properties of the peptides to which the phrase refers. Thus, the description of a peptide "consisting essentially of . . ." excludes any amino acid substitutions, additions, or deletions that would substantially alter the biological activity of that peptide.

Furthermore, one of skill will recognize that, as mentioned above, individual substitutions, deletions or additions which alter, add or delete a single amino acid or a small percentage of amino acids (typically less than 5%, more typically less than 1%) in an encoded sequence are conservatively modified variations where the alterations result in the substitution of an amino acid with a chemically similar amino acid. Conservative substitution tables providing functionally similar amino acids are well known in the art. The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (V), Tryptophan (W).

The phrases "isolated" or "biologically pure" refer to material which is substantially or essentially free from components which normally accompany it as found in its native state. Thus, the peptides described herein do not contain materials normally associated with their in situ environment. Typically, the isolated, immunogenic peptides described herein are at least about 80% pure, usually at least about 90%, and preferably at least about 95% as measured by band intensity on a silver stained gel.

Protein purity or homogeneity may be indicated by a number of methods well known in the art, such as polyacrylamide gel electrophoresis of a protein sample, followed by visualization upon staining. For certain purposes high resolution will be needed and HPLC or a similar means for purification utilized.

When the immunogenic peptides are relatively short in length (i.e., less than about 50 amino acids), they are often synthesized using standard chemical peptide synthesis techniques.

Solid phase synthesis in which the C-terminal amino acid of the sequence is attached to an insoluble support followed by sequential addition of the remaining amino acids in the sequence is a preferred method for the chemical synthesis of the immunogenic peptides described herein. Techniques for solid phase synthesis are known to those skilled in the art.

Alternatively, the immunogenic peptides described herein are synthesized using recombinant nucleic acid methodology. Generally, this involves creating a nucleic acid sequence that encodes the peptide, placing the nucleic acid in an expression cassette under the control of a particular promoter, expressing the peptide in a host, isolating the expressed peptide or polypeptide and, if required, renaturing the peptide. Techniques sufficient to guide one of skill through such procedures are found in the literature.

Once expressed, recombinant peptides can be purified according to standard procedures, including ammonium sulfate precipitation, affinity columns, column chromatography, gel electrophoresis and the like. Substantially pure compositions of about 50% to 95% homogeneity are preferred, and 80% to 95% or greater homogeneity is most preferred for use as therapeutic agents.

One of skill in the art will recognize that after chemical synthesis, biological expression or purification, the immunogenic peptides may possess a conformation substantially different than the native conformations of the constituent peptides. In this case, it is often necessary to denature and reduce the antiproliferative peptide and then to cause the peptide to re-fold into the preferred conformation. Methods of reducing and denaturing proteins and inducing re-folding are well known to those of skill in the art.

Antigenicity of the purified protein may be confirmed, for example, by demonstrating reaction with immune serum, or with antisera produced against the protein itself.

The terms "detecting" or "detected" as used herein mean using known techniques for detection of biologic molecules such as immunochemical or histological methods and refer to qualitatively or quantitatively determining the presence or concentration of the biomolecule under investigation.

By "isolated" is meant a biological molecule free from at least some of the components with which it naturally occurs.

The terms "antibody" or "antibodies" as used herein are art-recognized terms and are understood to refer to molecules or active fragments of molecules that bind to known antigens, particularly to immunoglobulin molecules and to immunologically active portions of immunoglobulin molecules, i.e. molecules that contain a binding site that specifically binds an antigen. An immunoglobulin is a protein comprising one or more polypeptides substantially encoded by the immunoglobulin kappa and lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Also subclasses of the heavy chain are known. For example, IgG heavy chains in humans can be any of IgG1, IgG2, IgG3 and IgG4 subclass. The immunoglobulin according to the invention can be of any class (IgG, IgM, IgD, IgE, IgA and IgY) or subclass (IgG1, IgG2, IgG3, IgG4, IgA1 and IgA2) of immunoglobulin molecule. In one embodiment, IgG heavy chain is IgG1 N297G comprising an asparagine to glycine substitution at position 297 of the Fc region.

Antibodies with reduced effector function include those with substitution of one or more of Fc region residues 238, 265, 269, 270, 297, 327 and 329 (U.S. Pat. No. 6,737,056) according to the EU numbering system. Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., J. Biol. Chem. 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. J. Immunol. 164: 4178-4184 (2000).

Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, Nature 322:738-40 (1988); U.S. Pat. No. 5,648,260; U.S. Pat. No. 5,624,821; and WO 94/29351 concerning other examples of Fc region variants.

As used herein "specifically binds" in reference to an antibody means that the antibody binds to its target antigen with greater affinity that it does to a structurally different antigen(s).

A typical immunoglobulin structural unit is known to comprise a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as full length intact antibodies or as a number of well-characterized fragments produced by digestion with various peptidases or chemicals. Thus, for example, pepsin digests an antibody below the disulfide linkages in the hinge region to produce $F(ab')_2$, a dimer of Fab which itself is a light chain joined to $V_H$-$CH_1$ by a disulfide bond. The $F(ab')_2$ may be reduced under mild conditions to break the disulfide linkage in the hinge region thereby converting the $F(ab')_2$ dimer into an Fab' monomer. The Fab' monomer is essentially a Fab fragment with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that any of a variety of antibody fragments may be synthesized de novo either chemically or by utilizing recombinant DNA methodology. Thus, the term antibody, as used herein also includes antibody fragments either produced by the modification of whole antibodies or synthesized de novo or antibodies and fragments obtained by using recombinant DNA methodologies.

"Antibodies" are intended within the scope of the present invention to include monoclonal antibodies, polyclonal, chimeric, single chain, bispecific, simianized, human and humanized antibodies, camelid antibodies, diabodies, as well as functional parts or active fragments thereof. Examples of active fragments of molecules that bind to known antigens include separated light and heavy chains, Fab, Fab/c, Fv, Fab', and $F(ab')_2$ fragments, including the products of an Fab immunoglobulin expression library and epitope-binding fragments of any of the antibodies and fragments mentioned above.

These active fragments can be derived from an antibody of the present invention by a number of techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. J. Nucl. Med. 23:1011-1019 (1982); Rousseaux et al. Methods Enzymology, 121:663-69, Academic Press, (1986).

Recombinant antibodies may be conventional full length antibodies, active antibody fragments known from proteolytic digestion, unique active antibody fragments such as Fv or single chain Fv (scFv), domain deleted antibodies, and the like. An Fv antibody is about 50 KDa in size and comprises the variable regions of the light and heavy chain. A single chain Fv ("scFv") polypeptide is a covalently linked VH::VL heterodimer which may be expressed from a nucleic acid including VH- and VL-encoding sequences either joined directly or joined by a peptide-encoding linker. See Huston, et al. (1988) Proc. Nat. Acad. Sci. USA, 85:5879-5883. A number of structures for converting the naturally aggregated, but chemically separated light and heavy polypeptide chains from an antibody V region into an scFv molecule which will fold into a three dimensional structure substantially similar to the structure of an antigen-binding site. See, e.g. U.S. Pat. Nos. 5,091,513, 5,132,405 and 4,956,778.

The combining site refers to the part of an antibody molecule that participates in antigen binding. The antigen binding site is formed by amino acid residues of the N-terminal variable ("V") regions of the heavy ("H") and light ("L") chains. The antibody variable regions comprise three highly divergent stretches referred to as "hypervariable regions" or "complementarity determining regions" (CDRs) which are interposed between more conserved flanking stretches known as "framework regions" (FRs). In an antibody molecule, the three hypervariable regions of a light chain (LCDR1, LCDR2, and LCDR3) and the three hypervariable regions of a heavy chain (HCDR1, HCDR2 and HCDR3) are disposed relative to each other in three dimensional space to form an antigen binding surface or pocket. The antibody combining site therefore represents the amino acids that make up the CDRs of an antibody and any framework residues that make up the binding site pocket.

The identity of the amino acid residues in a particular antibody that make up the combining site can be determined using methods well known in the art. For example, antibody CDRs may be identified as the hypervariable regions originally defined by Kabat et al. (see, "Sequences of Proteins of Immunological Interest," E. Kabat et al., U.S. Department of Health and Human Services; Johnson, G and Wu, T T (2001) Kabat Database and its applications: future directions. Nucleic Acids Research, 29: 205-206; http://immuno.bme.nwa.edu). The positions of the CDRs may also be identified as the structural loop structures originally described by Chothia and others, (see Chothia and Lesk, J. Mol. Biol. 196, 901 (1987), Chothia et al., Nature 342, 877 (1989), and Tramontano et al., J. Mol. Biol. 215, 175 (1990)). Other methods include the "AbM definition" which is a compromise between Kabat and Chothia and is derived using Oxford Molecular's AbM antibody modeling software (now Accelrys) or the "contact definition" of CDRs by Macallum et al., ("Antibody-antigen interactions: contact analysis and binding site topography," J Mol Biol. 1996 Oct. 11; 262(5): 732-45). The following chart identifies CDRs based upon various known definitions.

| Loop | Kabat | AbM | Chothia | Contact |
|------|-------|-----|---------|---------|
| L1 | L24 - L34 | L24 - L34 | L24 - L34 | L30 - L36 |
| L2 | L50 - L56 | L50 - L56 | L50 - L56 | L46 - L55 |
| L3 | L89 - L97 | L89 - L97 | L89 - L97 | L89 - L96 |
| H1 | H31 - H35B | H26 - H35B | H26 - H32..34 | H30 - H35B |
| | | | (Kabat Numbering) | |
| H1 | H31 - H35 | H26 - H35 | H26 - H32 | H30 - H35 |
| | | | (Chothia Numbering) | |
| H2 | H50 - H65 | H50 - H58 | H52 - H56 | H47 - H58 |
| H3 | H95 - H102 | H95 - H102 | H95 - H102 | H93 - H101 |

General guidelines by which one may identify the CDRs in an antibody from sequence alone are as follows:

LCDR1:
Start—Approximately residue 24.
Residue before is always a Cys.
Residue after is always a Trp. Typically TRP is followed with TYR-GLN, but also may be followed by LEU-GLN, PHE-GLN, or TYR-LEU.
Length is 10 to 17 residues.

LCDR2:
Start—16 residues after the end of L1
Sequence before is generally ILE-TYR, but also may be VAL-TYR, ILE-LYS, or ILE-PHE.
Length is generally 7 residues.

LCDR3:
Start—generally 33 residues after end of L2.
Residue before is a Cys.
Sequence after is PHE-GLY-X-GLY.
Length is 7 to 11 residues.

HCDR1:
Start—at approximately residue 26 (four residues after a CYS) [Chothia/AbM definition] Kabat definition starts 5 residues later.
Sequence before is CYS-X-X-X.
Residues after is a TRP, typically followed by VAL, but also followed by ILE, or ALA.
Length is 10 to 12 residues under AbM definition while Chothia definition excludes the last 4 residues.

HCDR2:
Start—15 residues after the end of Kabat/AbM definition of CDR-H1.
Sequence before typically LEU-GLU-TRP-ILE-GLY (SEQ ID NO. 1), but a number of variations are possible.
Sequence after is LYS/ARG-LEU/ILE/VAL/PHE/THR/ALA-THR/SER/ILE/ALA
Length is 16 to 19 residues under Kabat definition (AbM definition ends 7 residues earlier).

HCDR3:
Start—33 residues after end of CDR-H2 (two residues after a CYS).
Sequence before is CYS-X-X (typically CYS-ALA-ARG).
Sequence after is TRP-GLY-X-GLY.
Length is 3 to 25 residues.

The identity of the amino acid residues in a particular antibody that are outside the CDRs, but nonetheless make up part of the combining site by having a side chain that is part of the lining of the combining site (i.e., it is available to linkage through the combining site), can be determined using methods well known in the art such as molecular modelling and X-ray crystallography. See e.g., Riechmann et al., (1988) Nature, 332:323-327.

Chimeric antibodies are those in which one or more regions of the antibody are from one species of animal and one or more regions of the antibody are from a different species of animal. A preferred chimeric antibody is one which includes regions from a primate immunoglobulin. A chimeric antibody for human clinical use is typically understood to have variable regions from a non-human animal, e.g. a rodent, with the constant regions from a human In contrast, a humanized antibody uses CDRs from the non-human antibody with most or all of the variable framework regions from and all the constant regions from a human immunoglobulin. A human chimeric antibody is typically understood to have the variable regions from a rodent. A typical human chimeric antibody has human heavy constant regions and human light chain constant regions with the variable regions of both the heavy and light coming from a rodent antibody. A chimeric antibody may include some changes to a native amino acid sequence of the human constant regions and the native rodent variable region sequence. Chimeric and humanized antibodies may be prepared by methods well known in the art including CDR grafting approaches (see, e.g., U.S. Pat. Nos. 5,843,708; 6,180,370; 5,693,762; 5,585,089; 5,530,101), chain shuffling strategies (see e.g., U.S. Pat. No. 5,565,332; Rader et al., Proc. Natl. Acad. Sci. USA (1998) 95:8910-8915), molecular modelling strategies (U.S. Pat. No. 5,639,641), and the like.

A "humanized antibody" as used herein in the case of a two chain antibody is one where at least one chain is humanized. A humanized antibody chain has a variable region where one or more of the framework regions are human. A humanized antibody which is a single chain is one where the chain has a variable region where one or more of the framework regions are human. The non-human portions of the variable region of the humanized antibody chain or fragment thereof is derived from a non-human source, particularly a non-human antibody, typically of rodent origin. The non-human contribution to the humanized antibody is typically provided in form at least one CDR region which is interspersed among framework regions derived from one (or more) human immunoglobulin(s). In addition, framework support residues may be altered to preserve binding affinity. The humanized antibody may further comprise constant regions (e.g., at least one constant region or portion thereof, in the case of a light chain, and preferably three constant regions in the case of a heavy chain). The constant regions of a humanized antibody if present generally are human.

The humanized antibody may further comprise constant regions (e.g., at least one constant region or portion thereof, in the case of a light chain, and preferably three constant regions in the case of a heavy chain). The constant regions of a humanized antibody if present generally are human.

A humanized antibody may further refer to an antibody having a variable region where one or more of its framework regions have human or primate amino acids. In addition, framework support residues may be altered to preserve binding affinity. Methods to obtain "humanized antibodies" are well known to those skilled in the art. (see, e.g., Queen et al., Proc. Natl Acad Sci USA, 86:10029-10032 (1989), Hodgson et al., Bio/Technoloy, 9:421 (1991)).

A "humanized antibody" may also be obtained by a novel genetic engineering approach that enables production of affinity-matured humanlike polyclonal antibodies in large animals such as, for example, rabbits (http://www.rctech-.com/bioventures/therapeutic.php)

The term "fully human antibody" or "human" antibody is meant to refer to an antibody derived from transgenic mice carrying human antibody genes or from human cells. To the human immune system, however, the difference between "fully human", "human", and "humanized" antibodies may be negligible or nonexistent and as such all three may be of equal efficacy and safety.

The term constant region (CR) as used herein refers to constant regions genes of the immunoglobulin. The constant region genes encode the portion of the antibody molecule which confers effector functions. For Chimeric human antibodies and humanized antibodies, typically non-human (e.g., murine), constant regions are substituted by human constant regions. The constant regions of the subject chimeric or humanized antibodies are typically derived from human immunoglobulins. The heavy chain constant region can be selected from any of the five isotypes: alpha, delta, epsilon, gamma or mu. Further, heavy chains of various subclasses (such as the IgG subclasses of heavy chains) are responsible for different effector functions and thus, by choosing the desired heavy chain constant region, antibodies with desired effector function can be produced. Constant regions that may be used within the scope of this invention are gamma 1 (IgG1), particularly an Fc region of the gamma 1 (IgG1) isotype, gamma 1 N297G (IgG1 N297G), gamma 3 (IgG3) and especially gamma 4 (IgG4). The light chain constant region can be of the kappa or lambda type, preferably of the kappa type. In one embodiment the light chain constant region is the human kappa constant chain (Heiter et al. (1980) Cell 22:197-207) and the heavy constant chain is the human IgG4 constant chain.

The term "monoclonal antibody" is also well recognized in the art and refers to an antibody that is mass produced in the laboratory from a single clone and that recognizes only one antigen. Monoclonal antibodies are typically made by fusing a normally short-lived, antibody-producing B cell to a fast-growing cell, such as a cancer cell (sometimes referred to as an "immortal" cell). The resulting hybrid cell, or hybridoma, multiplies rapidly, creating a clone that produces large quantities of the antibody. For the purpose of the present invention, "monoclonal antibody" is also to be understood to comprise antibodies that are produced by a mother clone which has not yet reached full monoclonality.

The term "hybridize" as used refers to conventional hybridization conditions, preferably to hybridization conditions at which 5×SSPE, 1% SDS, 1×Denhardts solution is used as a solution and/or hybridization temperatures are between 35° C. and 70° C., preferably 65° C. After hybridization, washing is preferably carried out first with 2×SSC, 1% SDS and subsequently with 0.2×SSC at temperatures between 35° C. and 70° C., preferably at 65° C. (regarding the definition of SSPE, SSC and Denhardts solution see Sambrook et al. loc. cit.). Stringent hybridization conditions as for instance described in Sambrook et al, supra, are particularly preferred. Particularly preferred stringent hybridization conditions are for instance present if hybridization and washing occur at 65° C. as indicated above. Non-stringent hybridization conditions, for instance with hybridization and washing carried out at 45° C. are less preferred and at 35° C. even less.

"Homology" between two sequences is determined by sequence identity. If two sequences which are to be compared with each other differ in length, sequence identity preferably relates to the percentage of the nucleotide residues of the shorter sequence which are identical with the nucleotide residues of the longer sequence. Sequence identity can be determined conventionally with the use of computer programs such as the Bestfit program (Wisconsin Sequence Analysis Package, Version 8 for Unix, Genetics Computer Group, University Research Park, 575 Science Drive Madison, Wis. 53711). Bestfit utilizes the local homology algorithm of Smith and Waterman, Advances in Applied Mathematics 2 (1981), 482-489, in order to find the segment having the highest sequence identity between two sequences. When using Bestfit or another sequence alignment program to determine whether a particular sequence has for instance 95% identity with a reference sequence of the present invention, the parameters are preferably so adjusted that the percentage of identity is calculated over the entire length of the reference sequence and that homology gaps of up to 5% of the total number of the nucleotides in the reference sequence are permitted. When using Bestfit, the so-called optional parameters are preferably left at their preset ("default") values. The deviations appearing in the comparison between a given sequence and the above-described sequences of the invention may be caused for instance by addition, deletion, substitution, insertion or recombination. Such a sequence comparison can preferably also be carried out with the program "fasta20u66" (version 2.0u66, September 1998 by William R. Pearson and the University of Virginia; see also W. R. Pearson (1990), Methods in Enzymology 183, 63-98, appended examples and http://workbench.sdsc.edu/). For this purpose, the "default" parameter settings may be used.

The antibody according to the invention may be an immunoglobulin or antibody, which is understood to have each of its binding sites identical (if multivalent) or, in the alternative, may be a "bispecific" or "bifunctional antibody".

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

The term "antigen" refers to an entity or fragment thereof which can induce an immune response in an organism, particularly an animal, more particularly a mammal including a human. The term includes immunogens and regions responsible for antigenicity or antigenic determinants.

As used herein, the term "soluble" means partially or completely dissolved in an aqueous solution.

Also as used herein, the term "immunogenic" refers to substances which elicit or enhance the production of antibodies, T-cells and other reactive immune cells directed against an immunogenic agent and contribute to an immune response in humans or animals.

An immune response occurs when an individual produces sufficient antibodies, T-cells and other reactive immune cells against administered immunogenic compositions of the present invention to moderate or alleviate the disorder to be treated.

The term immunogenicity as used herein refers to a measure of the ability of an antigen to elicit an immune response (humoral or cellular) when administered to a recipient. The present invention is concerned with approaches that reduce the immunogenicity of the subject human chimeric or humanized antibodies.

Humanized antibody of reduced immunogenicity refers to a humanized antibody exhibiting reduced immunogenicity relative to the parent antibody, e.g., the murine antibody.

Humanized antibody substantially retaining the binding properties of the parent antibody refers to a humanized antibody which retains the ability to specifically bind the antigen recognized by the parent antibody used to produce such humanized antibody. Preferably the humanized antibody will exhibit the same or substantially the same antigen-binding affinity and avidity as the parent antibody. Ideally, the affinity of the antibody will not be less than 10% of the parent antibody affinity, more preferably not less than about 30%, and most preferably the affinity will not be less than 50% of the parent antibody. Methods for assaying antigen-binding affinity are well known in the art and include half-maximal binding assays, competition assays, and Scatchard analysis. Suitable antigen binding assays are described in this application.

A "back mutation" is a mutation introduced in a nucleotide sequence which encodes a humanized antibody, the mutation results in an amino acid corresponding to an amino acid in the parent antibody (e.g., donor antibody, for example, a murine antibody). Certain framework residues from the parent antibody may be retained during the humanization of the antibodies of the invention in order to substantially retain the binding properties of the parent antibody, while at the same time minimizing the potential immunogenicity of the resultant antibody. In one embodiment of the invention, the parent antibody is of mouse origin. For example, the back mutation changes a human framework residue to a parent murine residue. Examples of framework residues that may be back mutated include, but are not limited to, canonical residues, interface packing residues, unusual parent residues which are close to the binding site, residues in the "Vernier Zone" (which forms a platform on which the CDRs rest) (Foote & Winter, 1992, *J. Mol. Biol.* 224, 487-499), and those close to CDR H3.

As used herein a "conservative change" refers to alterations that are substantially conformationally or antigenically neutral, producing minimal changes in the tertiary structure of the mutant polypeptides, or producing minimal changes in the antigenic determinants of the mutant polypeptides, respectively, as compared to the native protein. When referring to the antibodies and antibody fragments of the invention, a conservative change means an amino acid substitution that does not render the antibody incapable of binding to the subject receptor. Those of ordinary skill in the art will be able to predict which amino acid substitutions can be made while maintaining a high probability of being conformationally and antigenically neutral. Such guidance is provided, for example in Berzofsky, (1985) *Science* 229:932-940 and Bowie et al. (1990) *Science* 247:1306-1310. Factors to be considered that affect the probability of maintaining conformational and antigenic neutrality include, but are not limited to: (a) substitution of hydrophobic amino acids is less likely to affect antigenicity because hydrophobic residues are more likely to be located in a protein's interior; (b) substitution of physicochemically similar, amino acids is less likely to affect conformation because the substituted amino acid structurally mimics the native amino acid; and (c) alteration of evolutionarily conserved sequences is likely to adversely affect conformation as such conservation suggests that the amino acid sequences may have functional importance. One of ordinary skill in the art will be able to assess alterations in protein conformation using well-known assays, such as, but not limited to microcomplement fixation methods (Wasserman et al. (1961) *J. Immunol.* 87:290-295; Levine et al. (1967) *Meth. Enzymol.* 11:928-936) and through binding studies using conformation-dependent monoclonal antibodies (Lewis et al. (1983) *Biochem.* 22:948-954).

The term "hybridoma" is art recognized and is understood by those of ordinary skill in the art to refer to a cell produced by the fusion of an antibody-producing cell and an immortal cell, e.g. a multiple myeloma cell. This hybrid cell is capable of producing a continuous supply of antibody. See the definition of "monoclonal antibody" above and the Examples below for a more detailed description of the method of fusion.

The term "carrier" as used herein means a structure in which antigenic peptide or supramolecular construct can be incorporated into or can be associated with, thereby presenting or exposing antigenic peptides or part of the peptide to the immune system of a human or animal. Any particle that can be suitably used in animal or human therapy such as, for example, a vesicle, a particle or a particulate body may be used as a carrier within the context of the present invention.

The term "carrier" further comprises methods of delivery wherein supramolecular antigenic construct compositions comprising the antigenic peptide may be transported to desired sites by delivery mechanisms. One example of such a delivery system utilizes colloidal metals such as colloidal gold.

Carrier proteins that can be used in the supramolecular antigenic construct compositions of the present invention include, but are not limited to, maltose binding peptide "MBP"; bovine serum albumin "BSA"; keyhole lympet hemocyanin "KLH"; ovalbumin; flagellin; thyroglobulin; serum albumin of any species; gamma globulin of any species; syngeneic cells; syngeneic cells bearing Ia antigens; and polymers of D- and/or L-amino acids.

Further, the term "therapeutically effective amount" or "pharmaceutically effective amount" refers to the amount of binding peptide which, when administered to a human or animal, is sufficient to result in a therapeutic effect in said human or animal. The effective amount is readily determined by one of ordinary skill in the art following routine procedures.

"pTau PHF", "PHF", and "paired helical filaments" are used herein synonymously and refer to pairs of filaments wound into helices with a periodicity of 160 nm visible on electron microscopy. Width varies between 10 and 22 nm. PHF are the predominant structures in neurofibrillary tangles of Alzheimer's Disease (AD) and neuropil threads. PHF may also be seen in some but not all dystrophic neurites associated with neuritic plaques. The major component of PHF is a hyperphosphorylated form of microtubule-associated protein tau. PHF may be partially composed of disulfide-linked antiparallel hyper-phosphorylated tau proteins. PHF tau may be truncated of its C-terminal 20 amino acid residues. The mechanisms underlying PHF formation are uncertain but hyper-phosphorylation of tau may disengage it from microtubules, increasing the soluble pool of tau from which PHF can be formed inside neurons.

Within the scope of the present invention, it was demonstrated that the antibody induced response to the antigenic composition according to the invention is largely T-cell independent. A nude mouse model was used in this respect and nude mice were vaccinated and antibody responses measured to evaluate the Aβ-specific antibody response induced by the antigenic composition according to the invention in the immunized nude mice. The nude mice carry the Foxn1nu mutation and as a consequence, have reduced T-cell function due to the lack of a proper thymus.

A "pharmaceutically effective amount" as used herein refers to a dose of the active ingredient in a pharmaceutical composition adequate to cure, or at least partially arrest, the symptoms of the disease, disorder or condition to be treated or any complications associated therewith.

The present invention provides binding peptides recognizing and binding to major pathological phospho-epitopes of the tau protein. In particular, the present invention provides specific antibodies against linear and conformational, simple and complex phospho-epitopes on protein tau that are believed to be responsible for synapto- and neuro-toxicity in tauopathies, including AD.

Accordingly, the present invention relates in one embodiment to a chimeric or a humanized antibody or a functional fragment thereof, which antibody recognizes and specifically binds to a phospho-epitope on a mammalian, particularly on the human Tau protein or on a fragment thereof, particularly to a pathological protein tau conformer, but, in one embodiment, does not bind to the corresponding unphosphorylated epitope and/or to non-related epitopes, wherein said binding peptide or antibody has a high binding affinity with a dissociation constant of at least 10 nM, particularly of at least 8 nM, particularly of at least 5 nM, particularly of at least 2 nM, particularly of at least 1 nM, particularly of at least 500 pM, particularly of at least 400 pM particularly of at least 300 pM, particularly of at least 200 pM, particularly of at least 100 pM, particularly of at least 50 pM.

"Soluble Tau" protein as used herein refers to proteins consisting of both completely solubilized Tau protein/peptide monomers or of Tau-like peptides/proteins, or of modified or truncated Tau peptides/proteins or of other derivates of Tau peptides/proteins monomers, and of Tau protein oligomers. "Soluble Tau" excludes particularly neurofibrillary tangles (NFT).

"Insoluble Tau" as used herein refers to multiple aggregated monomers of Tau peptides or proteins, or of Tau-like peptides/proteins, or of modified or truncated Tau peptides/proteins or of other derivates of Tau peptides/proteins forming oligomeric or polymeric structures which are insoluble both in vitro in aqueous medium and in vivo in the mammalian or human body more particularly in the brain, but particularly to multiple aggregated monomers of Tau or of modified or truncated Tau peptides/proteins or of derivatives thereof, which are insoluble in the mammalian or human body more particularly in the brain, respectively. "Insoluble Tau" particularly includes neurofibrillary tangles (NFT).

"Monomeric Tau" or "Tau monomer" as used herein refers to completely solubilized Tau proteins without aggregated complexes in aqueous medium.

"Aggregated Tau", "oligomeric Tau" and "Tau oligomer" refer to multiple aggregated monomers of Tau peptides or proteins, or of Tau-like peptides/proteins, or of modified or truncated Tau peptides/proteins or of other derivates of Tau peptides/proteins forming oligomeric or polymeric structures which are insoluble or soluble both in vitro in aqueous medium and in vivo in the mammalian or human body more particularly in the brain, but particularly to multiple aggregated monomers of Tau or of modified or truncated Tau peptides/proteins or of derivatives thereof, which are insoluble or soluble in the mammalian or human body more particularly in the brain, respectively.

A "modulating antibody" refers to an antibody or a functional fragment thereof as described herein in the various embodiments, which may either up-regulate (e.g., activate or stimulate), down-regulate (e.g., inhibit or suppress) or otherwise change a functional property, biological activity or level of soluble and/or insoluble Tau protein, particularly of soluble phosphorylated tau protein, in the brain, particularly in the brain cortex and/or hippocampus, of an animal, particularly a mammal or a human containing increased levels of soluble tau protein and/or soluble phosphorylated tau protein. A modulating antibody or functional fragment thereof may act to modulate a tau protein or a polypeptide encoding said tau protein either directly or indirectly. In certain embodiments, a modulating antibody or functional fragment thereof reduces the levels of soluble and insoluble tau protein, particularly of soluble phosphorylated tau protein, in the brain, particularly in the brain cortex and/or hippocampus, of an animal, particularly a mammal or a human containing increased levels of soluble tau protein and/or soluble phosphorylated tau protein."

In one embodiment, the present invention provides a pharmaceutical composition comprising a chimeric antibody or a humanized antibody, or a polynucleotide comprising a nucleic acid sequence encoding said binding peptide or antibody, according to any one of the embodiments described and claimed herein, or a combination thereof, in a therapeutically effective amount together with a pharmaceutically acceptable carrier.

Suitable pharmaceutical carriers, diluents and/or excipients are well known in the art and include, for example, phosphate buffered saline solutions, water, emulsions such as oil/water emulsions, various types of wetting agents, sterile solutions, etc.

As used herein, the terms "treat," "prevent," "preventing," and "prevention" refer to the prevention of the recurrence or onset of one or more symptoms of a disorder in a subject resulting from the administration of a prophylactic or therapeutic agent.

Construction of Humanized Antibodies

The present invention may be understood more readily by reference to the following detailed description of specific embodiments included herein. Although the present invention has been described with reference to specific details of certain embodiments, thereof, it is not intended that such details should be regarded as limitations upon the scope of the invention.

Different HCVR and LCVR regions may be designed which comprise the non-human CDRs obtainable from the donor antibody, for example, a murine antibody, embedded into the native or modified human- or primate-derived framework regions. The modification may particularly concern an exchange of one or more amino acid residues within the framework region by non-human residues, particularly murine residues, more commonly found in this position in the respective subgroups or by residues which have similar properties to the ones more commonly found in this position in the respective subgroups.

The modification of the framework region the framework sequences serve to hold the CDRs in their correct spatial orientation for interaction with antigen, and that framework residues can sometimes even participate in antigen binding. In one embodiment of the invention measures are taken to further adapt the selected human framework sequences to make them most similar to the sequences of the rodent frameworks in order to maximise the likelihood that affinity will be retained in the reshaped antibody.

Accordingly, murine residues in the human framework region may be substituted. In particular, murine residues may be substituted in the human framework region of the Heavy Chain Variable (HCVR) region at positions 47 or 94 or both and in the human framework region of the Light Chain Variable (LCVR) region at positions 45 and/or 87 and/or 50 and/or 53, respectively.

In one embodiment, the present invention provides a pharmaceutical composition comprising a chimeric antibody or a humanized antibody, or a polynucleotide comprising a nucleic acid sequence encoding said binding peptide or antibody, according to any one of the embodiments described and claimed herein, or a combination thereof, in a therapeutically effective amount together with a pharmaceutically acceptable carrier.

Suitable pharmaceutical carriers, diluents and/or excipients are well known in the art and include, for example, phosphate buffered saline solutions, water, emulsions such as oil/water emulsions, various types of wetting agents, sterile solutions, etc.

The chimeric antibody or a humanized antibody according to the invention and active fragments thereof, can be prepared in a physiologically acceptable formulation and may comprise a pharmaceutically acceptable carrier, diluent and/or excipient using known techniques. For example, the antibodies according to the invention and as described herein are combined with a pharmaceutically acceptable carrier, diluent and/or excipient to form a therapeutic composition. Suitable pharmaceutical carriers, diluents and/or excipients are well known in the art and include, for example, phosphate buffered saline solutions, water, emulsions such as oil/water emulsions, various types of wetting agents, sterile solutions, etc. Formulation of the pharmaceutical composition according to the invention can be accomplished according to standard methodology know to those of ordinary skill in the art.

The compositions of the present invention may be administered to a subject in the form of a solid, liquid or aerosol at a suitable, pharmaceutically effective dose. Examples of solid compositions include pills, creams, and implantable dosage units. Pills may be administered orally. Therapeutic creams may be administered topically. Implantable dosage units may be administered locally, for example, at a tumor site, or may be implanted for systematic release of the therapeutic composition, for example, subcutaneously. Examples of liquid compositions include formulations adapted for injection intramuscularly, subcutaneously, intravenously, intra-arterially, and formulations for topical and intraocular administration. Examples of aerosol formulations include inhaler formulations for administration to the lungs.

The compositions may be administered by standard routes of administration. In general, the composition may be administered by topical, oral, rectal, nasal, intradermal, intraperitoneal, or parenteral (for example, intravenous, subcutaneous, or intramuscular) routes.

In addition, the composition may be incorporated into sustained release matrices such as biodegradable polymers, the polymers being implanted in the vicinity of where delivery is desired, for example, at the site of a tumor. The method includes administration of a single dose, administration of repeated doses at predetermined time intervals, and sustained administration for a predetermined period of time.

A sustained release matrix, as used herein, is a matrix made of materials, usually polymers which are degradable by enzymatic or acid/base hydrolysis or by dissolution. Once inserted into the body, the matrix is acted upon by enzymes and body fluids. The sustained release matrix desirably is chosen by biocompatible materials such as liposomes, polylactides (polylactide acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

It is well known to those of ordinary skill in the pertinent art that the dosage of the composition will depend on various factors such as, for example, the condition of being treated, the particular composition used, and other clinical factors such as weight, size, sex and general health condition of the patient, body surface area, the particular compound or composition to be administered, other drugs being administered concurrently, and the route of administration.

The composition according to the invention may be administered in combination with other compositions comprising an biologically active substance or compound such as, for example, a known compound used in the medication of tauopathies and/or of amyloidoses, a group of diseases and disorders associated with amyloid or amyloid-like protein such as the amyloid β protein involved in Alzheimer's Disease.

The other biologically active substance or compound may exert its biological effect by the same or a similar mechanism as the therapeutic vaccine according to the invention or by an unrelated mechanism of action or by a multiplicity of related and/or unrelated mechanisms of action.

Generally, the other biologically active compound may include neutron-transmission enhancers, psychotherapeutic drugs, acetylcholine esterase inhibitors, calcium-channel blockers, biogenic amines, benzodiazepine tranquilizers, acetylcholine synthesis, storage or release enhancers, acetylcholine postsynaptic receptor agonists, monoamine oxidase-A or -B inhibitors, N-methyl-D-aspartate glutamate receptor antagonists, non-steroidal anti-inflammatory drugs, antioxidants, and serotonergic receptor antagonists.

In particular, the biologically active agent or compound may comprise at least one compound selected from the group consisting of compounds against oxidative stress, anti-apoptotic compounds, metal chelators, inhibitors of DNA repair such as pirenzepin and metabolites, 3-amino-1-propanesulfonic acid (3APS), 1,3-propanedisulfonate (1,3PDS), secretase activators, [beta]- and 7-secretase inhibitors, tau proteins, neurotransmitter, /3-sheet breakers, antiinflammatory molecules, "atypical antipsychotics" such as, for example clozapine, ziprasidone, risperidone, aripiprazole or olanzapine or cholinesterase inhibitors (ChEIs) such as tacrine, rivastigmine, donepezil, and/or galantamine and other drugs and nutritive supplements such as, for example, vitamin B 12, cysteine, a precursor of acetylcholine, lecithin, choline, *Ginkgo biloba*, acyetyl-L-carnitine, idebenone, propentofylline, or a xanthine derivative, together with a binding peptide according to the invention including antibodies, particularly monoclonal antibodies and active fragments thereof, and, optionally, a pharmaceutically acceptable carrier and/or a diluent and/or an excipient and instructions for the treatment of diseases.

In a further embodiment, the composition according to the invention may comprise niacin or memantine together with a chimeric antibody or a humanized antibody according to the invention including antibodies, particularly monoclonal antibodies and active fragments thereof, and, optionally, a pharmaceutically acceptable carrier and/or a diluent and/or an excipient.

In still another embodiment of the invention compositions are provided that comprise "atypical antipsychotics" such as, for example clozapine, ziprasidone, risperidone, aripiprazole or olanzapine for the treatment of positive and negative psychotic symptoms including hallucinations, delusions, thought disorders (manifested by marked incoherence, derailment, tangentiality), and bizarre or disorganized behavior, as well as anhedonia, flattened affect, apathy, and social withdrawal, together with the chimeric antibody or the humanized antibody according to the invention or active fragments thereof, and, optionally, a pharmaceutically acceptable carrier and/or a diluent and/or an excipient.

Other compounds that can be suitably used in compositions in addition to chimeric antibody or humanized antibody according to the invention, are those disclosed, for example, in WO 2004/058258 (see especially pages 16 and 17) including therapeutic drug targets (page 36-39), alkanesulfonic acids and alkanolsulfuric acid (pages 39-51), cholinesterase inhibitors (pages 51-56), NMDA receptor antagonists (pages 56-58), estrogens (pages 58-59), non-steroidal anti-inflammatory drugs (pages 60-61), antioxidants (pages 61-62), peroxisome proliferators-activated receptors (PPAR) agonists (pages 63-67), cholesterol-lowering agents (pages 68-75); amyloid inhibitors (pages 75-77), amyloid formation inhibitors (pages 77-78), metal chelators (pages 78-79), anti-psychotics and anti-depressants (pages 80-82), nutritional supplements (pages 83-89) and compounds increasing the availability of biologically active substances in the brain (see pages 89-93) and prodrugs (pages 93 and 94), which document is incorporated herein by reference, but especially the compounds mentioned on the pages indicated above.

Proteinaceous pharmaceutically active matter may be present in amounts between 1 ng and 30 mg per dose. Generally, the regime of administration should be in the range of between 0.1 µg and 10 mg of the antibody according to the invention, particularly in a range 1.0 µg to 1.0 mg, and more particularly in a range of between 1.0 µg and 100 µg, with all individual numbers falling within these ranges also being part of the invention. If the administration occurs through continuous infusion a more proper dosage may be in the range of between 0.01 µg and 10 mg units per kilogram of body weight per hour with all individual numbers falling within these ranges also being part of the invention.

Administration will generally be parentally, e.g. intravenously or subcutaneously. Preparations for parenteral administration include sterile aqueous or non-aqueous solutions, suspensions and emulsions. Non-aqueous solvents include, without being limited to, propylene glycol, polyethylene glycol, vegetable oil such as olive oil, and injectable organic esters such as ethyl oleate. Aqueous solvents may be chosen from the group consisting of water, alcohol/aqueous solutions, emulsions or suspensions including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose) and others. Preservatives may also be present such as, for example, antimicrobials, antioxidants, chelating agents, inert gases, etc.

The pharmaceutical composition may further comprise proteinaceous carriers such as, for example, serum albumin or immunoglobulin, particularly of human origin. Further biologically active agents may be present in the pharmaceutical composition of the invention dependent on its the intended use.

When the binding target is located in the brain, certain embodiments of the invention provide for the chimeric antibody or the humanized antibody according to the invention including active fragments thereof, to traverse the blood-brain barrier. Certain neurodegenerative diseases are associated with an increase in permeability of the blood-brain barrier, such that the binding peptide according to the invention including antibodies or active fragment thereof can be readily introduced to the brain. When the blood-brain barrier remains intact, several art-known approaches exist for transporting molecules across it, including, but not limited to, physical methods, lipid-based methods, and receptor and channel-based methods.

Physical methods of transporting the chimeric antibody or the humanized antibody according to the invention, or active fragment thereof across the blood-brain barrier include, but are not limited to, circumventing the blood-brain barrier entirely, or by creating openings in the blood-brain barrier. Circumvention methods include, but are not limited to, direct injection into the brain (see, e.g., Papanastassiou et al., Gene Therapy 9: 398-406 (2002)) and implanting a delivery device in the brain (see, e.g., Gill et al., Nature Med. 9: 589-595 (2003); and Gliadel Wafers™, Guildford Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Vols 1 & 2, Plenum Press, N. Y. (1989)), permeabilization by, e.g., bradykinin or permeabilizer A-7 (see, e.g., U.S. Pat. Nos. 5,112,596, 5,268,164, 5,506,206, and 5,686, 416), and transfection of neurons that straddle the blood-brain barrier with vectors containing genes encoding the binding peptide or antigen-binding fragment (see, e.g., U.S. Patent Publication No. 2003/0083299).

Lipid-based methods of transporting the chimeric antibody or the humanized antibody according to the invention including antibodies, particularly monoclonal antibodies, or an active fragment thereof across the blood-brain barrier include, but are not limited to, encapsulating the chimeric antibody or the humanized antibody according to the invention, or active fragment thereof in liposomes that are coupled to active fragments thereof that bind to receptors on the vascular endothelium of the blood-brain barrier (see, e.g., U.S. Patent Application Publication No. 20020025313), and coating the binding peptide according to the invention including antibodies, particularly monoclonal antibodies, or active fragment thereof in low-density lipoprotein particles (see, e.g., U.S. Patent Application Publication No. 20040204354) or apolipoprotein E (see, e.g., U.S. Patent Application Publication No. 20040131692).

Receptor and channel-based methods of transporting the chimeric antibody or the humanized antibody according to the invention, or active fragment thereof across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating antibodies with a transferrin and modulating activity of the one or more transferrin receptors (see, e.g., U.S. Patent Application Publication No. 2003/0129186), and cationizing the antibodies (see, e.g., U.S. Pat. No. 5,004,697).

Additionally, antibodies of the present invention may be engineered to take advantage of receptor mediated transport (RMT) across the blood brain barrier (BBB) by various exploiting BBB receptors (ie, transferrin receptor, insulin receptor, low density lipoprotein receptor-related protein 8, glucose transporter 1 (Glut1) and the like) (see, e.g., WO9502421). For example, the antibodies of the present invention can be made multispecific to target tau and the BBB receptor. A non-limiting example of a multispecific antibody includes a bispecific antibody in which one arm of the antibody is an antibody fragment of the present invention and the other arm of the antibody targets a BBB receptor which mediates transport across the BBB. The BBB receptor for example can include transferrin receptor (TfR), insulin receptor, insulin-like growth factor receptor (IGF receptor), low density lipoprotein receptor-related protein 8 (LRP8), low density lipoprotein receptor-related protein 1 (LRP1), glucose transporter 1 (Glut1) and heparin-binding epidermal growth factor-like growth factor (HB-EGF).

Single or repeated administrations of the chimeric antibody or the humanized antibody according to the invention, or an active fragment thereof, or of a pharmaceutical composition according to the invention may be provided to a subject over an extended period of time. The duration of administration may be between 1 week and up to 12 month or more. During this time the binding peptide, antibody or pharmaceutical composition may be administered once a week, once every two weeks, three weeks, four weeks, etc, or at a higher or lower frequency depending on the needs of the subject to be treated.

In a further embodiment the present invention provides methods and kits for the detection and diagnosis of tau-protein-associated diseases, disorders or conditions, including neurodegenerative diseases or disorders such as tauopathies comprising a heterogeneous group of neurodegenerative diseases or disorders including diseases or disorders which show co-existence of tau and amyloid pathologies including, but not limited to, Alzheimer's Disease, Creutzfeldt-Jacob disease, Dementia pugilistica, Down's Syndrome, Gerstmann-Sträussler-Scheinker disease, inclusion-body myositis, and prion protein cerebral amyloid angiopathy, traumatic brain injury and further of diseases or disorders which do not show a distinct amyloid pathology including, but not limited to, amyotrophic lateral sclerosis/parkinsonism-dementia complex of Guam, Non-Guamanian motor neuron disease with neurofibrillary tangles, argyrophilic grain dementia, corticobasal degeneration, diffuse neurofibrillary tangles with calcification, frontotemporal dementia with parkinsonism linked to chromosome 17, Hallevorden-Spatz disease, multiple system atrophy, Niemann-Pick disease, type C, Pallido-ponto-nigral degeneration, Pick's disease, progressive subcortical gliosis, progressive supranuclear palsy, Subacute sclerosing panencephalitis Tangle only dementia, Postencephalitic Parkinsonism, Myotonic dystrophy. The pathological abnormalities may be caused by or associated with the formation of neurofibrillary lesions, the predominant brain pathology in tauopathy.

Further, the present invention provides methods and kits for diagnosing a predisposition to tau-protein-associated diseases, disorders or conditions, including neurodegenerative diseases or disorders such as tauopathies comprising a heterogeneous group of neurodegenerative diseases or disorders including diseases or disorders which show co-existence of tau and amyloid pathologies, or for monitoring minimal residual disease in a patient or for predicting responsiveness of a patient to a treatment with chimeric antibody or the humanized antibody according to the invention, or a composition according to the invention and as described herein. These methods include known immunological methods commonly used for detecting or quantifying substances in biological samples or in an in situ condition.

Diagnosis of a tau-protein-associated disease or condition or of a predisposition to an tau-protein-associated disease or condition in a subject in need thereof, particularly a mammal, more particularly a human, including neurodegenerative diseases or disorders such as tauopathies comprising a heterogeneous group of neurodegenerative diseases or disorders including diseases or disorders which show co-existence of tau and amyloid pathologies, may be achieved by detecting the immunospecific binding of a binding peptide of the invention, particularly of an antibody, particularly of a monoclonal antibody or an active fragment thereof, to an epitope of the tau protein in a sample or in situ, which includes bringing the sample or a specific body part or body area suspected to contain the tau protein into contact with an antibody which binds an epitope of the tau protein, allowing the antibody to bind to the tau protein to form an immunologic complex, detecting the formation of the immunologic complex and correlating the presence or absence of the immunologic complex with the presence or absence of tau protein in the sample or specific body part or area, optionally comparing the amount of the immunologic complex to a normal control value, wherein an increase in the amount of the immunologic complex compared to a normal control value indicates that the subject is suffering from or is at risk of developing an tau protein-associated disease or condition.

Monitoring minimal residual disease in a subject, particularly a mammal, more particularly a human, following treatment with a binding peptide according to the invention including antibodies, particularly monoclonal antibodies and active fragments thereof, or a composition according to the invention may be achieved by detecting the immunospecific binding of a binding peptide of the invention, particularly of an antibody, particularly a monoclonal antibody or an active fragment thereof to an epitope of the tau protein in a sample or in situ, which includes bringing the sample or a specific body part or body area suspected to contain the tau protein into contact with a binding peptide according to the invention including antibodies, particularly monoclonal antibodies and active fragments thereof, which binds an epitope of the tau protein, allowing the binding peptide according to the invention including antibodies, particularly monoclonal antibodies and active fragments thereof, to bind to the tau protein to form an immunologic complex, detecting the formation of the immunologic complex and correlating the presence or absence of the immunologic complex with the presence or absence of tau protein in the sample or specific body part or area, optionally comparing the amount of said immunologic complex to a normal control value, wherein an increase in the amount of said immunologic complex compared to a normal control value indicates that the subject may still suffer from a minimal residual disease.

Predicting responsiveness of a subject, particularly a mammal, more particularly a human, to a treatment with chimeric antibody or the humanized antibody according to the invention, or a composition according to the invention may be achieved by detecting the immunospecific binding of a binding peptide, particularly of a monoclonal antibody or an active fragment thereof to an epitope of the tau protein in a sample or in situ, which includes bringing the sample or a specific body part or body area suspected to contain the tau protein into contact with a binding peptide according to the invention including antibodies, particularly monoclonal antibodies and active fragments thereof, which binds an epitope of the tau protein, allowing the chimeric antibody or the humanized antibody according to the invention or active fragments thereof, to bind to the tau protein to form an immunologic complex, detecting the formation of the immunologic complex and correlating the presence or absence of the immunologic complex with the presence or absence of tau protein in the sample or specific body part or area, optionally comparing the amount of said immunologic complex before and after onset of the treatment, wherein an decrease in the amount of said immunologic complex indicates that said patient has a high potential of being responsive to the treatment.

Biological samples that may be used in the diagnosis of a tau protein-associated disease or condition, for diagnosing a predisposition to a tau protein-associated disease or condition, including neurodegenerative diseases or disorders such as tauopathies comprising a heterogeneous group of neurodegenerative diseases or disorders including diseases or disorders which show co-existence of tau and amyloid pathologies, or for monitoring minimal residual disease in a patient or for predicting responsiveness of a patient to a treatment with chimeric antibody or the humanized antibody according to the invention or active fragments thereof, or a composition according to the invention and as described herein are, for example, fluids such as serum, plasma, saliva, gastric secretions, mucus, cerebrospinal fluid, lymphatic fluid and the like or tissue or cell samples obtained from an organism such as neural, brain, cardiac or vascular tissue. For determining the presence or absence of the tau protein in a sample, any immunoassay known to those of ordinary skill in the art may be used such as, for example, assays which utilize indirect detection methods using secondary reagents for detection, ELISA's and immunoprecipitation and agglutination assays. A detailed description of these assays is, for example, given in Harlow and Lane, Antibodies: A Laboratory Manual (Cold Spring Harbor Laboratory, New York 1988 555-612, WO96/13590 to Maertens and Stuyver, Zrein et al. (1998) and WO96/29605.

For in situ diagnosis, the chimeric antibody or the humanized antibody according to the invention including antibodies, or active fragments thereof, may be administered to the organism to be diagnosed by methods known in the art such as, for example, intravenous, subcutaneous, intranasal, intraperitoneal, intracerebral, intra-arterial injection such that a specific binding between an antibody according to the invention with an epitopic region on the amyloid protein may occur. The binding peptide/antigen complex may conveniently be detected through a label attached to the chimeric antibody or the humanized antibody according to the invention, or a functional fragment thereof or any other art-known method of detection.

The immunoassays used in diagnostic applications or in applications for diagnosing a predisposition to a tau protein-associated disease or condition, including neurodegenerative diseases or disorders such as tauopathies comprising a heterogeneous group of neurodegenerative diseases or disorders including diseases or disorders which show co-existence of tau and amyloid pathologies, or for monitoring minimal residual disease in a patient or for predicting responsiveness of a patient to a treatment with the chimeric antibody or the humanized antibody according to the invention including antibodies, or active fragments thereof, or a composition according to the invention and as described herein typically rely on labelled antigens, binding peptides, or secondary reagents for detection. These proteins or reagents can be labelled with compounds generally known to those of ordinary skill in the art including enzymes, radioisotopes, and fluorescent, luminescent and chromogenic substances including, but not limited to coloured particles, such as colloidal gold and latex beads. Of these, radioactive labelling can be used for almost all types of assays and with most variations. Enzyme-conjugated labels are particularly useful when radioactivity must be avoided or when quick results are needed. Fluorochromes, although requiring expensive equipment for their use, provide a very sensitive method of detection. Binding peptides useful in these assays are those disclosed claimed herein including antibodies, particularly monoclonal antibodies, polyclonal antibodies, and affinity purified polyclonal antibodies.

Alternatively, the chimeric antibody or the humanized antibody according to the invention, or active fragments thereof, may be labelled indirectly by reaction with labelled substances that have an affinity for immunoglobulin, such as protein A or G or second antibodies. The chimeric antibody or the humanized antibody according to the invention, or active fragments thereof, may be conjugated with a second substance and detected with a labelled third substance having an affinity for the second substance conjugated to the antibody. For example, the chimeric antibody or the humanized antibody according to the invention, or active fragments thereof, may be conjugated to biotin and the binding peptide/biotin conjugate detected using labelled avidin or streptavidin. Similarly, the binding peptide may be conjugated to a hapten and the binding peptide/hapten conjugate detected using labelled anti-hapten binding peptide.

Those of ordinary skill in the art will know of these and other suitable labels which may be employed in accordance with the present invention. The binding of these labels to binding peptides or fragments thereof can be accomplished using standard techniques commonly known to those of ordinary skill in the art. Typical techniques are described by Kennedy, J. H., et al., 1976 (Clin. Chim. Acta 70:1-31), and Schurs, A. H. W. M., et al. 1977 (Clin. Chim Acta 57:1-40).

Coupling techniques mentioned in the latter are the glutaraldehyde method, the periodate method, the dimaleimide method, and others, all of which are incorporated by reference herein.

Current immunoassays utilize a double antibody method for detecting the presence of an analyte, wherein, the antibody is labeled indirectly by reactivity with a second antibody that has been labeled with a detectable label. The second antibody is preferably one that binds to antibodies of the animal from which the monoclonal antibody is derived. In other words, if the monoclonal antibody is a mouse antibody, then the labeled, second antibody is an anti-mouse antibody. For the antibody to be used in the assay described herein, this label is preferably an antibody-coated bead, particularly a magnetic bead. For the antibody to be employed in the immunoassay described herein, the label is preferably a detectable molecule such as a radioactive, fluorescent or an electrochemiluminescent substance.

An alternative double antibody system, often referred to as fast format systems because they are adapted to rapid determinations of the presence of an analyte, may also be employed within the scope of the present invention. The system requires high affinity between the antibody and the analyte. According to one embodiment of the present invention, the presence of the tau protein is determined using a pair of antibodies, each specific for amyloid protein. One of said pairs of antibodies is referred to herein as a "detector antibody" and the other of said pair of antibodies is referred to herein as a "capture antibody". The monoclonal antibody of the present invention can be used as either a capture antibody or a detector antibody. The monoclonal antibody of the present invention can also be used as both capture and detector antibody, together in a single assay. One embodiment of the present invention thus uses the double antibody sandwich method for detecting tau protein in a sample of biological fluid. In this method, the analyte (tau protein) is sandwiched between the detector antibody and the capture antibody, the capture antibody being irreversibly immobilized onto a solid support. The detector antibody would contain a detectable label, in order to identify the presence of the antibody-analyte sandwich and thus the presence of the analyte.

Exemplary solid phase substances include, but are not limited to, microtiter plates, test tubes of polystyrene, magnetic, plastic or glass beads and slides which are well known in the field of radioimmunoassay and enzyme immunoassay. Methods for coupling antibodies to solid phases are also well known to those of ordinary skill in the art. More recently, a number of porous material such as nylon, nitrocellulose, cellulose acetate, glass fibers and other porous polymers have been employed as solid supports.

The present invention also relates to a diagnostic kit for detecting tau protein in a biological sample comprising a composition as defined above. Moreover, the present invention relates to the latter diagnostic kit which, in addition to a composition as defined above, also comprises a detection reagent as defined above. The term "diagnostic kit" refers in general to any diagnostic kit known in the art. More specifically, the latter term refers to a diagnostic kit as described in Zrein et al. (1998).

It is still another object of the present invention to provide novel immunoprobes and test kits for detection and diagnosis of tau protein-associated diseases and conditions, comprising binding peptides according to the present invention. For immunoprobes, the binding peptides are directly or indirectly attached to a suitable reporter molecule, e.g., an enzyme or a radionuclide. The test kit includes a container holding one or more binding peptides according to the present invention and instructions for using the binding peptides for the purpose of binding to tau antigen to form an immunologic complex and detecting the formation of the immunologic complex such that presence or absence of the immunologic complex correlates with presence or absence of tau protein.

EXAMPLES

Example 1

Binding of hACl-36-2B6-Ab1 and hACl-36-3A8-Ab1 to T4 Peptides by ELISA 1.1. Method
1.1.1 Phospho-Tau Binding Assay To test the binding of the antibody to pTau, an ELISA assay was used. Nunc MaxiSorp 96-well plates (Nunc, Denmark) were coated with 10 µg/mL of the Tau-derived peptide Tau401-418, phosphorylated (T4.5) or not (T4.6) on serine 409. Coating was done overnight in phosphate-buffered saline (PBS; Sigma-Aldrich, Switzerland) at 4° C. Plates were washed thoroughly with 0.05% Tween20/PBS and then blocked with 1% bovine serum albumin (BSA; Sigma-Aldrich) in 0.05% Tween20/PBS for 1 hr at 37° C. The supernatant containing the antibody being tested was then added in 8 two-fold dilutions, starting at 0.5 µg/mL, and incubated for 2 hr at 37° C. Plates were then washed as described previously, and an alkaline phosphatase (AP) conjugated goat anti-human IgG (Jackson ImmunoResearch Laboratories, England) was added at 1/2,000 dilution in 0.05% Tween20/PBS for 2 hr at 37° C. After washing, plates were incubated with p-nitrophenyl phosphate disodium hexahydrate (pNPP; Sigma-Aldrich, Switzerland) phosphatase substrate solution, and read at 405 nm following 1 hr incubation using a microplate reader (Tecan, Switzerland). Results are expressed as optical density (O.D.).

1.2. Results

Binding of the humanized antibodies hACl-36-2B6-Ab1 and hACl-36-3A8-Ab1 to the pTau target was tested using direct ELISAs on the T4.5 and T4.6 peptides. Both antibodies demonstrated high binding to the target (FIG. 1). No binding was observed to the corresponding non-phosphorylated Tau peptide (T4.6). This demonstrates high binding of antibodies hACl-36-2B6-Ab1 and hACl-36-3A8-Ab1 to the target.

Example 2

Staining of pTau in Brains of 20 Month Old Transgenic Tauopathy (biGT) Mice by TAUPIR Using hACl-36-2B6-Ab1 and hACl-36-3A8-Ab1

2.1. Method
2.1.1 Binding of Anti-Tau Antibody to Tau Tangles on Brain Sections from a Tau Transgenic Animal (TAUPIR)

Brain slices used were from old (>18 months old) double transgenic biGT (GSK-3β transgenic mice crossed with TPLH mice, containing the longest isoform (441aa) of human Tau with the P301 L mutation) tauopathy mice. Brain sections were washed for 5 min in PBS then incubated for 15 min at ambient temperature in 1.5% $H_2O_2$ in PBS:MeOH (1:1) to block endogenous peroxidase activity. After washing the sections 3 times in PBST (PBS/0.1% TritonX100) they were incubated for 30 min at RT in PBST+10% FCS (fetal calf serum) blocking solution. Sections were then incubated with the undiluted supernatant containing the antibody being tested overnight at 4° C. Sections were next washed 3 times in PBST before incubation with an HRP-conjugated anti-human IgG4 (Invitrogen) secondary antibody in PBST/10% FCS for 1 hour at RT. Prior to detection, sections were washed 3 times with PBST and incubated in 50 mM Tris/HCl pH7.6 for 5 min. Detection was done by incubating the sections for 3 min in Diaminobenzidine (DAB: 1 tablet in 10 ml of 50 mM Tris.HCl+3 µl H2O2 30%; MP Biomedicals, USA). The reaction was stopped by washing the sections 3 times in PBST. Sections were then transferred onto silanized glass-plates and air-dried on warm-plate at 50° C. for 2 hours. Counterstaining was done using incubation with Mayers hematoxylin (Fluka Chemie, Switzerland) for 1 min, followed by a washing step for 4 min in running tap-water. Sections were dehydrated by passing in 50%, 70%, 90% and twice in 100% ethanol bath then in Xylol 2 times for 1 min. Finally, mounting was done with DePeX (BDH Chemicals Ltd., England) under glass coverslips.

2.2. Results

Figure 2:
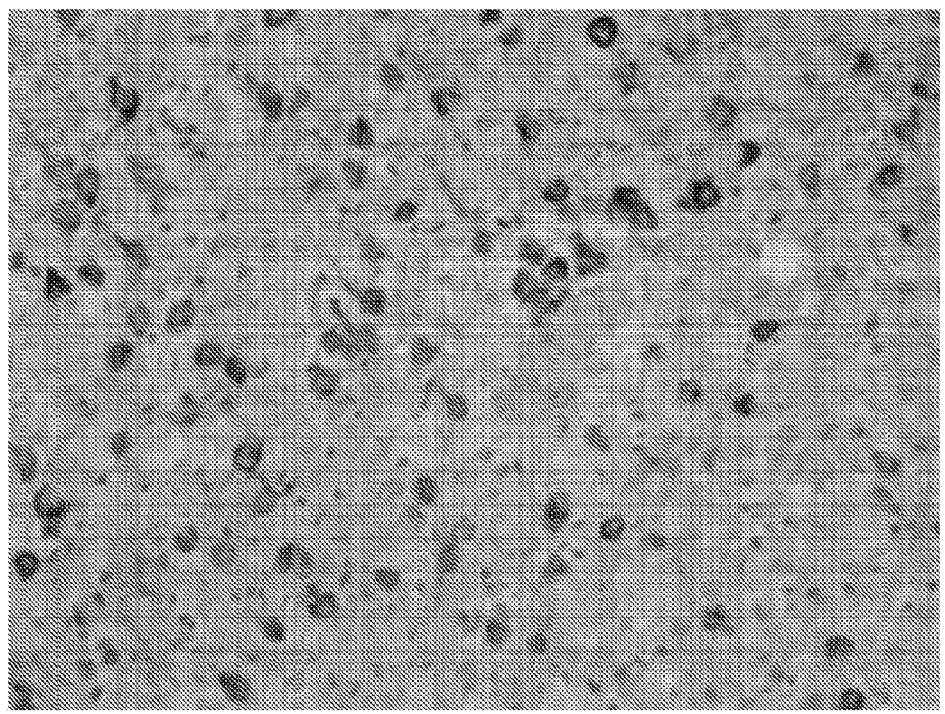
FIG. 2 shows Tau tangles in the brain of 20 month old Tau transgenic (biGT) mice stained with humanized anti-pTau antibody hACl-36-2B6-Ab1. Staining is shown for Tau tangles in cortex (A) and hippocampus (B), with staining of neuropil threads visible in the hippocampus (B).
Figure 2:
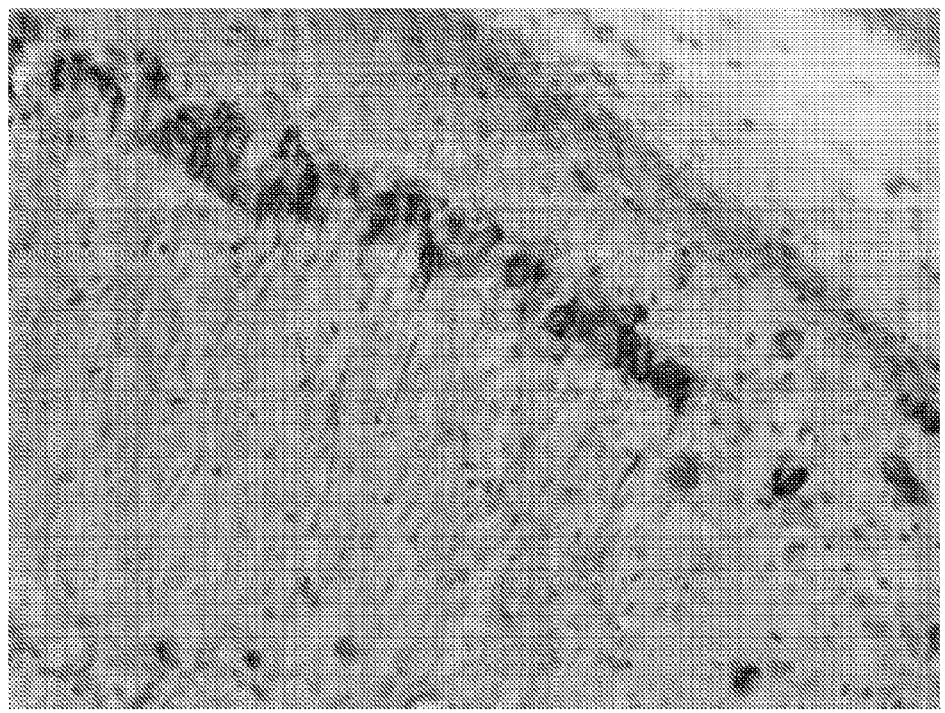
Figure 3:
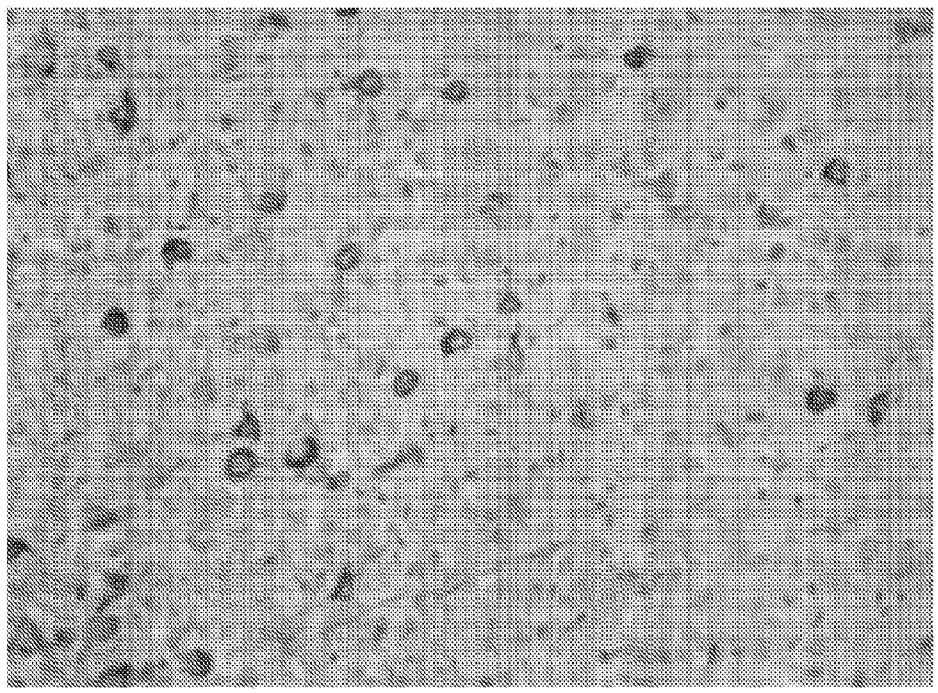
FIG. 3 shows Tau tangles in the brain of 20 month old Tau transgenic (biGT) mice stained with humanized anti-pTau antibody hACl-36-3A8-Ab1 stains. Staining is shown for Tau tangles in cortex (A) and hippocampus (B), with staining of neuropil threads visible in the hippocampus (B).
Figure 3:
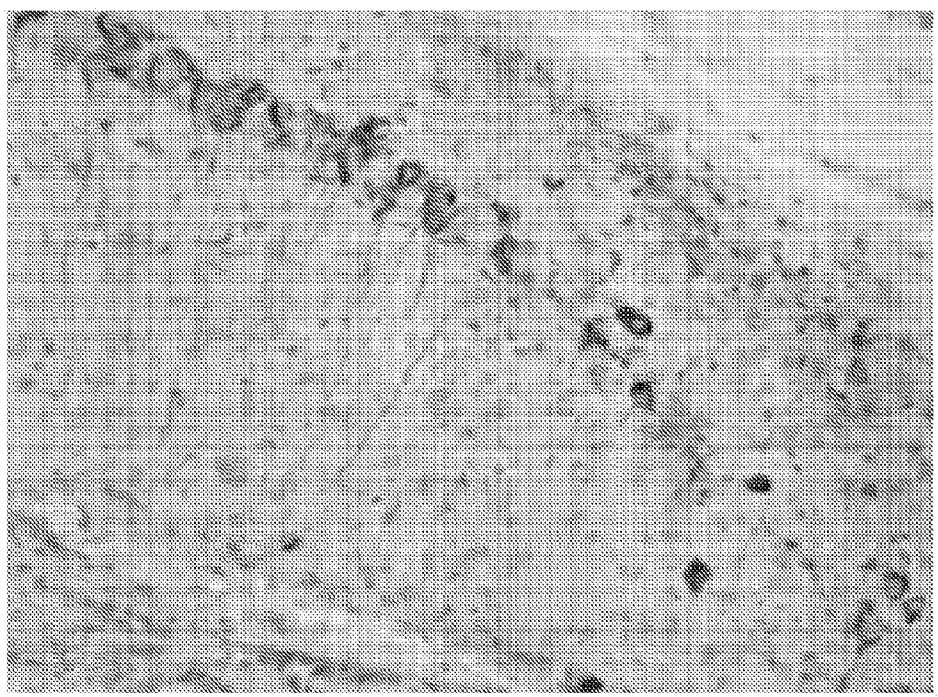

The binding of humanized antibodies hACI-36-2B6-Ab1 and hACI-36-3A8-Ab1 pTau in brains of transgenic tauopathy (biGT) mice was evaluated by TAUPIR staining. Antibodies hACI-36-2B6-Ab1 (FIGS. 2A and 2B) and hACI-36-3A8-Ab1 (FIGS. 3A and 3B) demonstrated binding to Tau tangles and neuropil threads present in the brains of tauopathy mice.

Example 3

Binding Studies II: Antibody Affinity by Biacore/SPR 3.1 Methods
3.1.1 SPR Binding Assay In order to evaluate the binding interaction between hACI-36-2B6-Ab1 and the peptide T4.5, the antibody hACI-36-2B6-Ab1 was immobilized upon a sensor chip, and then T4.5 was injected as analyte.

SPR experiments were carried out on a Biacore T100 instrument (GE Healthcare). Reagents for immobilization (EDC, NHS and Ethanolamine) and sensor chip CM7 (carboxymethyl dextran) were purchased from GE Healthcare. Running buffer was PBS (Dulbecco's PBS, Sigma). In order to correctly orientate the antibody for binding to peptide T4.5, the antibody was coupled to the sensor surface via Protein G. For this, recombinant Protein G (Sigma) was diluted from a stock solution in water (2 mg/mL) with 10 mM sodium acetate pH 4.0 (GE Healthcare) to 50 µg/mL. This protein solution was then coupled to flow cell (fc) 2 of a CM7 sensor chip that was preactivated using EDC/NHS. After coupling, Ethanolamine was passed over the surface and giving a final immobilization level of 9860 RUs on fc1 and 9492 RUs on fc2. hACI-36-2B6-Ab1 was then diluted to 100 µg/mL with 10 mM phosphate buffer pH 7.4 and injected at 2 µL/min for 85 s to give an immobilization level of 8340 RUs. In order to ensure a flat baseline was obtained prior injection of peptide T4.5, PBS was run over the sensor surface for approximately 2 h and then the system was twice primed with PBS. Five concentrations of peptide T4.5 (50→800 nM) were assayed by 2-fold serial dilutions using running buffer. Injections were performed starting from the lowest concentration and were passed over both fc 1 and 2 at a flow rate of 50 µL/min using the single-cycle kinetics method. Association and dissociation times were both performed for 90 s for each concentration of peptide. Responses from fc 1 were subtracted from fc 2 to correct for instrument noise, bulk refractive changes and non-specific binding to the carboxymethyl dextran surface. Kinetic analysis was performed using algorithms for numerical integration and global analysis using Biacore T100 Evaluation software. For curve fitting, all data were fit simultaneously to a 1:1 homogeneous (Langmuir) model.

Peptide Used

| | | |
|---|---|---|
| T 4.5 | H—K(Ac)K(Ac)—GDTS[PO3H2]PRHLS [PO3H2]NVSSTGSID—K(Ac)K(Ac)—NH2 | lot CF09166 |

3.2 Results

The binding of the tau peptide to the humanized antibody hACI-36-2B6-Ab1 was monitored in real-time using SPR. Analyses of the association and dissociation phases of antibody binding could be used to determine the association rate constant ($k_a$), dissociation rate constant ($k_d$) as well as dissociation constant $K_D$. Kinetic analyses for the binding of peptide T4.5 to immobilized antibody hACI-36-2B6-Ab1 was performed which revealed a fast association rate constant of $0.54 \times 10^5$ $M^{-1}s^{-1}$ and a dissociation rate constant of $36.0 \times 10^{-4}$ $s^{-1}$ (Table below).

| Ligand | Analyte | Association rate constant ($k_a$) (1/Ms) | Dissociation rate constant ($k_d$ (1/s)) | Dissociation constant ($K_D$) (nM) |
|---|---|---|---|---|
| hACI-36-2B6-Ab1 | T 4.5 | $0.54 \times 10^5$ | $36.0 \times 10^{-4}$ | 67 |

Example 4

Epitope Mapping 4.1 Methods
4.1.1 Epitope Mapping Assay

Epitope mapping of anti-phospho Tau humanized monoclonal antibodies was performed by ELISA using different phospho and non-phospho peptide libraries. The amino acid sequences of peptide libraries scanning the expected epitope are shown in Table 5A. Additionally, a peptide library was generated substituting each residue of a peptide sequence that binds to the antibody with Alanine (Ala), as shown in Table 5B. Each library consisted of short biotinylated peptides spanning phospho and non-phospho sequences present in the peptide vaccine. Peptide libraries were purchased from ANAWA Trading SA. Epitope mapping was done according to the manufacturer's (Mimotopes) instructions. Briefly, streptavidin coated plates (NUNC) were blocked with 0.1% BSA in phosphate-buffered saline (PBS) overnight at 4° C. After washing with PBS-0.05% Tween 20, plates were coated for 1 hr at RT with the different peptides from each library, diluted in 0.1% BSA, 0.1% sodium azide in PBS to a final concentration of 10 µM. After washing, plates were incubated for 1 hr at RT with the antibody to be tested at different dilutions in 2% BSA, and 0.1% sodium azide in PBS. Plates were washed again and incubated with AP-conjugated goat anti-human IgG (Jackson Cat. 109-055-098, Lot 95531) at 1/2000 dilution for 30 min to 1 hr at RT. After a final wash, plates were incubated with p-nitrophenyl phosphate disodium hexahydrate (pNPP; Sigma-Aldrich, Buchs, Switzerland) phosphatase substrate solution, and read at 405 nm following 2 hr incubation using an ELISA plate reader. Binding was considered positive if the optical density (O.D.) was at least 2-times over background O.D.

4.2 Results

The epitope of hAC1-36-2B6-Ab1 was determined using ELISAs for binding to the peptides shown in Table 5A and 5B. The epitope of antibody hAC1-36-2B6-Ab1 was mapped to a region comprising amino acid residues 404-411 of the longest isoform of human Tau (TAU441), with S409 phosphorylated (pS409), and preferential binding to Tau amino acid residues, H407, pS409, N410, and V411.

Deposits

The following plasmids in bacteria (transformed *E. coli*) were deposited in the name of AC Immune SA, PSE-EPFL Building B, 1015 Lausanne, Switzerland, with the "Deutsche Sammlung von Mikroorganismen and Zellkulturen GmbH (DSMZ) in Braunschweig, Inhoffenstrasse 7 B, 38124 Braunschweig, under the provisions of the Budapest Treaty:

| Strain name | Deposit number | Date of deposit |
|---|---|---|
| Escherichia coli 2B6A10C11-H | DSM 25743 | Mar. 6, 2012 |
| Escherichia coli 2B6A10C11-L | DSM 25744 | Mar. 6, 2012 |
| Escherichia coli 3A8A12G7-H | DSM 25745 | Mar. 6, 2012 |
| Escherichia coil 3A8A12G7-L | DSM 25746 | Mar. 6, 2012 |

TABLE 1

Amino Acid Sequence of the heavy chain and light chain variable regions (HCVR and LCVR) and the CDRs

| Antibody name | Hybridoma | HCVR | LCVR | HCVR CDR1 | HCVR CDR2 | HCVR CDR3 | LCVR CDR1 | LCVR CDR2 | LCVR CDR3 |
|---|---|---|---|---|---|---|---|---|---|
| hAC1-36-3A8-Ab1 | 3A8A12G7 | QVQLVQSGAEVKKPGSSVKVSCKASGYTFTDYYMNVVVRQAPGQGLEWIGDINPNRGGTTYNQKFKGRVTITVDKSTSTAYMELSSLRSEDTAVYYCASYYAVGYWGQGTTVTVSS (SEQ ID NO: 7) | DIVMTQTPLSLPVTPGEPASISCRSSQRLVHSHGKTYLHWYLQKPGQSPQLLIYKVSNRFSGVPDRFSGSGSGTDFTLKISRVEAEDVGVYFCSQTAHFPYTFGGGTKVEIK (SEQ ID NO: 8) | GYTFTDYYMN (SEQ ID NO: 1) | DINPNRGGTTYNQKFKG (SEQ ID NO: 2) | YYAVGY (SEQ ID NO: 3) | RSSQRLVHSHGKTYLH (SEQ ID NO: 4) | KVSNRFS (SEQ ID NO: 5) | SQTAHFPYT (SEQ ID NO: 6) |
| hAC1-36-2B6-Ab1 | 2B6A10C11 | QVQLVQSGAEVKKPGSSVKVSCKASGYTFTDYYMNWVRQAPGQGLEWIGDINPNRGGTTYNQKFKGRVTITVDKSTSTAYMELSSLRSEDTAVYYCASYYAVGYWGQGTTVTVSS (SEQ ID NO: 7) | DIVMTQTPLSLPVTPGEPASISCRSSQSLVHSHGKTYLHWYLQKPGQSPQLLIYKVSNRFSGVPDRFSGSGSGTDFTLKISRVEAEDVGVYFCSQTAHFPYTFGGGTKVEIK (SEQ ID NO: 9) | GYTFTDYYMN (SEQ ID NO: 1) | DINPNRGGTTYNQKFKG (SEQ ID NO: 2) | YYAVGY (SEQ ID NO: 3) | RSSQSLVHSHGKTYLH (SEQ ID NO: 10) | KVSNRFS (SEQ ID NO: 5) | SQTAHFPYT (SEQ ID NO: 6) |

TABLE 2

Nucleotide Sequence of the heavy chain and light chain (H and L)

| antibody name | Hybridoma | Heavy chain (H) | Light chain (L) |
|---|---|---|---|
| hAC1-36-3A8-Ab1 | 3A8A12G7 | AAGCTTGCCGCCACCATGGGATGGAGCTGTATCATCCTCTTCTTGGTAGCAACAGCTACAGGTAAGGGGCTCACAGTAGCAGGCTTGAGGTCTGGACATATATATGGGTGACAATGACATCCACTTTGCCTTTCTCTCCACAGGTGTCCACTCCCAGGTCCAGCTGGTGCAATCTGGAGCCGAAGTGAAGAAGCCTGGGTCCTGCGGAAGGTGTCCTGTAAGGCTTCTGGATATACCTTCACTGACTACTACATGAACTGGGTGAGGCAGGCCCCTGGACAGGGCCTTGAGTGGATTGGAGATATTAATCCTAACCGCGGTGGAACTACTTACAACCAGAAGTTCAAGGGCAGGGTGACCATCACTGTGGACAAGTCCACCAGCACAGCCTACATGGAACTCAGCAGCCTGAGATCTGAGGACACCGCAGTCTATTACTGTGCAAGTTACTACGCCGTGGGCTACTGGGGCCAAGGCACCACTGTGACAGTCTCCTCAGGTGAGTCCTTACAACCTCTCTCTTCTATTCAGCTTAAATAGATTTTACTGCATTTGTTGGGGGGGAAATGTGTGTATCTGAATTTCAGGTCATGAAGGACTAGGACACCTTGGGAGTCAGAAAGGGTCATTGGGAGCCCGGGCTGATGCAGACAGACATCCTCAGCTCCCAGACTTCATGGC | AAGCTTGCCGCCACCATGGGATGGAGCTGTATCATCCTCTTCTTGGTAGCAACAGCTACAGGTAAGGGGCTCACAGTAGCAGGCTTGAGGTCTGGACATATATATGGGTGACAATGACATCCACTTTGCCTTTCTCTCCAGGTGTCCACTCCGATATCGTGATGACCCAAACTCCACTCTCCCTGCCTGTCACCCCTGGAGAGCCCGCCTCCATCTCTTGCAGATCTAGTCAGAGGCTTGTGCACAGTCATGGAAAAACCTATCTGCATTGGTACCTGCAGAAGCCAGGCCAGTCTCCACAGCTCCTGATCTACAAAGTTTCCAACCGGTTTTCTGGGGTCCCAGACAGGTTCAGTGGCAGTGGATCAGGGACAGATTTCACACTCAAGATCAGCAGAGTGGAGGCTGAGGATGTGGGAGTTTATTTCTGTTCTCAAACTGCACATTTTCCCTACACCTTCGGAGGGGGGACCAAGGTGGAAATCAAACGTGAGTAGAATTTAAACTTTGCTTCCTCAGTTGGATCCACTAGTCCAGTGTGGTGGAATTCTAAACTCTGAGGGGTCGGATGACCTGGCCATTCTTGCCTAAAGCATTGAGTTTACTGCGCTAGGAAGAAACTCAAAACATCAAGATTTTAAATACGCTTCTTG |

TABLE 2-continued

Nucleotide Sequence of the heavy chain and light chain (H and L)

| anti-<br>body<br>name | Hy-<br>brid-<br>oma | Heavy chain (H) | Light chain (L) |
|---|---|---|---|
| | | CAGAGATTATAGGATCCAGCTTTCTGGGGCAGGCCAGGC<br>CTGACCTTGGCTGGGGGCAGGGAGGGGGCTAAGGTGACG<br>CAGGTGGCGCCAGCCAGGTGCACACCCAATGCCCATGAG<br>CCCAGACACTGGACCCTGCATGGACCATCGCGGATAGACA<br>AGAACCGAGGGGCCTCTGCGCCCTGGGCCCAGCTCTGTC<br>CCACACCGCGGTCACATGGCACCACCTCTCTTGCAGCTTC<br>CACCAAGGGCCCATCCGTCTTCCCCCTGGCGCCCTGCTCC<br>AGATCGACCTCCGAGAGCACAGCCGCCCTGGGCTGCCTG<br>GTCAAGGACTACTTCCCCGAACCGGTGACGGTGTCGTGGA<br>ACTCAGGCGCCCTGACCAGCGGCGTGCACACCTTCCCGG<br>CTGTCCTACAGTCCTCAGGACTCTACTCCCTCAGCAGCGT<br>GGTGACCGTGCCCTCCAGCAGCTTGGGCACGAAGACCTA<br>CACCTGCAACGTAGATCACAAGCCCAGCAACACCAAGGTG<br>GACAAGAGAGTTGGTGAGAGGCCAGCACAGGGAGGGAGG<br>GTGTCTGCTGGAAGCCAGGCTCAGCCCTCCTGCCTGGAC<br>GCACCCCGGCTGTGCAGCCCCAGCCCAGGGCAGCAAGGC<br>ATGCCCCATCTGTCTCCTCACCCGGAGGCCTCTGACCACC<br>CCACTCATGCTCAGGGAGAGGGTCTTCTGGATTTTTCCAC<br>CAGGCTCCGGGCAGCCACAGGCTGGATGCCCCTACCCCA<br>GGCCCTGCGCATACAGGGGCAGGTGCTGCGCTCAGACCT<br>GCCAAGAGCCATATCCGGGAGGACCCTGCCCCTGACCTAA<br>GCCCACCCCAAAGGCCAAACTCTCCACTCCCTCAGCTCAG<br>ACACCTTCTCTCCTCCCAGATCGATCTGAGTAACTCCCAAT<br>CTTCTCTCTGCAGAGTCCAAATATGGTCCCCGTGTCCCC<br>CATGCCCAGGTAAGCCAACCCAGGCCTCGCCCTCCAGCTC<br>AAGGCGGGACAGGTGCCCTAGAGTAGCCTGCATCCAGGG<br>ACAGGCCCCAGCCGGGTGCTGACGCATCCACCTCCATCTC<br>TTCCTCAGCACCTGAGTTCCTGGGGGGACCATCAGTCTTC<br>CTGTTCCCCCCAAAACCCAAGGACACTCTCATGATCTCCC<br>GGACCCCTGAGGTCACGTGCGTGGTGGTGGACGTGAGCC<br>AGGAAGACCCCGAGGTCCAGTTCAACTGGTACGTGGATGG<br>CGTGGAGGTGCATAATGCCAAGACAAAGCCGCGGGAGGA<br>GCAGTTCAACAGCACGTACCGTGTGGTCAGCGTCCTCACC<br>GTCCTGCACCAGGACTGGCTGAACGGCAAGGAGTACAAGT<br>GCAAGGTCTCCAACAAAGGCCTCCCGTCCTCCATCGAGAA<br>AACCATCTCCAAAGCCAAAGGTGGGACCCACGGGGTGCG<br>AGGGCCACATGGACAGAGGTCAGCTCGGCCCACCCTCTG<br>CCCTGGGAGTGACCGCTGTGCCAACCTCTGTCCCTACAGG<br>GCAGCCCCGAGAGCCACAGGTGTACACCCTGCCCCCATC<br>CCAGGAGGAGATGACCAAGAACCAGGTCAGCCTGACCTG<br>CCTGGTCAAAGGCTTCTACCCCAGCGACATCGCCGTGGAG<br>TGGGAGAGCAATGGGCAGCCGGAGAACAACTACAAGACC<br>ACGCCTCCCGTCCTCGATTCCGACGGCTCCTTCTTCCTCT<br>ACAGCAGGCTAACCGTGGACAAGAGCAGGTGGCAGGAGG<br>GGAATGTCTTCTCATGCTCCGTGATGCATGAGGCTCTGCA<br>CAACCACTACACACAGAAGAGCCTCTCCCTGTCTCTGGGT<br>TGATGAGTGCCAGGGCCGGCAAGCCCCCGCTCCCCGGGC<br>TCTCGGGGTCGCGCGAGGATGCTTGGCACGTACCCCGTC<br>TACATACTTCCCAGGCACCCAGCATGGAAATAAAGCACCC<br>ACCACTGCCCTGGGCCCCTGTGAGACTGTGATGGTTCTTT<br>CCACGGGTCAGGCCGAGTCTGAGGCCTGAGTGACATGAG<br>GGAGGCAGAGCGGGTCCCACTGTCCCCACACTGGCCCAG<br>GCTGTGCAGGTGTGCCTGGGCCGCCTAGGGTGGGGCTCA<br>GCCAGGGGCTGCCCTCGGCAGGGTGGGGGATTTGCCAGC<br>GTGGCCCTCCCTCCAGCAGCAGGTACCTCGAG<br>(SEQ ID NO: 11) | GTCTCCTTGCTATAATTATCTGGGATAAGCATGCTGTTTTCTGTC<br>TGTCCCTAACATGCCCTGTGATTATCCGCAAACAACACACCCAA<br>GGGCAGAACTTTGTTACTTAAACACCATCCTGTTTGCTTCTTTCC<br>TCAGGAACTGTGGCTGCACCATCTGTCTTCATCTTCCCGCCATC<br>TGATGAGCAGTTGAAATCTGGAACTGCCTCTGTTGTGTGCCTGC<br>TGAATAACTTCTATCCCAGAGAGGCCAAAGTACAGTGGAAGGTG<br>GATAACGCCCTCCAATCGGGTAACTCCCAGGAGAGTGTCACAG<br>AGCAGGACAGCAAGGACAGCACCTACAGCCTCAGCAGCACCCT<br>GACGCTGAGCAAAGCAGACTACGAGAAACACAAAGTCTACGCC<br>TGCGAAGTCACCCATCAGGGCCTGAGCTCGCCCGTCACAAAGA<br>GCTTCAACAGGGGAGAGTGTTAGAGGGAGAAGTGCCCCCACCT<br>GCTCCTCAGTTCCAGCCTGACCCCCTCCCATCCTTTGGCCTCTG<br>ACCCTTTTTCCACAGGGGACCTACCCCTATTGCGGTCCTCCAGC<br>TCATCTTTCACCTCACCCCCCTCCTCCTCCTTGGCMAATTATG<br>CTAATGTTGGAGGAGAATGAATAAATAAAGTGAATCTTTGCACCT<br>GTGGTTTCTCTCTTTCCTCATTTAATAATTATTATCTGTT-<br>GTTTTA<br>CCAACTACTCAATTTCTCTTATAAGGGACTAAATATGTAGTCATC<br>CTAAGGCGCATAACCAAATAAAAATCATCCTTCATTCTATTTTA<br>CCCTATCATCCTCTGCAAGACAGTCCTCCCTCAAACCCACAAGC<br>CTTCTGTCCTCACAGTCCCCTGGGCCATGGTAGGAGAGACTTG<br>CTTCCTTGTTTTCCCCTCCTCAGCAAGCCCTCATAGTCCTTTTTA<br>AGGGTGACAGGTCTTACAGTCATATATCCTTTGATTCAATTCCCT<br>GAGAATCAACCAAAGCAAATTTTTCAAAAGAAGAAACCTGCTATA<br>AAGAGAATCATTCATTGCAACATGATATAAAATAACAACACAATA<br>AAAGCAATTAAATAAACAAACAATAGGGAAATGTTTAAGTTCATC<br>ATGGTACTTAGACTTAATGGAATGTCATGCCTTATTTA-<br>CATTTTTA<br>AACAGGTACTGAGGGACTCCTGTCTGCCAAGGGCCGTATTGAG<br>TACTTTCCACAACCTAATTTAATCCACACTATACTGTGAGATTAA<br>AAACATTCATTAAAATGTTGCAAAGGTTCTATAAAGCTGAGAGAC<br>AAATATATTCTATAACTCAGCAATCCCACTTCTAGA<br>(SEQ ID NO: 12) |
| hAC1-2B6A<br>36-<br>2B6-<br>Ab1 | 10C11 | AAGCTTGCCGCCACCATGGGATGGAGCTGTATCATCCTCT<br>TCTTGGTAGCAACAGCTACAGGTAAGGGGCTCACAGTAGC<br>AGGCTTGAGGTCTGGACATATATATGGGTGACAATGACAT<br>CCACTTTGCCTTTCTCTCCACAGGTGTCCACTCCCAGGTCC<br>AGCTGGTGCAATCTGGACCTGAAGTGAAGAAGCCTGGGT<br>CCTCAGTGAAGGTGTCCTGTAAGGCTTCTGGATATACCTTC<br>ACTGACTACTACATGAACTGGGTGAGGCAGGCCCCTGGAC<br>AGGGCCTTGAGTGGATTGGAGATATTAATCCTAACCGCGG<br>TGGGAACTACTTACAACCAGAAGTTCAAGGGCAGGGTGACC<br>ATCACTGTGGACAAGTCCACCAGCACAGCCTACATGGAAC<br>TCAGCAGCCTGAGATCTGAGGACACCGCAGTCTATTACTG<br>TGCAAGTTACTACGCCGTGGGCTACTGGGGCAAGGCAC<br>CACTGTGACAGTCTCCTCAGGTGAGTCCTTACAACCTCTCT<br>CTTCTATTCAGCTTAAATAGAMTACTGCATTTGTTGGGG<br>GGAAATGTGTGTATCTGAATTTCAGGTCATGAAGGACTAGG | AAGCTTGCCGCCACCATGGGATGGAGCTGTATCATCCTCTTCTT<br>GGTAGCAACAGCTACAGGTAAGGGGCTCACAGTAGCAGGCTTG<br>AGGTCTGGACATATATATGGGTGACAATGACATCCACTTTGCCT<br>CCACTCTCCCTGCCTGTCACCCCTGGAGAGCCCGCCTCCATCT<br>CTTGCAGATCTAGTCAGAGCCTTGTGCACAGTCATGGAAAAACC<br>TATCTGCATTGGTACCTGCAGAAGCCAGGCCAGTCTCCACAGCT<br>CCTGATCTACAAAGMCCAACCGGTTTTCTGGGGTCCCAGACA<br>GGTTCAGTGGCAGTGGTGGATCAGGGACAGATTTCACACTCAAGAT<br>CAGCAGAGTGGAGGCTGAGGATGTGGGAGMATTTCTGTTCTC<br>AAACTGCACATTTTCCCTACACCTTCGGAGGGGGGACCAAGGT<br>GGAAATCAAACGTGAGTAGAAMAAACTTTGCTTCCTCAGTTG<br>GATCCACTAGTCCAGTGTGGTGGAATTCTAAACTCTGAGGGGT<br>CGGATGACGTGGCCATTCMGCCTAAAGCATTGAGTTTACTGC<br>AAGGTCAGAAAAGCATGCAAAGCCCTCAGAATGGCTGCAAAGA |

TABLE 2-continued

Nucleotide Sequence of the heavy chain and light chain (H and L)

| antibody name | Hybridoma | Heavy chain (H) | Light chain (L) |
|---|---|---|---|
| | | GACACCTTGGGAGTCAGAAAGGGTCATTGGGAGCCCGGG<br>CTGATGCAGACAGACATCCTCAGCTCCCAGACTTCATGGC<br>CAGAGATTTATAGGATCCAGCMCTGGGGCAGGCCAGGC<br>CTGACCTTGGCTGGGGGCAGGGAGGGGGCTAAGGTGACG<br>CAGGTGGCGCCAGCCAGGTGCACACCCAATGCCCATGAG<br>CCCAGACACTGGACCCTGCATGGACCATCGCGGATAGACA<br>AGAACCGAGGGGCCTCTGCGCCCTGGGCCCAGCTCTGTC<br>CCACACCGCGGTCACATGGCACCACCTCTCTTGCAGCTTC<br>CACCAAGGGCCCATCCGTCTTCCCCCTGGCGCCCTGCTCC<br>AGATCGACCTCCGAGAGCACAGCCGCCCTGGGCTGCCTG<br>GTCAAGGACTACTTCCCCGAACCGGTGACGGTGTCGTGGA<br>ACTCAGGCGCCCTGACCAGCGGCGTGCACACCTTCCCGG<br>CTGTCCTACAGTCCTCAGGACTCTACTCCCTCAGCAGCGT<br>GGTGACCGTGCCCTCCAGCAGCTTGGGCACGAAGACCTA<br>CACCTGCAACGTAGATCACAAGCCCAGCAACACCAAGGTG<br>GACAAGAGAGTTGGTGAGAGGCCAGCACAGGGAGGGAGG<br>GTGTCTGCTGGAAGCCAGGCTCAGCCCTCCTGCCTGGAC<br>GCACCCCGGCTGTGCAGCCCCAGCCCAGGGCAGCAAGGC<br>ATGCCCCATCTGTCTCCTCACCCGGAGGCCTCTGACCACC<br>CCACTCATGCTCAGGGAGAGGGTCTTCTGGATTTTTCCAC<br>CAGGCTCCGGGCAGCCACAGGCTGGATGCCCCTACCCCA<br>GGCCCTGCGCATACAGGGGCAGGTGCTGCGCTCAGACCT<br>GCCAAGAGCCATATCCGGGAGGACCCTGCCCCTGACCTAA<br>GCCCACCCCAAAGGCCAAACTCTCCACTCCCTCAGCTCAG<br>ACACCTTCTCTCCTCCCAGATCGATCTGAGTAACTCCCAAT<br>CTTCTCTCTGCAGAGTCCAAATATGGTCCCCCGTGTCCCC<br>CATGCCCAGGTAAGCCAACCCAGGCCTCGCCCTCCAGCTC<br>AAGGCGGGACAGGTGCCCTAGAGTAGCCTGCATCCAGGG<br>ACAGGCCCCAGCCGGGTGCTGACGCATCCACCTCCATCTC<br>TTCCTCAGCACCTGAGTTCCTGGGGGACCATCAGTCTTC<br>CTGTTCCCCCCAAAACCCAAGGACACTCTCATGATCTCCC<br>GGACCCCTGAGGTCACGTGCGTGGTGGTGGACGTGAGCC<br>AGGAAGACCCCGAGGTCCAGTTCAACTGGTACGTGGATGG<br>CGTGGAGGTGCATAATGCCAAGACAAAGCCGCGGGAGGA<br>GCAGTTCAACAGCACGTACCGTGTGGTCAGCGTCCTCACC<br>GTCCTGCACCAGGACTGGCTGAACGGCAAGGAGTACAAGT<br>GCAAGGTCTCCAACAAAGGCCTCCCGTCCTCCATCGAGAA<br>AACCATCTCCAAAGCCAAAGGTGGGACCCACGGGGTGCG<br>AGGGCCACATGGACAGAGGTCAGCTCGGCCCACCCTCTG<br>CCCTGGGAGTGACCGCTGTGCCAACCTCTGTCCCTACAGG<br>GCAGCCCCGAGAGCCACAGGTGTACACCCTGCCCCCATC<br>CCAGGAGGAGATGACCAAGAACCAGGTCAGCCTGACCTG<br>CCTGGTCAAAGGCTTCTACCCCAGCGACATCGCCGTGGAG<br>TGGGAGAGCAATGGGCAGCCGGAGAACAACTACAAGACC<br>ACGCCTCCCGTCCTCGATTCCGACGGCTCCTTCTTCCTCT<br>ACAGCAGGCTAACCGTGGACAAGAGCAGGTGGCAGGAGG<br>GGAATGTCTTCTCATGCTCCGTGATGCATGAGGCTCTGCA<br>CAACCACTACACACAGAAGAGCCTCTCCCTGTCTCTGGGT<br>TGATGAGTGCCAGGGCCGGCAAGCCCCCGCTCCCCGGGC<br>TCTCGGGGTCGCGCGAGGATGCTTGGCACGTACCCCGTC<br>TACATACTTCCCAGGCACCCAGCATGGAAATAAAGCACCC<br>ACCACTGCCCTGGGCCCCTGTGAGACTGTGATGGTTCTTT<br>CCACGGGTCAGGCCGAGTCTGAGGCCTGAGTGACATGAG<br>GGAGGCAGAGCGGGTCCCACTGTCCCCACACTGGCCCAG<br>GCTGTGCAGGTGTGCCTGGGCCGCCTAGGGTGGGGCTCA<br>GCCAGGGGCTGCCCTCGGCAGGGTGGGGGATTTGCCAGC<br>GTGGCCCTCCCTCCAGCAGCAGGTACCTCGAG<br>(SEQ ID NO: 11) | GCTCCAACAAAACAATTTAGAACTTTATTAAGGAATAGGGGGAA<br>GCTAGGAAGAAACTCAAAACATCAAGATTTTAAATACGCTTCTTG<br>GTCTCCTTGCTATAATTATCTGGGATAAGCATGCTGTTTTCTGTC<br>TGTCCCTAACATGCCCTGTGATTATCCGCAAACAACACACCCAA<br>GGGCAGAACMGTTACTTAAACACCATCCTGMGCTTCTTTCC<br>TCAGGAACTGTGGCTGCACCATCTGTCTTCATCTTCCCGCCATC<br>TGATGAGCAGTTGAAATCTGGAACTGCCTCTGTTGTGTGCCTGC<br>TGAATAACTTCTATCCCAGAGAGGCCAAAGTACAGTGGAAGGTG<br>GATAACGCCCTCCAATCGGGTAACTCCCAGGAGAGTGTCACAG<br>AGCAGGACAGCAAGGACAGCACCTACAGCCTCAGCAGCACCCT<br>GACGCTGAGCAAAGCAGACTACGAGAAACACAAAGTCTACGCC<br>TGCGAAGTCACCCATCAGGGCCTGAGCTCGCCCGTCACAAAGA<br>GCTTCAACAGGGGAGAGTGTTAGAGGGAGAAGTGCCCCCACCT<br>GCTCCTCAGTTCCAGCCTGACCCCCTCCCATCCMGGCCTCTG<br>ACCCTMTCCACAGGGGACCTACCCCTATTGCGGTCCTCCAGC<br>TCATCTTTCACCTCACCCCCCTCCTCCTCTTGGCTTTAATTATG<br>CTAATGTTGGAGGAGAATGAATAAATAAAGTGAATCTTTGCACCT<br>GTGGTTTCTCTCMCCTCATTRATAATTATTATCTGTTGTTTTA<br>CCAACTACTCAAMCTCTTATAAGGGACTAAATATGTAGTCATC<br>CTAAGGCGCATAACCATTTATAAAAATCATCCTTCATTCT-<br>ATTTTA<br>CCCTATCATCCTCTGCAAGACAGTCCTCCCTCAAACCCACAAGC<br>CTTCTGTCCTCACAGTCCCCTGGGCCATGGTAGGAGAGACTTG<br>CTTCCTTGTTTTCCCCTCCTCAGCAAGCCCTCATAGTCCTTTTTA<br>AGGGTGACAGGTCTTACAGTCATATATCCTTTGATTCAATTCCCT<br>GAGAATCAACCAAAGCAAATTTTTCAAAAGAAGAAACCTGCTATA<br>AAGAGAATCATTCATTGCAACATGATATAAATAACAACACAATA<br>AAAGCAATTAAATAAACAAACAATAGGGAAATGTTTAAGTTCATC<br>ATGGTACTTAGACTTAATGGAATGTCATGCCTTATTTA-<br>CATTTTTA<br>AACAGGTACTGAGGGACTCCTGTCTGCCAAGGGCCGTATTGAG<br>TACTTTCCACAACCTAATTTAATCCACACTATACTGTGAGATTAA<br>AAACATTCATTAAAATGTTGCAAAGGTTCTATAAAGCTGAGAGAC<br>AAATATATTCTATAACTCAGCAATCCCACTTCTAGA<br>(SEQ ID NO: 13) |

TABLE 3

Amino Acid Sequence of the heavy chain and light chain constant regions (HC and LC)

| Antibody name | Hybrid-oma | Heavy chain constant regions (NC) | | | | Light chain constant regions (LC) |
|---|---|---|---|---|---|---|
| | | CH1 | Hinge | CH2 | CH3 | |
| hAC1-36-3A8-Ab1 and hAC1-36-2B6-Ab1 | 3A8A12G7 and/or 2B6A10C11 | ASTKGPSVF PLAPCSRST SESTAALGC LVKDYFPEP VTVSWNSGA LTSGVHTFP AVLQSSGLY SLSSVVTVPS SSLGTKTYT CNVDHKPSN TKVDKRV (SEQ ID NO: 14) | ESKYGPPCP PCP (SEQ ID NO: 15) | APEFLGGPS VFLFPPKPKDTLPPSQEEM TLMISRTPEVTKNQVSLTC CVVVDVSQ EDPEVQFNW YVDGVEVHN AKTKPREEQ FNSTYRWS VLTVLHCIDWKSRWQEGN LNGKEYKCK VSNKGLPSS EKTISKAK (SEQ ID NO: 16) | GQPREPQVY CLLNNFYPREAKVQWKVDNALQSGNS QESVTEQDSKDSTYSLSSTLTLSKAD LVKGFYPSDIYEKHKVYACEVTHQGLSSPVFKSFNR AVEWESNG QPENNYKTT PPVLDSDGS FFLYSRLTVD IALHNHYTQK SLSLSLG (SEQ ID NO: 17) | RTVAAPSVFIFPPSDEQLKSGTASVV CLLNNFYPREAKVQWKVDNALQSGNS QESVTEQDSKDSTYSLSSTLTLSKAD GEC(SEQ ID NO: 18) |

TABLE 4

Longest isoform of human Tau (441aa), also called Tau40

| | |
|---|---|
| Longest isoform of human Tau (441aa), also called Tau40 (SEQ ID NO: 19) Microtubule-associated protein tau isoform 2 [*Homo sapiens*] NCBI Reference Sequence: NP_005901.2 | MAEPRQEFEV MEDHAGTYGL GDRKDQGGYT MHQDQEGDTD AGLKESPLQT PTEDGSEEPG SETSDAKSTP TAEDVTAPLV DEGAPGKQAA AQPHTEIPEG TTAEEAGIGD TPSLEDEAAG HVTQARMVSK SKDGTGSDDK KAKGADGKTK IATPRGAAPP GQKGQANATR IPAKTPPAPK TPPSSGEPPK SGDRSGYSSP GSPGTPGSRS RTPSLPTPPT REPKKVAVVR TPPKSPSSAK SRLQTAPVPM PDLKNVKSKI GSTENLKHQP GGGKVQIINK KLDLSNVQSK CGSKDNIKHV PGGGSVQIVY KPVDLSKVTS KCGSLGNIHH KPGGGQVEVK SEKLDFKDRV QSKIGSLDNI THVPGGGNKK IETHKLTFRE NAKAKTDHGA EIVYKSPVVS GDTSPRHLSN VSSTGSIDMV DSPQLATLAD EVSASLAKQG L (SEQ ID NO: 19) |

TABLE 5

Phospho- and non-phospho Tau library sequences used for the antibody epitope mapping. Peptide scanning libraries for phospho- and non-phospho sequences (A). Ala-scanning library for determining the required residues (B).

A

| | | | | | | | | | Tau(441) amino acid number | | | | | | | | | | |
|---|---|---|---|---|---|---|---|---|---|---|---|---|---|---|---|---|---|---|---|
| | | | | | | | | | Amino acid | | | | | | | | | | |
| Peptide no. | 401 | 402 | 403 | 404 | 405 | 406 | 407 | 408 | 409 | 410 | 411 | 412 | 413 | 414 | 415 | 416 | 417 | 418 | SEQ ID NO: |
| Phospho-peptides | | | | | | | | | | | | | | | | | | | |
| T3.17 | G | D | T | S(p) | P | R | H | L | S(p) | N | V | S | S | T | G | S | I | D | 69 |
| T4.11 | | D | T | S(p) | P | R | H | L | S(p) | | | | | | | | | | 33 |
| T4.12 | | D | T | S(p) | P | R | H | L | S(p) | N | | | | | | | | | 34 |
| T4.13 | | | T | S(p) | P | R | H | L | S(p) | N | V | | | | | | | | 35 |
| T4.14 | | | | S(p) | p | R | H | L | S(p) | N | V | S | | | | | | | 36 |
| T4.15 | | | | | P | R | H | L | S(p) | N | V | S | S | | | | | | 37 |
| T4.16 | | | | | | R | H | L | S(p) | N | V | S | S | T | | | | | 38 |
| T4.17 | | | | | | | H | L | S(p) | N | V | S | S | T | G | | | | 39 |
| T4.18 | | | | | | | | L | S(p) | N | V | S | S | T | G | S | | | 40 |
| T4.19 | | | | | | | | | S(p) | N | V | S | S | T | G | S | I | | 41 |
| T4.20 | | | | | | | | | | N | V | S | S | T | G | S | I | D | 42, 43 |

| | | | | | | | | | Amino acid | | | | | | | | | | |
|---|---|---|---|---|---|---|---|---|---|---|---|---|---|---|---|---|---|---|---|
| Peptide no. | 401 | 402 | 403 | 404 | 405 | 406 | 407 | 408 | 409 | 410 | 411 | 412 | 413 | 414 | 415 | 416 | 417 | 418 | SEQ ID NO: |
| Non-phospho-peptides | | | | | | | | | | | | | | | | | | | |
| T3.26 | G | D | T | S | P | R | H | L | S | N | V | S | S | T | G | S | I | D | 70 |
| T4.21 | | D | T | S | P | R | H | L | S | | | | | | | | | | 44 |
| T4.22 | | D | T | S | P | R | H | L | S | N | | | | | | | | | 45 |
| T4.23 | | | T | S | P | R | H | L | S | N | V | | | | | | | | 46 |
| T4.24 | | | | S | P | R | H | L | S | N | V | S | | | | | | | 47 |
| T4.25 | | | | | P | R | H | L | S | N | V | S | S | | | | | | 48 |
| T4.26 | | | | | | R | H | L | S | N | V | S | S | T | | | | | 49 |
| T4.27 | | | | | | | H | L | S | N | V | S | S | T | G | | | | 50 |
| T4.28 | | | | | | | | L | S | N | V | S | S | T | G | S | | | 51 |
| T4.19 | | | | | | | | | S | N | V | S | S | T | G | S | I | | 52 |
| T4.20 | | | | | | | | | | N | V | S | S | T | G | S | I | D | 53, 54 |

B

| Peptide No. | 405 | 406 | 407 | 408 | 409 | 410 | 411 | 412 | SEQ ID NO: |
|---|---|---|---|---|---|---|---|---|---|
| T4-Ala.A1 | P | R | H | L | S(p) | N | V | S | 55 |
| T4-Ala.A2 | P | R | H | L | S(p) | N | V | S | 56 |
| T4-Ala.A3 | A | R | H | L | S(p) | N | V | S | 57 |
| T4-Ala.A4 | P | A | H | L | S(p) | N | V | S | 58 |

TABLE 5-continued

Phospho- and non-phospho Tau library sequences used for the antibody epitope mapping. Peptide scanning libraries for phospho- and non-phospho sequences (A). Ala-scanning library for determining the required residues (B).

| | | | | | | | | |
|---|---|---|---|---|---|---|---|---|
| T4-Ala.A5 | P | R | A | L | S(p) | N | V | S | 59 |
| T4-Ala.A6 | P | R | H | A | S(p) | N | V | S | 60 |
| T4-Ala.A7 | P | R | H | L | A | N | V | S | 61 |
| T4-Ala.A8 | P | R | H | L | S(p) | A | V | S | 62 |
| T4-Ala.A9 | P | R | H | L | S(p) | N | A | S | 63 |
| T4-Ala.A10 | P | R | H | L | S(p) | N | V | A | 64 |
| T4-Ala.A11 | P | A | A | L | S(p) | N | V | S | 65 |
| T4-Ala.A12 | P | R | H | A | S(p) | N | V | S | 66 |
| T4-Ala.A13 | P | A | A | A | S(p) | N | V | S | 67 |
| T4-Ala.A14 | P | A | A | A | S(p) | N | V | S | 68 |

TABLE 6

Modified Amino Acid Sequence of the heavy chain variable regions (HCVR)

| Antibody name | HCVR |
|---|---|
| hAC1-36-3A8-Ab1.v2 | EVQLVQSGAEVKKPGSSVKVSCKASGYTFTDYYMNWV RQAPGQGLEWIGNIPNGRGGTTYNQKFKGRVTITVDK STSTAYMELSSLRSEDTAVYYCASYYAVGYWGQGTTV TVSS (SEQ ID NO: 20) |
| hAC1-36-2B6-Ab1.v2 | EVQLVQSGAEVKKPGSSVKVSCKASGYTFTDYYMNWV RQAPGQGLEWIGDINPNRGGTTYNQKFKGRVTITVDK STSTAYMELSSLRSEDTAVYYCASYYAVGYWGQGTTV TVSS (SEQ ID NO: 21) |

TABLE 7

Full-length Amino Acid Sequence of the heavy chain and light chain

| Antibody name | Hybridoma | Heavy Chain | Light chain |
|---|---|---|---|
| hAC1-36-3A8A 3A8-Ab1 (IgG4) | 12G7 | QVQLVQSGAEVKKPGSSVKVSCKASGYTFTDYYMNWV RQAPGQGLEWIGDINPNRGGTTYNQKFKGRVTITVDKS TSTAYMELSSLRSEDTAVYYCASYYAVGYWGQGTTVT VSSASTKGPSVFPLAPCSRSTSESTAALGCLVKDYFPE PVTVSWNSGALTSGVHTFPAVLQSSGLYSLSSVVTVPS SSLGTKTYTCNVDHKPSNTKVDKRVESKYGPPCPPCPA PEFLGGPSVFLFPPKPKDTLMISRTPEVTCVVVDVSQED PEVQFNWYVDGVEVHNAKTKPREEQFNSTYRVVSVLT VLHQDWLNGKEYKCKVSNKGLPSSIEKTISKAKGQPRE PQVYTLPPSQEEMTKNQVSLTCLVKGFYPSDIAVEWES NGQPENNYKTTPPVLDSDGSFFLYSRLTVDKSRWQEG NVFSCSVMHEALHNHYTQKSLSLSLG (SEQ ID NO: 24) | DIVMTQTPLSLPVTPGEPAS ISCRSSQRLVHSGKTYLH WYLQKPGQSPQLLIYKVSN RFSGVPDRFSGSGSGTDFT LKISRVEAEDVGVYFCSQTA HFPYTFGGGTKVEIKRTVAA PSVFIFPPSDEQLKSGTASV VCLLNNFYPREAKVQWKVD NALQSGNSQESVTEQDSK DSTYSLSSTLTLSKADYEKH KVYACEVTHQGLSSPVTKS FNRGEC (SEQ ID NO: 22) |
| hAC1-36-2B6A 2136-Ab1 (IgG4) | 10C11 | QVQLVQSGAEVKKPGSSVKVSCKASGYTFTDYYMNWV RQAPGQGLEWIGDINPNRGGTTYNQKFKGRVTITVDKS TSTAYMELSSLRSEDTAVYYCASYYAVGYWGQGTTVT VSSASTKGPSVFPLAPCSRSTSESTAALGCLVKDYFPE PVTVSWNSGALTSGVHTFPAVLQSSGLYSLSSVVTVPS SSLGTKTYTCNVDHKPSNTKVDKRVESKYGPPCPPCPA PEFLGGPSVFLFPPKPKDTLMISRTPEVTCVVVDVSQED PEVQFNWYVDGVEVHNAKTKPREEQFNSTYRWSVLT VLHQDWLNGKEYKCKVSNKGLPSSIEKTISKAKGQPRE PQVYTLPPSQEEMTKNQVSLTCLVKGFYPSDIAVEWES NGQPENNYKTTPPVLDSDGSFFLYSRLTVDKSRWQEG NVFSCSVMHEALHNHYTQKSLSLSLG (SEQ ID NO: 25) | DIVMTQTPLSLPVTPGEPAS ISCRSSQRLVHSGKTYLH WYLQKPGQSPQLLIYKVSN RFSGVPDRFSGSGSGTDFT LKISRVEAEDVGVYFCSQTA HFPYTFGGGTKVEIKRTVAA PSVFIFPPSDEQLKSGTASV VCLLNNFYPREAKVQWKVD NALQSGNSQESVTEQDSK DSTYSLSSTLTLSKADYEKH KVYACEVTHQGLSSPVTKS FNRGEC (SEQ ID NO: 23) |
| hAC1-36-3A8-Ab1.v2 (IgG4) | | EVQLVQSGAEVKKPGSSVKVSCKASGYTFTDYYMNWV RQAPGQGLEWIGDINPNRGGTTYNQKFKGRVTITVDKST STAYMELSSLRSEDTAVYYCASYYAVGYWGQGTTVTVS SASTKGPSVFPLAPCSRSTSESTAALGCLVKDYFPEPVTVR FSWNSGALTSGVHTFPAVLQSSGLYSLSSVVTVPSSSLGTKL TYTCNVDNKPSNTKVDKRVESKYGPPCPPCPAPEFLGGP SVFLFPPKPKDTLMISRTPEVICVVVDVSQEDPEVQFNW YVDGVEVHNAKTKPREEQFNSTYRVVSVLTVLHQDWL NGKEYKCKVSNKGLPSSIEKTISKAKGQPREPQVYTLPPSNALQSGNSQESVTEQDSK QEEMTKNQVSLTCLVKGFYPSDIAVEWESNGQPENNYK TTPPVLDSDGSFFLYSRLIVDKSRWQEGNVESCSVMHEA LHNHYTQKSLSLSLGK (SEQ ID NO: 26) | DIVMTQTPLSLPVTPGEPAS ISCRSSQRLVHSGKTYLH WYLQKPGQSPQLLIYKVSN RFSGVPDRFSGSGSGTDFT LKISRVEAEDVGVYFCSQTA HFPYTFGGGTKVEIKRTVAA PSVFIFPPSDEQLKSGTASV VCLLNNFYPREAKVQWKVD NALQSGNSQESVTEQDSK DSTYSLSSTLTLSKADYEKH KVYACEVTHQGLSSPVTKS FNRGEC (SEQ ID NO: 22) |
| hAC1-36-3A8-Ab1.v3 IgG1) | | EVQLVQSGAEVKKPGSSVKVSCKASGYTFTDYYMNWV RQAPGQGLEWIGDINPNRGGTTYNQKFKGRVTITVDKST STAYMELSSLRSEDTAVYYCASYYAVGYWGQGTTVTVS SASTKGPSVFPLAPSSKSTSGGTAALGCLVKDYFPEPVTVR FSWNVNHKPSNTKVDKKVEPKSCDKTHTCPPCPAPELL GGPSVFLFPPKPKDTLMISRTPEVTCVVVDVSHEDPEVK FNWYVDGVEVHNAKTKPREEQYNSTYRVVSVLTVLFHQD WLNGKEYKCKVSNKALPAPIEKTISKAKGQPREPQVYTL PPSREEMTKNQVSLTCLVKGFYPSDIAVEWESNGQPENN YKTTPPVLDSDGSFELYSKLTVDKSRWQQGNVFSCSVM HEALHNHYTQKSLSLSPGK (SEQ ID NO: 27) | DIVMTQTPLSLPVTPGEPAS ISCRSSQRLVHSGKTYLH WYLQKPGQSPQLLIYKVSN RFSGVPDRFSGSGSGTDFT LKISRVEAEDVGVYFCSQTA HFPYTFGGGTKVEIKRTVAA PSVFIFPPSDEQLKSGTASV VCLLNNFYPREAKVQWKVD NALQSGNSQESVTEQDSK DSTYSLSSTLTLSKADYEKH KVYACEVTHQGLSSPVTKS FNRGEC (SEQ ID NO: 22) |
| hAC1-36-3A8-Ab1.v4 | | EVQLVQSGAEVKKPGSSVKVSCKASGYTFTDYYMNWV RQAPGQGLEWIGDINPNRGGTTYNQKFKGRVTITVDKST STAYMELSSLRSEDTAVYYCASYYAVGYWGQGTTVTVS | DIVMTQTPLSLPVTPGEPAS ISCRSSQRLVHSGKTYLH WYLQKPGQSPQLLIYKVSN |

TABLE 7-continued

Full-length Amino Acid Sequence of the heavy chain and light chain

| Antibody name | Hybridoma | Heavy Chain | Light chain |
|---|---|---|---|
| IgG1) N297G) | | SASTKGPSVFPLAPSSKSTSGGTAALGCLVKDYFPEPVTVRFSGVPDRFSGSGSGTDFT SWNSGALTSGVHTFPAVLQSSGLYSLSSVVTVPSSSLGTQLKISRVEAEDVGWFCSQTA TYICNVNHKPSNTKVDKKVEPKSCDKTHTCPPCPAPELL HFPYTFGGGTKVEIKRTVAA GGPSVFLFPPKPKDTLMISRTPEVICVVVDVSHEDPEVKFPSVFIFPPSDEQLKSGTASV NWYVDGVEVHNAKTKPREEQYGSTYRVVSVLTVLHQD VCLLNNFYPREAKVQWKVD WLNGKEYKCKVSNKALPAPIEKTISKAKGQPREPQVYTL NALQSGNSQESVTEQDSK PPSREEMTKNQVSLTCLVKGFYPSDIAVEWESNGQPENN DSTYSLSSTLTLSKADYEKH YKTTPPVLDSDGSFFLYSKLTVDKSRWQQGNVFSCSVM KVYACEVTHQGLSSPVTKS HEALHNHYTQKSLSLSPGK FNRGEC (SEQ ID NO: 28) (SEQ ID NO: 22) |  |
| hAC1-36-2B6-Ab1.v2 lgG4) | | EVQLVQSGAEVKKPGSSVKVSCKASGYTFTDYYMNWV RQAPGQGLEWIGDINPNRGGTTYNQKFKGRVTITVDKST STAYMELSSLRSEDTAVYYCASYYAVGYWGQGTTVTVS SASTKGPSVFPLAPSSKSTSGGTAALGCLVKDYFPEPVTVRFSGVPDRFSGSGSGTDFT SWNSGALTSGVHTFPAVLQSSGLYSLSSVVTVPSSSLGTQLKISRVEAEDVGVYFCSQTA TYICNVNHKPSNTKVDKKVEPKSCDKTHTCPPCPAPELL HFPYTFGGGTKVEIKRTVAA SVFLFPPKPKDTLMISRTPEVTCVVVDVSQEDPEVQFNW PSVFIFPPSDEQLKSGTASV YVDGVEVHNAKTKPREEQFNSTYRVVSVLTVLHQDWL VCLLNNFYPREAKVQWKVD NGKEYKCKVSNKGLPSSIEKTISKAKGQPREPQVYTLPPSNALQSGNSQESVTEQDSK QEEMTKNQVSLTCLVKGEYPSDIAVEWESNGQPENNYK DSTYSLSSTLTLSKADYEKH TTPPVLDSDGSFFLYSRLTVDKSRWQEGNVFSCSVMHEA KVYACEVTHQGLSSPVTKS LHNHYTQKSLSLSLGK FNRGEC (SEQ ID NO: 29) (SEQ ID NO: 23) | DIVMTQTPLSLPVTPGEPAS ISCRSSQSLVHSHGKTYLH WYLQKPGQSPQLLIYKVSN |
| hAC1-36-2B6-Ab1.v3 (lgG1) | | EVQLVQSGAEVKKPGSSVKVSCKASGYTFTDYYMNWV RQAPGQGLEWIGDINPNRGGTTYNQKFKGRVTITVDKST STAYMELSSLRSEDTAVYYCASYYAVGYWGQGTTVTVS SASTKGPSVFPLAPSSKSTSGGTAALGCLVKDYFPEPVTVRFSGVPDRFSGSGSGTDFT SWNSGALTSGVHTFPAVLQSSGLYSLSSVVTVPSSSLGTQLKISRVEAEDVGWFCSQTA TYICNVNHKPSNTKVDKKVEPKSCDKTHTCPPCPAPELL HFPYTFGGGTKVEIKRTVAA GGPSVFLFPPKPKDTLMISRTPEVTCVVVDVSHEDPEVKFPSVFIFPPSDEQLKSGTASV NWYVDGVEVHNAKTKPREEQYNSTYRVVSVLTVLHQD VCLLNNFYPREAKVQWKVD WLNGKEYKCKVSNKALPAPIEKTISKAKGQPREPQVYTL NALQSGNSQESVTEQDSK PPSREEMTKNQVSLTCLVKGFYPSDIAVEWESNGQPENN DSTYSLSSTLTLSKADYEKH YKTTPPVLDSDGSFFLYSKLTVDKSRWQQGNVESCSVM KVYACEVTHQGLSSPVTKS HEALHNHYTQKSLSLSPGK FNRGEC (SEQ ID NO: 30) (SEQ ID NO: 23) | DIVMTQTPLSLPVTPGEPAS ISCRSSQSLVHSHGKTYLH VVYLQKPGQSPQLLIYKVSN |
| hAC1-36-2B6-Ab1.v4 (lgG1 N297G) | | EVQLVQSGAEVKKPGSSVKVSCKASGYTFTDYYMNWV RQAPGQGLEWIGDINPNRGGTTYNQKFKGRVTITVDKST STAYMELSSLRSEDTAVYYCASYYAVGYWGQGTTVTVS SASTKGPSVFPLAPSSKSTSGGTAALGCLVKDYFPEPVTVRFSGVPDRFSGSGSGTDFT SWNSGALTSGVHTFPAVLQSSGLYSLSSVVTVPSSSLGTQLKISRVEAEDVGWFCSQTA TYICNVNHKPSNTKVDKKVEPKSCDKTHTCPPCPAPELL HFPYTFGGGTKVEIKRTVAA GGPSVFLFPPKPKDTLMISRTPEVTCVVVDVSHEDPEVKFPSVFIFPPSDEQLKSGTASV NWYVDGVEVHNAKTKPREEQYGSTYRVVSVLTVLHQD VCLLNNFYPREAKVQWKVD WLNGKEYKCKVSNKALPAPIEKTISKAKGQPREPQVYTL NALQSGNSQESVTEGDSK PPSREEMTKNQVSLTCLVKGFYPSDIAVEWESNGQPENN DSTYSLSSTLTLSKADYEKH YKTTPPVLDSDGSFFLYSKLTVDKSRWQQGNVFSCSVM KVYACEVTHQGLSSPVTKS HEALHNHYTQKSLSLSPGK FNRGEC (SEQ ID NO: 31) (SEQ ID NO: 23) | DIVMTQTPLSLPVTPGEPAS ISCRSSQSLVHSHGKTYLH WYLQKPGQSPQLLIYKVSN |

REFERENCE LIST

Alonso A. D., et al. (1997) Proc. Natl. Acad. Sci. U.S.A., 94, 298-303
Alonso A C et al. (2008), Curr Alzheimer Res 5:375-384.
Alving et al., (1992) Infect. Immun. 60:2438-2444
Asuni et al., (2007) J Neurosc. 27 (34), 9115-29
Braak H., et al, (1993) Eur. Neurol., 33, 403-408
Gill et al, Nature Med. 9: 589-595 (2003)
Greenberg S. G., et al. (1992) J Biol. Chem., 267, 564-569.
Harlow and Lane Antibodies: A Laboratory Manual (Cold Spring Harbor Laboratory, New York 1988 555-612
Hodgson et al., (1991) Bio/Technoloy, 9:421
Hoffmann R., et al (1997) Biochemistry, 36, 8114-8124.
Jicha G A, Weaver et al (1999), J Neurosci 19:7486-7494.
Kabat E A, Wu T T, Perry H M, Gottesman K S, Foeller C. Sequences of proteins of Immunological Interest, US Department of Health and Human Services, 1991
Kennedy, J. H., et al., 1976 (Clin. Chim. Acta 70:1-31)
Khaw, B. A. et al. (1982) J. Nucl. Med. 23:1011-1019
Lewis et al., (2000) Nature Genetics, 25:402-405
Masliah et al., (2005) Neuron, 46(6), 857-68
Masliah et al., (2011) PLoS ONE, Volume 6(4), e19338, pp-1-17
Muhs et al., (2007) Proc Natl Acad Sci USA, 104(23), 9810-5
Muyllaert et al, (2006) Rev Neurol, 162(10), 903-907
Muyllaert et al, (2008) Genes Brain Behav., Suppl. 1, 57-66
Neuwelt, E. A., Implication of the Blood-Brain Barrier and its Manipulation, Vols 1 & 2, Plenum Press, N. Y. (1989))
Nicolau et. al. (2002) Proc Natl. Acad. Sci USA 99, 2332-2337
Nicoll et al., (2003) Nature Med, 9, 448-452
Oddo et al., (2004) Neuron, 43, 321-332
Queen et al., (1989) Proc. Natl Acad Sci USA, 86:10029-10032

Papanastassiou et al., Gene Therapy 9: 398-406 (2002)
Reig S., et al. (1995), Acta Neuropathol., 90, 441-447
Ribe et al., (2005) Neurobiol Dis, 20(3), 814-22
Roberson et al, (2007) Science, 316 (5825), 750-4
Rosenmann et al., (2006) Arch Neurol, 63(10), 1459-67
Rousseaux et al Methods Enzymology, (1986), Academic Press 121:663-69
Schurs, A H W M., et al. 1977 (Clin. Chim Acta 57:1-40
Terwel et al., (2006) J Biol Chem, 280, 3963-3973
Terwel et al, (2008) Am J pathol., 172(3), 786-98
Urushitiani et al., (2007) Proc. Natl Acad Sci USA, 104(79, 2495-500
Vandebroek T, et al., "*Phosphorylation and Aggregation of Protein Tau in Humanized Yeast Cells and in Transgenic Mouse Brain*"; 7th International Conference on Alzheimer's and Parkinson's Disease, Sorrento, Italy, Mar. 9-13, 2005, pp 15-19
Vandebroek T, et al (2006), J Biol Chem 281:25388-25397
Vanhelmont T, et al (2010, FEMS Yeast Res 10:992-1005
Wagner et al (2002) Journal of Liposome Research Vol 12(3), pp 259-270

WO2010/115843
WO 2004/058258
WO 96/13590
WO 96/29605
U.S. Patent Publication No. 2002/0038086
U.S. Patent Publication No. 2003/0083299
U.S. Patent Publication No. 2002/0025313
U.S. Patent Publication No 2004/0204354
U.S. Patent Publication No 2004/0131692
U.S. Patent Publication No 2002/0065259
U.S. Patent Publication No 2003/0162695
U.S. Patent Publication No 2005/0124533
U.S. Patent Publication No 2005/0089473
U.S. Patent Publication No 2003/0073713
U.S. Patent Publication No 2003/0129186
U.S. Pat. No. 5,112,596,
U.S. Pat. No. 5,268,164,
U.S. Pat. No. 5,506,206,
U.S. Pat. No. 5,686,416
U.S. Pat. No. 5,004,697

The invention claimed is:

1. A humanized antibody, or a functional fragment thereof, which binds to a phosphoepitope on a human Tau protein comprising Tau aa 404-411 with a phosphorylated Ser at position 409 (pS409), wherein the antibody or functional fragment thereof comprises a heavy chain variable region (HCVR) comprising a CDR1 with the amino acid sequence shown in SEQ ID NO: 1, a CDR2 with the amino acid sequence shown in SEQ ID NO: 2, and a CDR3 with the amino acid sequence shown in SEQ ID NO: 3, and a light chain variable region (LCVR) comprising a CDR1 with the amino acid sequence shown in SEQ ID NO: 4 or SEQ ID NO: 10, a CDR2 with the amino acid sequence shown in SEQ ID NO: 5, and a CDR3 with the amino acid sequence shown in SEQ ID NO: 6;
wherein the HCVR comprises an amino acid sequence having at least 95% identity to the sequence shown in SEQ ID NO: 7, and the LCVR comprises an amino acid sequence having at least 95% identity to the sequence shown in SEQ ID NO: 8 or SEQ ID NO: 9.

2. The humanized antibody or functional fragment thereof of claim 1, which does not bind to the corresponding unphosphorylated epitope.

3. The humanized antibody or functional fragment thereof of claim 1, wherein the HCVR comprises an amino acid sequence having at least 99% identity to the sequence shown in SEQ ID NO: 7, and the LCVR comprises an amino acid sequence having at least 99% identity to the sequence shown in SEQ ID NO: 8 or SEQ ID NO: 9.

4. The humanized antibody or functional fragment thereof of claim 1, wherein the HCVR comprises the amino acid sequence shown in SEQ ID NO: 7, and the LCVR comprises the amino acid sequence shown in SEQ ID NO: 8 or SEQ ID NO: 9.

5. The humanized antibody or functional fragment thereof of claim 1, which comprises a heavy chain constant region selected from SEQ ID NOs: 14-17 and a light chain constant region as shown in SEQ ID NO: 18.

6. The humanized antibody or functional fragment thereof of claim 5, comprising a heavy chain constant region with a mutation in the hinge region that prevents Fab arm exchange.

7. The humanized antibody or functional fragment thereof of claim 6, wherein the heavy chain hinge region comprises a Ser to Pro mutation at position 228 (S228P).

8. The humanized antibody or functional fragment thereof of claim 1, comprising a heavy chain constant region with a mutation at the C-terminus.

9. The humanized antibody or functional fragment thereof of claim 8, wherein the heavy chain comprises a deletion of the C-terminal lysine (des-K).

10. The humanized antibody or functional fragment thereof of claim 1, wherein said antibody is of the IgG1, IgG2, IgG3, or the IgG4 isotype.

11. The humanized antibody or functional fragment thereof of claim 1, wherein said antibody or functional fragment thereof has a $K_D$ for human Tau protein comprising a phosphorylated Ser at position 409 (pS409) of between 0.1 nM and 80 nM.

12. The humanized antibody or functional fragment thereof of claim 1, which binds to an aggregated microtubule-associated and hyperphosphorylated tau protein.

13. A pharmaceutical composition comprising the humanized antibody or functional fragment thereof of claim 1, together with a pharmaceutically acceptable carrier or excipient.

14. A polynucleotide encoding the humanized antibody or functional fragment thereof of claim 1.

15. A host cell comprising the polynucleotide of claim 14.

16. A process for producing a humanized antibody or functional fragment thereof comprising culturing the host cell of claim 15 under conditions suitable for expression of the antibody or fragment, and recovering the antibody or fragment.

17. A method for modulating soluble and/or insoluble Tau levels in the brain of a mammal or a human, comprising administering to said mammal or human, the humanized antibody or functional fragment thereof according to claim 1.

18. A method for slowing the progression of a tau-protein-associated disease, disorder or condition in a mammal or human comprising administering to said mammal or human, suffering from such a disease or condition, the humanized antibody or functional fragment thereof according to claim 1.

19. A method for improving the symptoms associated with tau-protein-associated diseases, disorders or conditions in a mammal or a human, comprising administering to said mammal or human, suffering from such a disease or condition, the humanized antibody or functional fragment thereof according to claim 1.

20. A method for determining whether a patient is suffering from or at risk of developing a tau-protein-associated disease, disorder or condition comprising detecting the immunospecific binding of the or humanized antibody or functional fragment thereof according to claim 1 to an epitope of the tau protein in a sample or in situ, which includes the steps of
   a. bringing the sample suspected to contain tau protein into contact with the humanized antibody or functional fragment thereof according to claim 1;
   b. allowing said antibody, or a functional fragment thereof, to bind to the tau protein to form an immunological complex;

c. detecting the formation of the immunological complex;
d. correlating the presence or absence of the immunological complex with the presence or absence of tau protein in the sample or specific body part; and
e. comparing the amount of said immunological complex to a normal control value;

wherein an increase in the amount of said aggregate compared to a normal control value indicates that said patient is suffering from or is at risk of developing an tau-protein-associated disease or condition.

21. A method for monitoring a tau-protein-associated disease in a patient following treatment with the humanized antibody or functional fragment thereof according to claim 1, wherein said method comprises:
    a. bringing a sample or a specific body part suspected to contain tau protein into contact with the humanized antibody or functional fragment thereof according to claim 1;
    b. allowing said antibody, or a functional fragment thereof, to bind to the tau protein to form an immunological complex;
    c. detecting the formation of the immunological complex;
    d. correlating the presence or absence of the immunological complex with the presence or absence of tau protein in the sample or specific body part, and
    e. comparing the amount of said immunological complex to a normal control value,
    wherein an increase in the amount of said aggregate compared to a normal control value indicates that said patient still suffers from a tau-protein-associated disease.

22. A method for predicting responsiveness of a patient being treated with the humanized antibody or functional fragment thereof according to claim 1, comprising
    a. bringing a sample or a specific body part suspected to contain tau protein into contact with the humanized antibody or functional fragment thereof according to claim 1;
    b. allowing said antibody, or a functional fragment thereof, to bind to the tau protein to form an immunological complex;
    c. detecting the formation of the immunological complex;
    d. correlating the presence or absence of the immunological complex with the presence or absence of tau protein in the sample or specific body part, and
    e. comparing the amount of said immunological complex before and after onset of the treatment,
    wherein a decrease in the amount of said aggregate indicates that said patient has a high potential of being responsive to the treatment.

* * * * *